(12) United States Patent
Chen et al.

(10) Patent No.: US 9,814,699 B2
(45) Date of Patent: *Nov. 14, 2017

(54) CHEMICAL COMPOUNDS

(71) Applicant: Janssen Pharmaceuticals, Inc., Titusville, NJ (US)

(72) Inventors: Pingyun Chen, Durham, NC (US); Ricky Couch, Durham, NC (US); Maosheng Duan, Durham, NC (US); Beth Adams Norton, Durham, NC (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/040,222

(22) Filed: Feb. 10, 2016

(65) Prior Publication Data

US 2016/0158201 A1 Jun. 9, 2016

Related U.S. Application Data

(63) Continuation of application No. 14/849,190, filed on Sep. 9, 2015, now abandoned, which is a continuation of application No. 14/472,293, filed on Aug. 28, 2014, now Pat. No. 9,150,587, which is a continuation of application No. 13/915,674, filed on Jun. 12, 2013, now Pat. No. 8,853,416, which is a continuation of application No. 13/677,358, filed on Nov. 15, 2012, now Pat. No. 8,492,554, which is a continuation of application No. 12/936,545, filed as application No. PCT/US2010/046782 on Aug. 26, 2010, now Pat. No. 8,344,155.

(60) Provisional application No. 61/239,855, filed on Sep. 4, 2009, provisional application No. 61/297,324, filed on Jan. 22, 2010, provisional application No. 61/348,767, filed on May 27, 2010.

(51) Int. Cl.
| | |
|---|---|
| C07D 491/107 | (2006.01) |
| C07D 491/113 | (2006.01) |
| C07D 495/10 | (2006.01) |
| C07D 487/10 | (2006.01) |
| A61K 31/4178 | (2006.01) |
| C07D 403/12 | (2006.01) |
| C07D 403/14 | (2006.01) |
| C07D 471/10 | (2006.01) |
| C07D 491/10 | (2006.01) |
| C07D 519/00 | (2006.01) |
| C07D 487/20 | (2006.01) |
| A61K 31/435 | (2006.01) |
| A61K 31/7056 | (2006.01) |
| A61K 38/21 | (2006.01) |

(52) U.S. Cl.
CPC ........ *A61K 31/4178* (2013.01); *A61K 31/435* (2013.01); *A61K 31/7056* (2013.01); *A61K 38/21* (2013.01); *C07D 403/12* (2013.01); *C07D 403/14* (2013.01); *C07D 471/10* (2013.01); *C07D 487/10* (2013.01); *C07D 487/20* (2013.01); *C07D 491/10* (2013.01); *C07D 491/107* (2013.01); *C07D 491/113* (2013.01); *C07D 495/10* (2013.01); *C07D 519/00* (2013.01)

(58) Field of Classification Search
CPC ............ C07D 491/107; C07D 491/113; C07D 495/10; C07D 487/10; A61K 31/4178
See application file for complete search history.

(56) References Cited

U.S. PATENT DOCUMENTS

| | | | |
|---|---|---|---|
| 889,145 | A | 5/1908 | Nientimp et al. |
| 1,879,057 | A | 9/1932 | Bray et al. |
| 3,931,207 | A | 1/1976 | Weinstock |
| 4,288,672 | A | 9/1981 | Puccini et al. |
| 4,343,975 | A | 8/1982 | Sado et al. |
| 4,493,958 | A | 1/1985 | Hamilton et al. |

(Continued)

FOREIGN PATENT DOCUMENTS

| | | |
|---|---|---|
| WO | WO 98/08850 A1 | 3/1998 |
| WO | WO 03/055474 A1 | 7/2003 |

(Continued)

OTHER PUBLICATIONS

Zhou, C., et al., "Design and Synthesis of Prolylcarboxypeptidase (PrCP) Inhibitors to Validate PrCP As a Potential Target of Obesity", Journal of Medicinal Chemistry, 2010; vol. 53, No. 19, pp. 7251-7263.

(Continued)

*Primary Examiner* — Laura L. Stockton

(57) ABSTRACT

Disclosed are compounds of Formula III. Also disclosed are salts of the compounds, pharmaceutical composition comprising the compounds or salts, and methods for treating HCV infection by administration of the compounds or salts.

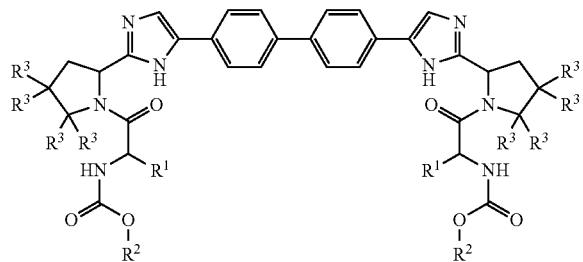

III

16 Claims, No Drawings

(56) References Cited

U.S. PATENT DOCUMENTS

| | | | |
|---|---|---|---|
| 4,776,120 A | 10/1988 | Utoh et al. | |
| 4,811,175 A | 3/1989 | DeSmet et al. | |
| 5,128,842 A | 7/1992 | Kenmochi et al. | |
| 5,408,060 A | 4/1995 | Muurinen et al. | |
| 5,432,684 A | 7/1995 | Fye et al. | |
| 5,911,317 A | 6/1999 | Tsai et al. | |
| 6,652,128 B2 | 11/2003 | Misaras et al. | |
| 6,731,913 B2 | 5/2004 | Humphreys et al. | |
| 7,335,844 B2 | 2/2008 | Lee et al. | |
| 7,600,880 B2 | 10/2009 | Cybart et al. | |
| 7,683,279 B2 | 3/2010 | Kim et al. | |
| 8,088,368 B2 | 1/2012 | Guo et al. | |
| 8,221,737 B2 | 7/2012 | Or et al. | |
| 8,273,341 B2 | 9/2012 | Guo et al. | |
| 8,344,155 B2 | 1/2013 | Chen et al. | |
| 8,492,554 B2 | 7/2013 | Chen et al. | |
| 8,575,118 B2 | 11/2013 | Guo et al. | |
| 8,653,070 B2 | 2/2014 | Qiu et al. | |
| 8,669,234 B2 | 3/2014 | Guo et al. | |
| 8,853,416 B2 | 10/2014 | Chen et al. | |
| 9,150,587 B2 * | 10/2015 | Chen | C07D 403/12 |
| 2007/0185111 A1 | 8/2007 | Cee et al. | |
| 2007/0205986 A1 | 9/2007 | Kim et al. | |
| 2008/0050336 A1 | 2/2008 | Bachand et al. | |
| 2008/0299075 A1 | 12/2008 | Bachand et al. | |
| 2009/0068140 A1 | 3/2009 | Bachand et al. | |
| 2009/0202478 A1 | 8/2009 | Bachand et al. | |
| 2009/0202483 A1 | 8/2009 | Bachand et al. | |
| 2010/0130599 A1 | 5/2010 | Coty | |
| 2010/0158862 A1 | 6/2010 | Kim et al. | |
| 2010/0215616 A1 | 8/2010 | Romine et al. | |
| 2010/0249190 A1 | 9/2010 | Lopez et al. | |
| 2010/0316607 A1 | 12/2010 | Or et al. | |
| 2011/0064698 A1 | 3/2011 | Or et al. | |
| 2011/0077280 A1 | 3/2011 | Bender et al. | |
| 2011/0112100 A1 | 5/2011 | Milbank et al. | |
| 2011/0137633 A1 | 6/2011 | Hutchins et al. | |
| 2012/0122864 A1 | 5/2012 | Zhong et al. | |
| 2013/0085150 A1 | 4/2013 | Pereira et al. | |
| 2013/0090351 A1 | 4/2013 | Das et al. | |
| 2014/0234253 A1 | 8/2014 | Walker et al. | |

FOREIGN PATENT DOCUMENTS

| | | |
|---|---|---|
| WO | WO 2005/012288 | 2/2005 |
| WO | WO 2005/061487 A1 | 7/2005 |
| WO | WO2006/077412 | 7/2006 |
| WO | WO 2008/021927 | 2/2008 |
| WO | WO 2008/021928 | 2/2008 |
| WO | WO 2008/021936 | 2/2008 |
| WO | WO 2008/064218 | 5/2008 |
| WO | WO 2008/144380 | 11/2008 |
| WO | WO 2009/020825 | 2/2009 |
| WO | WO 2009/020828 | 2/2009 |
| WO | WO 2009/102318 | 8/2009 |
| WO | WO 2009/102325 | 8/2009 |
| WO | WO 2009/102633 | 8/2009 |
| WO | WO 2009/102694 | 8/2009 |
| WO | WO 2010/017401 | 2/2010 |
| WO | WO 2010/025380 | 3/2010 |
| WO | WO 2010/042834 | 4/2010 |
| WO | WO 2010/062821 | 6/2010 |
| WO | WO 2010/065668 | 6/2010 |
| WO | WO 2010/065674 | 6/2010 |
| WO | WO 2010/065681 | 6/2010 |
| WO | WO 2010/091413 | 8/2010 |
| WO | WO 2010/096777 | 8/2010 |
| WO | WO 2010/094977 | 9/2010 |
| WO | WO 2010/096302 | 9/2010 |
| WO | WO 2010/096462 | 9/2010 |
| WO | WO 2010/099527 | 9/2010 |
| WO | WO 2010/107739 | 9/2010 |
| WO | WO 2010/111483 | 9/2010 |
| WO | WO 2010/111534 | 9/2010 |
| WO | WO 2010/111673 | 9/2010 |
| WO | WO 2010/117635 | 10/2010 |
| WO | WO 2010/117977 | 10/2010 |
| WO | WO 2010/120621 | 10/2010 |
| WO | WO 2010/120935 | 10/2010 |
| WO | WO 2010/122162 | 10/2010 |
| WO | WO 2010/132538 | 11/2010 |
| WO | WO 2010/132601 | 11/2010 |
| WO | WO 2010/138368 | 12/2010 |
| WO | WO 2010/138488 | 12/2010 |
| WO | WO 2010/138790 | 12/2010 |
| WO | WO 2010/138791 | 12/2010 |
| WO | WO 2010/144646 | 12/2010 |
| WO | WO 2010/148006 | 12/2010 |
| WO | WO 2011/004276 | 1/2011 |
| WO | WO2011/009084 | 1/2011 |
| WO | WO 2011/009084 | 1/2011 |
| WO | WO 2011/009961 | 1/2011 |
| WO | WO2011/075615 | 6/2011 |
| WO | WO 2012/135581 | 10/2012 |

OTHER PUBLICATIONS

Gao, M., et al., "Chemical Genetics Strategy Identifies an HCV NS5A Inhibitor With a Potent Clinical Effect", Nature; 2010; vol. 465; pp. 96-100.

Bell, T.W., "Drugs for Hepatitis C: Unlocking a New Mechanism of Action", ChemMedChem, 2010, vol. 5, No. 10, pp. 1663-1665.

Beaulieu, P., et al., "Inhibitors of the HCV NS5B polymerase: New Hope for the Treatment of Hepatitis C Infections", Current Opinion in Investigational Drugs, vol. 5(8), pp. 838-850 (2004).

Fried, M., et al., "Peginterferron Alfa-2a Plus Ribavirin for Chronic Hepatitis C Virus Infection", New England Journal of Medicine, vol. 347, No. 13) pp. 975-982 (Sep. 26, 2002).

Griffith, R., et al., "RCV Anti-Viral Agents", Annual Reports in Medicinal Chemistry, vol. 39, pp. 223-237 (2004).

Hoofnagle, J., "Hepatitis C: The Clinical Spectrum of Disease", Hepatology, vol. 26, No. 3 pp. 155-205 (1997).

Horsmans, Y., et al., "Isatoribine, an Agonist of TLR7, Reduces Plasma Virus Concentration in Chronic Hepatitis C Infection", Hepatology, pp. 724-731 (2005).

Moriishi, K., et al., "Mechanisms of Hepatitis C Virus Infection", Antiviral Chemistry & Chemotherapy, vol. 14,pp. 285-297 (2003).

Ni, Z-J, et a., "Progress and Development of Small Molecular HCV Antivirals", Current Opinion in Drug Discovery & Development, vol. 7(4), pp. 446-459 (2004).

Szabo, E., et al., "Viral Hepatitis: New Data on Hepatitis C Infection", Pathology Oncology Research, vol. 9, No. 4, pp. 215-221 (2003).

Thomson, B., et al., "Hepatitis C Virus Infection", Clinical Microbiology and Infection, vol. 11, No. 2, (2005).

Watashi, K, et al., "Cyclophilin B Is Functional Regulator of Hepatitis C Virus RNA Polymerase", Molecular Cell, vol. 19, pp. 111-122 (2005).

Gupta, K., et al., "Favorable preclinical profile of IDX21437, a novel uridine nucleotide prodrug, for use in a directacting antiviral (DAA) regimen for HCV" J Hepatology, vol. 60 S504 (2014), poster P1244.

Kim, B. Moon, et al., "Thiophene Derivatives as Extremely High Affinity P3', Ligands for the Hydroxyethylpiperazine Class of HIV-1 Protease Inhibitors", Bioorganic & Medicinal Chemistry Letters, 1995, 5(2) pp. 185-190.

Lawitz, E., et al., "A phase II study of samatasvir (IDX719) in combination with simeprevir and ribavirin in treatmentnaïve HCV-infected subjects with genotypes 1B and 4 (helix-1 study)" J Hepatology, vol. 60 S495 (2014), poster P1222.

Zhou, X.J. et al., "Pharmacokinetic drug-drug interaction between samatasvir (IDX719), a pan-genotypic NS5A inhibitor, and simeprevir in healthy volunteers and HCV-infected subjects" J Hepatology, vol. 60 S495 (2014), poster P1221.

Krieger et al "Enhancement of Hepatitis C Virus RNA Replication by Cell Culture-Adaptive Mutations" Journal of Virology 2001 vol. 75(10) pp. 4614-4624.

Stahl et al "Handbook of Pharmaceutical Salts, Properties, Selection and Use" 2002 P. Heinrich Stahl Camille G. Wermuth Eds.

(56) References Cited

OTHER PUBLICATIONS

Extended European Search Report for EP Application No. 10814293 6 dated Jan. 15, 2013.
International Search Report for International Application No. PCT/US2010/046782 dated Oct. 15, 2010.

* cited by examiner

CHEMICAL COMPOUNDS

CROSS-REFERENCE TO RELATED APPLICATIONS

This application is filed as a continuation application of U.S. Ser. No. 14/849,190, filed on Sep. 9, 2015, which is a continuation application of U.S. Ser. No. 14/472,293, filed on Aug. 28, 2014 (now U.S. Pat. No. 9,150,587), which is a continuation application of U.S. Ser. No. 13/915,674, filed on Jun. 12, 2013 (now U.S. Pat. No. 8,853,416), which is a continuation application of U.S. Ser. No. 13/677,358, filed on Nov. 15, 2012 (now U.S. Pat. No. 8,492,554), which is a continuation application of U.S. Ser. No. 12/936,545, filed Oct. 6, 2010 (now U.S. Pat. No. 8,344,155), which is a National Phase Application of International Application No. PCT/US2010/046782 filed on Aug. 26, 2010, which claims priority from 61/239,855 filed on Sep. 4, 2009, 61/297,324 filed on Jan. 22, 2010 and 61/348,767 filed on May 27, 2010 in the United States, all of which are incorporated by reference herein in their entireties.

FIELD OF THE INVENTION

The present disclosure relates to antiviral compounds. In particular, the present disclosure relates to compounds useful for the treatment of hepatitis C virus (HCV) infection, crystalline salts of the compounds, pharmaceutical compositions comprising the compounds, and methods for treating HCV infection.

BACKGROUND OF THE INVENTION

Chronic infection with HCV is a major health problem associated with liver cirrhosis, hepatocellular carcinoma and liver failure. An estimated 170 million chronic carriers worldwide are at risk of developing liver disease. See, for example, Szabo, et al., *Pathol. Oncol. Res.* 2003, 9:215-221, and Hoofnagle J H, *Hepatology* 1997, 26:15S-20S. In the United States alone 2.7 million are chronically infected with HCV, and the number of HCV-related deaths in 2000 was estimated between 8,000 and 10,000, a number that is expected to increase significantly over the next years. Infection by HCV is insidious in a high proportion of chronically infected (and infectious) carriers who may not experience clinical symptoms for many years. Liver cirrhosis can ultimately lead to liver failure. Liver failure resulting from chronic HCV infection is now recognized as a leading cause of liver transplantation.

HCV is a member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Because the replicative cycle of HCV does not involve any DNA intermediate and the virus is not integrated into the host genome, HCV infection can theoretically be cured. While the pathology of HCV infection affects mainly the liver, the virus is found in other cell types in the body including peripheral blood lymphocytes. See, for example, Thomson B J and Finch R G, *Clin Microbial Infect.* 2005, 11:86-94, and Moriishi K and Matsuura Y, *Antivir. Chem. Chemother.* 2003, 14:285-297.

At present, the standard treatment for chronic HCV is interferon alpha (IFN-alpha) in combination with ribavirin and this requires at least six (6) months of treatment. IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of pegylated IFN-alpha plus ribavirin. However, a number of patients still have significant side effects, primarily related to ribavirin. Ribavirin causes significant hemolysis in 10-20% of patients treated at currently recommended doses, and the drug is both teratogenic and embryotoxic. Even with recent improvements, a substantial fraction of patients do not respond with a sustained reduction in viral load and there is a clear need for more effective antiviral therapy of HCV infection. See, for example, Fried, et al. *N. Engl. J Med* 2002, 347:975-982.

A number of approaches are being pursued to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4A protease/helicase and the NS5b RNA-dependent RNA polymerase are considered the most promising viral targets for new drugs. See, for example, Ni, Z. J. and Wagman, A. S. *Curr. Opin. Drug Discov. Devel.* 2004, 7, 446-459, Beaulieu, P. L. and Tsantrizos, Y. S. *Curr. Opin. Investig. Drugs* 2004, 5, 838-850, and Griffith, et al., *Ann. Rep. Med. Chem* 39, 223-237, 2004.

Besides targeting viral genes and their transcription and translation products, antiviral activity can also be achieved by targeting host cell proteins that are necessary for viral replication. For example, Watashi, et al, Molecular Cell, 19, 111-122, 2005, show how antiviral activity can be achieved by inhibiting host cell cyclophilins. Alternatively, a potent TLR7 agonist has been shown to reduce HCV plasma levels in humans. See, Horsmans, et al, Hepatology, 42, 724-731, 2005.

Compounds said to be useful for treating HCV infection are disclosed, for example, in WO 2008/064218 (Leivers et. al), WO 2008/244380 (Bachand et. al), and US 2009/0068140 (Bachand et. al). These references also disclose methods for preparing the compounds, compositions comprising the compounds, pharmaceutical compositions comprising the compounds and additional compounds, methods of treating HCV, salts of the compounds, routes of administration, and other information regarding how to make, formulate, and use the compounds.

SUMMARY OF THE INVENTION

Briefly, in one aspect, the present invention discloses compounds of Formula I;

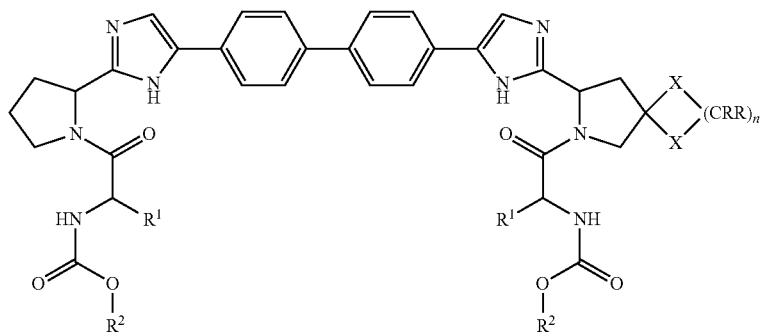

I wherein each $R^1$ is independently H or $C_{1-3}$alkyl;
each $R^2$ is independently $C_{1-3}$alkyl;
each X is independently CRR, O, or S;
n is 2 or 3; and
each R is independently methyl, hydrogen, or deuterium.

In another aspect, the present invention discloses compounds of Formula II;

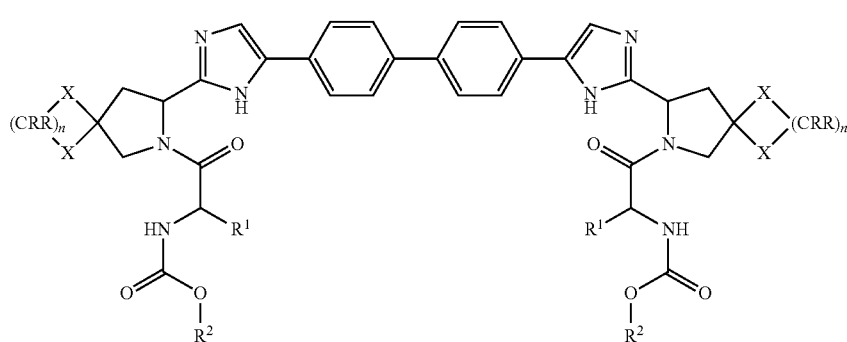

II wherein each $R^1$ is independently H or $C_{1-3}$alkyl;
each $R^2$ is independently $C_{1-3}$alkyl;
each X is independently CRR, O, or S;
each n is independently 2 or 3; and
each R is independently methyl, hydrogen, or deuterium.

In another aspect, the present invention discloses compounds of Formula III;

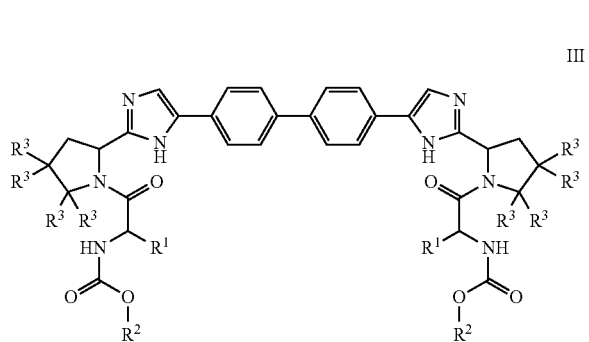

III wherein each $R^1$ is independently H or $C_{1-3}$alkyl;
each $R^2$ is independently $C_{1-3}$alkyl;
on each carbon to which there are $R^3$ groups, either both $R^3$s are H or the $R^3$ groups together with the carbon to which they are bonded form a 4-, 5-, or 6-membered saturated spiro ring with the proviso that there is no more than 1 spiro ring on each saturated nitrogen-containing ring;

each saturated spiro formed from $R^3$ groups is independently cycloalkyl, or may contain 1 or 2 oxygen atoms, or 1 or 2 sulfur atoms, or 1 $SO_2$, or 1 $NR^4$;

each $R^4$ is independently H, $C(O)OC_{1-4}$alkyl, $C(O)C_{1-4}$alkyl, $C(O)NC_{1-4}$alkyl, or $SO_2C_{1-4}$alkyl;
each spiro ring may optionally be substituted with deuterium, fluorine, or 1 or 2 methyl groups.

In another aspect, the present invention discloses pharmaceutically acceptable salts of the compounds of Formula I, II, or III.

In another aspect, the present invention discloses pharmaceutical compositions comprising a compound of Formula I, II, or III, or a pharmaceutically acceptable salt thereof.

In another aspect, the present invention discloses a method for treating a viral infection, for example infection with HCV, in a human, comprising administration of a pharmaceutical composition of the invention.

DETAILED DESCRIPTION OF THE INVENTION

In the above Formulas I, II, and III, except for when $R^1$ is hydrogen, the carbon to which $R^1$ is attached is chiral. In addition, the depicted tertiary carbon in each of the two depicted nitrogen containing 5-membered saturated heterocyclic rings is also chiral. Therefore, the compounds contain at least two chiral carbon atoms and when each $R^1$ is $C_{1-3}$ alkyl, the compounds contain at least 4 chiral carbon atoms. Therefore, the compounds can exist in various enantiomeric mixtures.

In an embodiment of the invention, the compounds of Formula I, II, or III, or pharmaceutically acceptable salts thereof, are enantiomerically enriched with the enantiomer wherein all of the chiral carbons referred to in the previous paragraph are in the S configuration. In general, reference to an enantiomerically enriched compound or salt, is meant to indicate that the specified enantiomer will comprise more than 50% by weight of the total weight of all enantiomers of the compound or salt. An example of a compound with four chiral carbons in S configuration is illustrated below.

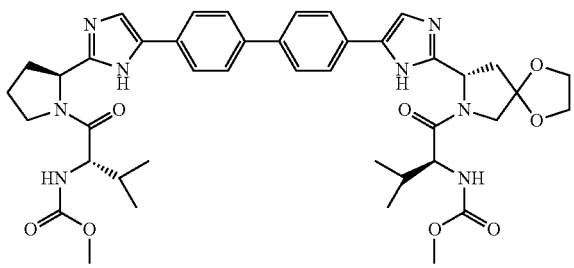 [SMILES: COC(=O)N[C@H](C(=O)N1CCC[C@H]1c1ncc(-c2ccc(-c3ccc(-c4cnc([C@@H]5CC6(CN5C(=O)[C@@H](NC(=O)OC)C(C)C)OCCO6)[nH]4)cc3)cc2)[nH]1)C(C)C]

In an embodiment of the invention, each X is identical.

In an embodiment of the invention, either all Rs are H or all Rs are deuterium (D). In other words, in an embodiment of the invention, either every CRR group in the spiro is $CH_2$ or every CRR group in the spiro is $CD_2$. Deuterium is naturally present in very small amounts in hydrogen compounds. By designating a substituent as deuterium or D, applicants mean that the natural isotopic amount of deuterium has been increased so that more that half of that particular substituent is D as compared to H.

In an embodiment of the invention, no more than 2 Rs are methyl.

In an embodiment of the invention, in compounds of Formula III, when $R^3$ groups form a spiro ring on each saturated nitrogen-containing ring, each of said spiro groups is bonded to the same relative carbon atom in each saturated nitrogen containing ring.

Pharmaceutically acceptable salts can be prepared by methods well known in the art. Suitable salts include those described, for example, in P. Heinrich Stahl, Camille G. Wermuth (eds.), handbook of Pharmaceutical Salts properties, selection, and Use; 2002. See also, WO 2009/020828 (Kimet. AI), which describes the preparation of crystalline salts of certain anti-viral compounds. Preferred salts include HCl salts, for example a di-HCl salt, and sulphate salts.

The compounds and salts of the invention may be used alone or in combination with one or more other therapeutic agents. In one aspect the further therapeutic agent is selected from Standard of Care therapies such as interferon/ribavarin, small molecule HCV replication inhibitors (more commonly referred to as direct acting antivirals. Suitable combination therapies are described, for example in WO 2008/064218 (Leivers et. al), WO 2008/244380 (Bachand et. al), and US 2009/0068140 (Bachand et. al). These references also contain significant disclosure regarding routes of administration, and other information regarding how to make, formulate, and use the compounds.

EXAMPLES

A table of abbreviations used in this Experimental section is set forth below.

| | |
|---|---|
| DCM | Dichloromethane |
| DMF | N,N-dimethylformamide |
| HATU | (O-7-azabenzotriazol-1-yl)-N,N,N',N'-tetramethyluronium hexafluorophosphate) |
| ES LC-MS | Electrospray Liquid Chromatography Mass Spectrometry |
| THF | Tetrahydrofuran |
| DIEA | diisopropylethylamine |
| DMSO | dimethylsulfoxide |
| DME | dimethoxyethane |
| TEA | Triethylamine |
| Pd(dppf)Cl$_2$ | 1,1'-Bis(diphenylphosphino)ferrocene-palladium(II)dichloride dichloromethane complex |
| Dess-Martin | Dess-Martin periodinane |
| HRMS | High Resolution Mass Spectroscopy |

Intermediate 1: methyl {(1S)-1-[((2S)-2-{4-[4'-(aminoacetyl)-4-biphenylyl]-1H-imidazol-2-yl}-1-pyrrolidinyl)carbonyl]-2-methylpropyl}carbamate

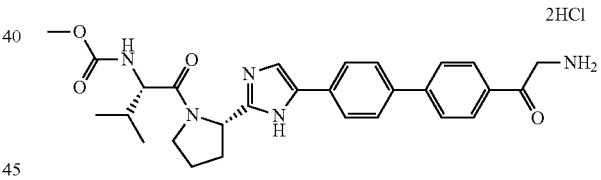

Intermediate 1 can be prepared as illustrated by the reaction scheme below.

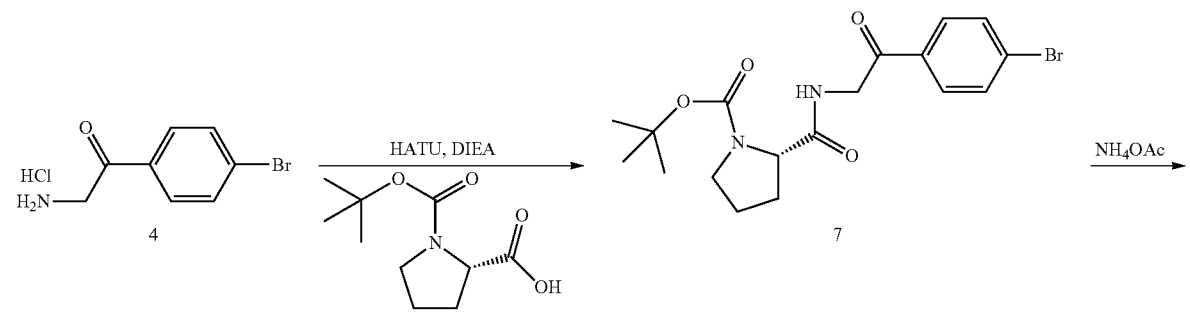

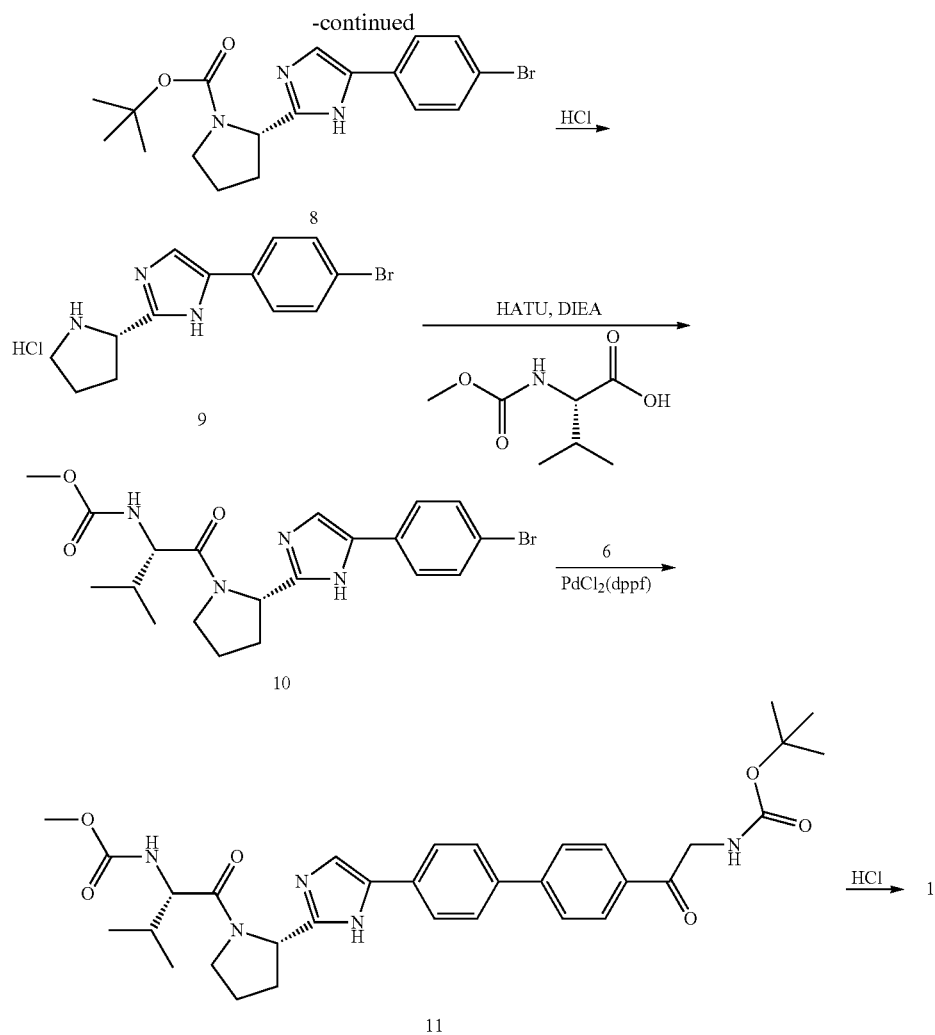

A solution of 1,1-dimethylethyl[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]carbamate (Intermediate 11) (3.8 g, 6.3 mmol) in DCM (40 mL) was treated with HCl (10 mL, 4M in dioxane) to give methyl {(1S)-1-[((2S)-2-{4-[4'-(aminoacetyl)-4-biphenylyl]-1H-imidazol-2-yl}-1-pyrrolidinyl)carbonyl]-2-methylpropyl}carbamate (Intermediate 1) as light yellow solid (3.5 g, quant.).

Intermediate 2: (3S,7S,9S)-7,9-dimethyl-2-{N-[(methyloxy)carbonyl]-L-valyl}-6,10-dioxa-2-azaspiro[4.5]decane-3-carboxylic acid

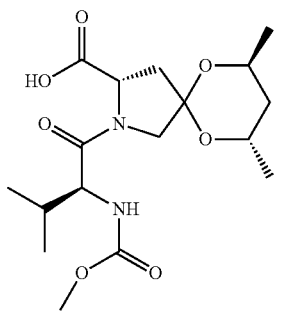

Intermediate 2 can be prepared as illustrated in the reaction scheme below.

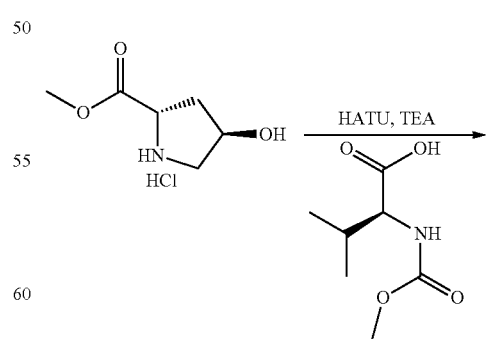

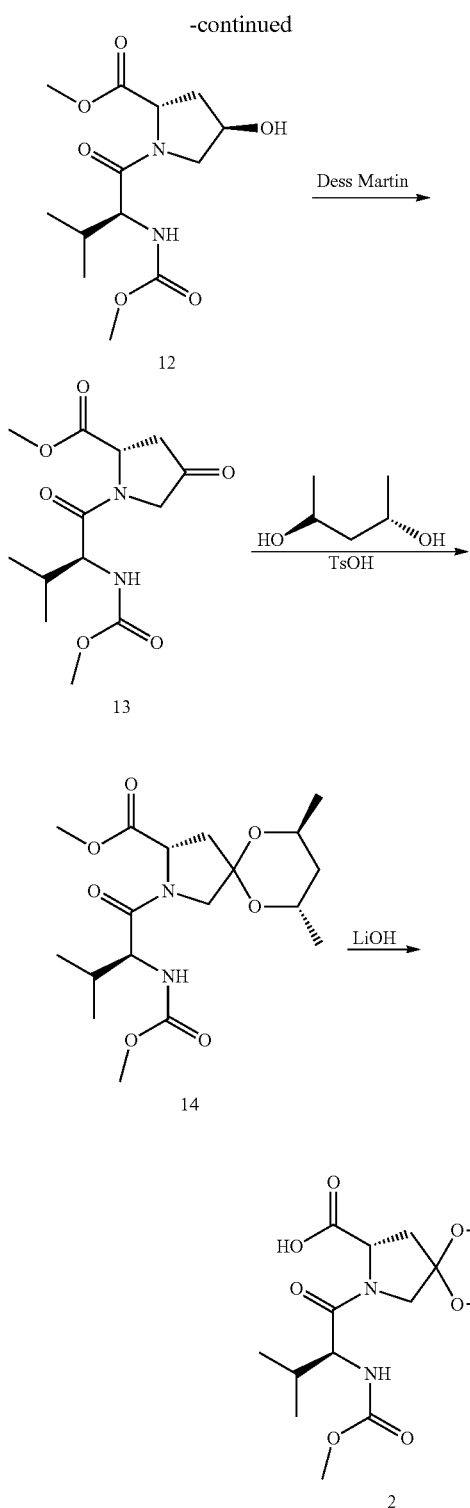

To a stirred solution of methyl (3S,7S,9S)-7,9-dimethyl-2-{N-[(methyloxy)carbonyl]-L-valyl}-6,10-dioxa-2-azaspiro[4.5]decane-3-carboxylate (Intermediate 14) (360 mg, 0.932 mmol) in a mixed solvents of THF (4 mL), t-butanol (1 mL) and water (1 mL) was added LiOH (44 mg, 1.86 mmol). The resulting mixture was stirred for 2 hrs at rt before acidified with 1N HCl to pH~3 and further diluted with ethyl acetate (100 mL). The solution was washed with brine. The organic layer was dried over Na₂SO₄, filtered and evaporated to give (3S,7S,9S)-7,9-dimethyl-2-{N-[(methyloxy)carbonyl]-L-valyl}-6,10-dioxa-2-azaspiro[4.5]decane-3-carboxylic acid (Intermediate 2) (315 mg, yield: 91%) as solid. ES LC-MS m/z=373 (M+H)⁺.

Intermediate 4:
2-amino-1-(4-bromophenyl)ethanone

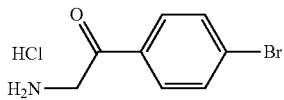

To a stirred solution of 2-bromo-1-(4-bromophenyl)ethanone (130 g 0.478 mol) in toluene (2500 mL) was added hexamethylenetetramine (65.6 g 0.478 mol). The mixture was stirred at 40° C. for 16 hrs. The resulting solid was filtered off and washed with toluene and ether to give a white solid. To a stirred suspension of this white solid in ethanol (800 mL) was added concentrated hydrochloride acid (300 mL). The mixture was stirred at ambient temperature for 20 hrs. The solid was collected by filtration and washed with ethanol and water and dried in vacuo to give 2-amino-1-(4-bromophenyl)ethanone (4) (95 g, yield: 92%) as a white solid, which was used without purification for the next step. ¹H NMR (300 MHz, DMSO-d₆) δ ppm 8.58 (s, br, 2H), 7.96 (d, J=8.7 Hz, 2H), 7.81 (d, J=8.7 Hz, 2H), 4.48-4.52 (m, 2H). ES LC-MS m/z=214, 216 (M+H)⁺.

Intermediate 5: 1,1-dimethylethyl
[2-(4-bromophenyl)-2-oxoethyl]carbamate

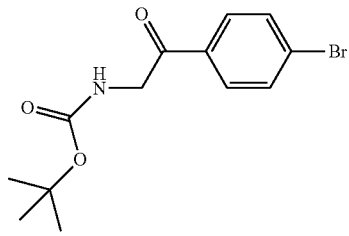 [SMILES: CC(C)(C)OC(=O)NCC(=O)c1ccc(Br)cc1]

To a mixture of 2-amino-1-(4-bromophenyl)ethanone hydrochloride (Intermediate 4) (50 g, 0.2 mol), Boc₂O (48 g, 0.22 mol) in DCM (1000 mL) was added TEA (68.8 mL, 0.5 mol) dropwise at 0° C. After addition, the resulting mixture was stirred at ambient temperature overnight and was filtered. The filtration was washed with 1 N HCl (300 mL×3) and brine, dried over Na₂SO₄, concentrated in vacuo to give an off-white solid, which was further washed with petroleum ether to afford 1,1-dimethylethyl [2-(4-bromophenyl)-2-oxoethyl]carbamate (Intermediate 5) (40 g, yield: 64%). ¹H NMR (300 MHz, CDCl3) δ ppm 7.83 (d, J=8.7 Hz, 2H), 7.65 (d, J=8.7 Hz, 2H), 5.48 (s, br, 1H), 4.60-4.62 (m, 2H), 1.49 (s, 9H). ES LC-MS m/z=336 (M+Na)⁺.

Intermediate 6: 1,1-dimethylethyl{2-oxo-2-[4-(4,4,5,5-tetramethyl-1,3,2-dioxaborolan-2-yl)phenyl]ethyl}carbamate

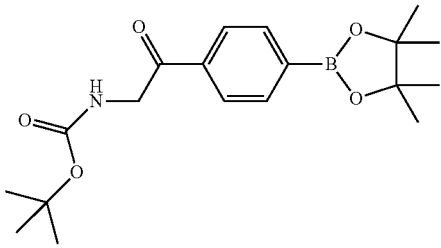 [SMILES: CC(C)(C)OC(=O)NCC(=O)c1ccc(B2OC(C)(C)C(C)(C)O2)cc1]

Intermediate 6 can be prepared as illustrated in the reaction scheme below.

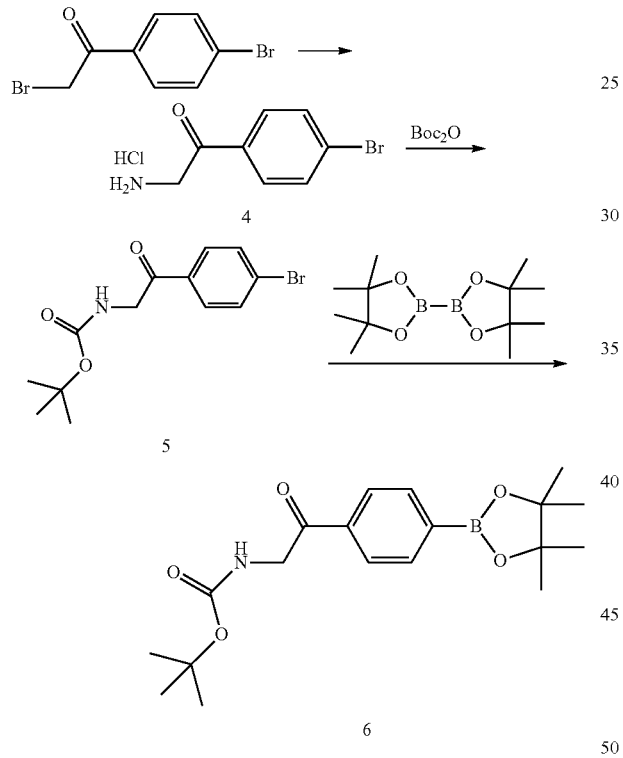

Pd(dppf)Cl$_2$ (2.6 g 3.18 mmol) was added to a mixture of 1,1-dimethylethyl[2-(4-bromophenyl)-2-oxoethyl]carbamate (Intermediate 5) (20 g, 63.7 mmol), bis(pinacolato)diboron (19.4 g, 76.4 mmol) and KOAc (24.8 g, 0.254 mol) in dioxane (300 mL), the flask was purged with nitrogen (3×) and heated to 80° C. for 16 hrs under nitrogen atmosphere. The reaction mixture was diluted with hexane (300 mL), filtered, concentrated and the residue was purified by chromatography on silica gel (petroleum ether/ethyl acetate=5/1) to give 1,1-dimethylethyl{2-oxo-2-[4-(4,4,5,5-tetramethyl-1,3,2-dioxaborolan-2-yl)phenyl]ethyl}carbamate (Intermediate 6) (13.3 g, yield: 58%) as a white solid. $^1$H NMR (300 MHz, CDCl3) δ ppm 7.90-7.93 (m, 4H), 5.55 (s, br, 1H), 4.68 (s, 2H), 1.48 (s, 9H), 1.35 (s, 12H). ES LC-MS m/z=384 (M+Na)$^+$.

Intermediate 7: 1,1-dimethylethyl(2S)-2-({[2-(4-bromophenyl)-2-oxoethyl]amino}carbonyl)-1-pyrrolidinecarboxylate

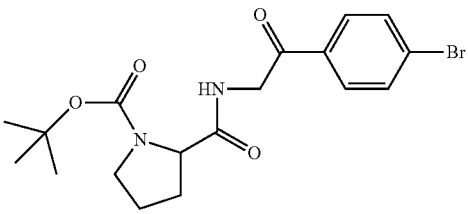 [SMILES: CC(C)(C)OC(=O)N1CCCC1C(=O)NCC(=O)c1ccc(Br)cc1]

A mixture of 1-{[(1,1-dimethylethyl)oxy]carbonyl}-L-proline (50 g, 0.233 mol), HATU (106 g, 0.279 mol) and DIEA (150 mL) in DMF (400 mL) was stirred at ambient temperature for 10 min. 2-Amino-1-(4-bromophenyl)ethanone hydrochloride (Intermediate 4) (70 g, 0.279 mol) in DMF (500 mL) was added and the resulting mixture was stirred overnight before diluted with EtOAc (4 L). The solution was washed with 1N HCl (500 mL×4) and brine, dried over Na$_2$SO$_4$, concentrated. The crude product was recrystallized from a mixture of petroleum ether/ethyl acetate (2/1) to give 1,1-dimethylethyl(2S)-2-({[2-(4-bromophenyl)-2-oxoethyl]amino}carbonyl)-1-pyrrolidinecarboxylate (Intermediate 7) (58.4 g, yield: 61%) as yellow solid. $^1$H NMR (300 MHz, DMSO) δ ppm 8.22 (s, 1H), 7.93 (d, J=8.4 Hz, 2H), 7.77 (d, J=8.4 Hz, 2H), 4.46-4.51 (m, 2H), 4.15-4.21 (m, 1H), 3.28-3.40 (m, 2H), 1.78-1.90 (m, 4H), 1.29-1.41 (m, 9H). ES LC-MS m/z=411.1, 4113.1 (M+H)$^+$.

Intermediate 8: 1,1-dimethylethyl(2S)-2-[4-(4-bromophenyl)-1H-imidazol-2-yl]-1-pyrrolidinecarboxylate

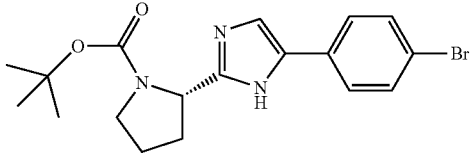 [SMILES: CC(C)(C)OC(=O)N1CCC[C@H]1c1ncc(-c2ccc(Br)cc2)[nH]1]

A mixture of 1,1-dimethylethyl(2S)-2-({[2-(4-bromophenyl)-2-oxoethyl]amino}carbonyl)-1-pyrrolidinecarboxylate (7) (40.0 g, 97.2 mmol) and NH$_4$OAc (60 g, 0.778 mol) in xylene (400 mL) was heated to 150° C. for 5 hrs in a sealed reactor. The reaction mixture was concentrated, and the residue was dissolved in EtOAc (500 mL) and washed with aqueous NaHCO$_3$ and brine. The organic phase was dried over Na$_2$SO$_4$, concentrated to dryness. The crude product was purified by chromatography on silica gel (petroleum ether/ethyl acetate=1/1) to give 1,1-dimethylethyl(2S)-2-[4-(4-bromophenyl)-1H-imidazol-2-yl]-1-pyrrolidinecarboxylate (Intermediate 8) (34 g, yield: 89%) as brown solid. $^1$H NMR (300 MHz, CDCl$_3$) δ ppm 7.52 (d, J=8.4 Hz, 2H), 7.46 (d, J=8.4 Hz, 2H), 7.20 (s, 1H), 5.58-5.71 (m, 1H), 3.38-3.42 (m, 1H), 2.80-2.87 (m, 2H), 2.03-2.06 (m, 2H), 1.88-2.00 (m, 2H), 1.49 (s, 9H). ES LC-MS m/z=392, 394 (M+H)$^+$.

Intermediate 9: 4-(4-bromophenyl)-2-[(2S)-2-pyrrolidinyl]-1H-imidazole

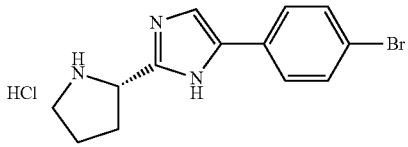 [SMILES: Cl ; Brc1ccc(-c2cnc([C@@H]3CCCN3)[nH]2)cc1]

1,1-dimethylethyl(2S)-2-[4-(4-bromophenyl)-1H-imidazol-2-yl]-1-pyrrolidinecarboxylate (Intermediate 8) (72.4 g, 185 mmol) was treated with saturated HCl in dioxane (200 mL), and stirred at ambient temperature overnight. The resulting solid was filtered and washed with petroleum ether to give 4-(4-bromophenyl)-2-[(2S)-2-pyrrolidinyl]-1H-imidazole (Intermediate 9) (60 g, yield: 90%) as yellow solid. $^1$H NMR (300 MHz, DMSO-d$_6$) δ ppm 8.10 (s, 2H), 7.88 (d, J=6.6 Hz, 2H), 7.70 (d, J=6.6 Hz, 2H), 7.49 (s, 1H), 7.32 (s, 1H), 7.16 (s, 1H), 4.50-4.52 (m, 1H), 3.15-3.40 (m, 2H), 1.88-2.88 (m, 4H). ES LC-MS m/z=291.1, 293.1 (M+H)$^+$.

Intermediate 10: methyl [(1S)-1-({(2S)-2-[4-(4-bromophenyl)-1H-imidazol-2-yl]-1-pyrrolidinyl}carbonyl)-2-methylpropyl]carbamate

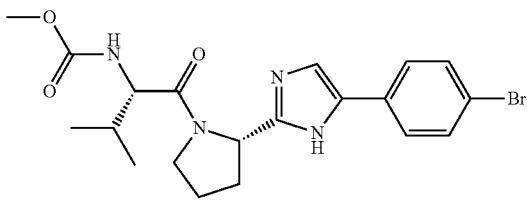 [SMILES: COC(=O)N[C@H](C(=O)N1CCC[C@H]1c1ncc(-c2ccc(Br)cc2)[nH]1)C(C)C]

N-[(methyloxy)carbonyl]-L-valine (43.1 g, 0.246 mol) and HATU (93.5 g, 0.246 mol) in DCM (1000 mL) was stirred for 10 min. 4-(4-Bromophenyl)-2-[(2S)-2-pyrrolidinyl]-1H-imidazole (Intermediate 9) (60 g, 0.205 mol) was introduced, followed by DIEA (82.6 mL, 0.308 mol) dropwise. The mixture was stirred at ambient temperature overnight before diluted with DCM (1000 mL) and washed with aqueous NaHCO$_3$ and brine. The organic phase was dried over Na$_2$SO$_4$, concentrated to dryness. The crude product was purified by chromatography on silica gel (petroleum ether/ethyl acetate=1/1) to give methyl [(1S)-1-({(2S)-2-[4-(4-bromophenyl)-1H-imidazol-2-yl]-1-pyrrolidinyl}carbonyl)-2-methylpropyl]carbamate (Intermediate 10) (62 g, yield: 67%) as yellow solid. $^1$H NMR (300 MHz, CDCl3) δ: 7.43-7.51 (m, 4H), 7.17 (s, 1H), 5.53-5.57 (m, 1H), 5.20-5.22 (m, 1H), 5.29-5.33 (m, 1H), 3.64-3.71 (m, 5H), 2.99-3.03 (m, 1H), 1.88-2.31 (m, 4H), 0.88-0.92 (m, 6H). ES LC-MS m/z=449, 451 (M+H)$^+$.

Intermediate 11: 1,1-dimethylethyl[2-(4'{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]carbamate

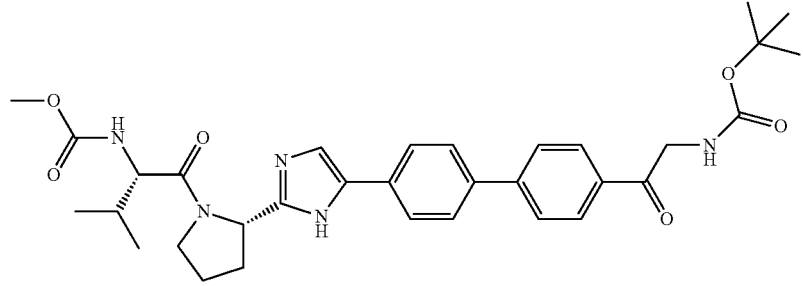 [SMILES: COC(=O)N[C@H](C(=O)N1CCC[C@H]1c1ncc(-c2ccc(-c3ccc(C(=O)CNC(=O)OC(C)(C)C)cc3)cc2)[nH]1)C(C)C]

To a mixture of methyl [(1S)-1-({(2S)-2-[4-(4-bromophenyl)-1H-imidazol-2-yl]-1-pyrrolidinyl}carbonyl)-2-methylpropyl]carbamate (Intermediate 10) (62 g, 0.138 mol), 1,1-dimethylethyl{2-oxo-2-[4-(4,4,5,5-tetramethyl-1,3,2-dioxaborolan-2-yl)phenyl]ethyl}carbamate (Intermediate 6) (47.7 g, 0.152 mol) and NaHCO$_3$ (34.2 g, 0.414 mol) in a mixed DME (800 mL) and water (260 mL) was added Pd(dppf)Cl$_2$ (5.63 g, 6.9 mmol). The flask was purged with nitrogen (3×) before heated to 80° C. for 16 hrs. The reaction was cooled down to rt and filtered. The filtrate was diluted with EtOAc (1000 mL), and the solution was washed with aqueous NaHCO$_3$ and brine, dried over Na$_2$SO$_4$, concentrated. The residue was purified by chromatography on silica gel (petroleum ether/ethyl acetate=1/2) to give 1,1-dimethylethyl[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]carbamate (Intermediate 11) (45 g, yield: 54%) as yellow solid. $^1$H NMR (300 MHz, CDCl3) δ ppm 8.03 (d, J=8.4 Hz, 2H), 7.88-760 (m, 6H), 5.58 (S, br, 1H), 5.42 (m, 1H), 5.28-5.30 (m, 1H), 4.71 (s, 2H), 4.32-4.35 (m, 1H), 3.70-3.84 (m, 5H), 2.96 (s, br, 1H), 1.96-2.11 (m, 4H), 1.49 (s, 9H), 0.88-0.92 (m, 6H). ES LC-MS m/z=604, (M+H)$^+$;

Intermediate 12: methyl N-[(methyloxy)carbonyl]-L-valyl-(4R)-4-hydroxy-L-prolinate

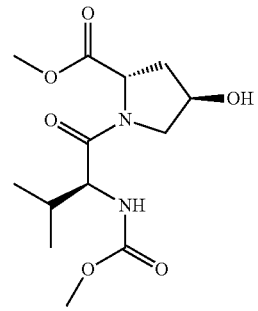 [SMILES: COC(=O)N[C@H](C(=O)N1C[C@H](O)C[C@H]1C(=O)OC)C(C)C]

To a stirred solution of N-[(methyloxy)carbonyl]-L-valine (2.89 g, 16.52 mmol) in DCM were added TEA (3.51 g, 34.7 mmol) and HATU (3 g, 16.52 mmol). After approximately 10 min stirring, methyl (4R)-4-hydroxy-L-prolinate hydrochloride (3 g, 16.52 mmol) was introduced. The resulting mixture was stirred for additional 4 hrs at rt before quenched with NaHCO$_3$ (ss). The layers were separated and the aqueous layer was extracted with DCM (2×). The combined organic phase was dried over Na$_2$SO$_4$, filtered and concentrated. The crude product was purified by column chromatography (silica gel, 0 to 70% ethyl acetate in hexane) to give methyl N-[(methyloxy)carbonyl]-L-valyl-(4R)-4-hydroxy-L-prolinate (Intermediate 12) (3.5 g, yield: 70%). $^1$H NMR (400 MHz, CHLOROFORM-d) δ ppm 5.34-5.54 (m, 1H) 4.69 (t, J=8.41 Hz, 1H) 4.55 (br. s., 1H) 4.21 (s, 1H)

3.92-4.08 (m, 1H) 3.74 (s, 4H) 3.66 (s, 3H) 2.29-2.50 (m, 1H) 1.92-2.19 (m, 2H) 0.86-1.13 (m, 6H). ES LC-MS m/z=303.5 (M+H)⁺.

Intermediate 13: methyl N-[(methyloxy)carbonyl]-L-valyl-4-oxo-L-prolinate

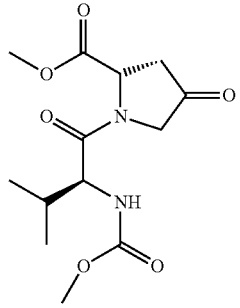

To a stirred solution of N-[(methyloxy)carbonyl]-L-valyl-(4R)-4-hydroxy-L-prolinate (Intermediate 12) (3.5 g, 11.9 mmol) in DCM (80 mL) was added Dess-Martin (10 g) at rt The resulting mixture was stirred for additional 4 hours before quenched with 5% aq. sodium thiosulfate (350 mL) and then sat. NaHCO₃ (200 mL). Stirred was continued for 10 min and the mixture was extracted with DCM (2×300 mL). The organic layer was dried over MgSO₄, filtered and concentrated. The crude product was purified by column chromatography (silica gel, 0 to 70% ethyl acetate in hexane) to give methyl N-[(methyloxy)carbonyl]-L-valyl-4-oxo-L-prolinate (Intermediate 13) (701 mg, yield: 20%).

¹H NMR (400 MHz, CHLOROFORM-d) δ ppm 5.25 (d, J=9.18 Hz, 1H) 5.07 (dd, J=10.74, 2.93 Hz, 1H) 4.36 (d, J=17.77 Hz, 1H) 3.97-4.23 (m, 2H) 3.69-3.77 (m, 3H) 3.63 (s, 3H) 2.92 (dd, J=18.94, 10.74 Hz, 1H) 2.62 (dd, J=18.94, 2.73 Hz, 1H) 2.01 (t, J=3.32 Hz, 1H) 0.86-1.16 (m, 6H).

Intermediate 14: methyl(3S,7S,9S)-7,9-dimethyl-2-{N-[(methyloxy)carbonyl]-L-valyl}-6,10-dioxa-2 azaspiro[4.5]decane-3-carboxylate

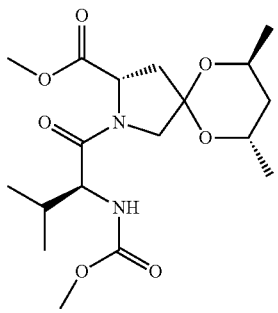

Methyl N-[(methyloxy)carbonyl]-L-valyl-4-oxo-L-prolinate (Intermediate 13) (650 mg, 2.164 mmol), (2S,4S)-2,4-pentanediol (902 mg, 8.66 mmol) and TsOH (82 mg, 0.43 mmol) were heated to reflux in toluene (40 mL) with Dean Stark trap overnight. After cooled down to rt and diluted with ethyl acetate, the resulting solution was washed with NaHCO₃ (ss) and brine. The organic later was dried over MgSO4, filtered and evaporated. The crude product was purified by column chromatography (silica gel, 0 to 50% ethyl acetate in hexane) to give methyl (3S,7S,9S)-7,9-dimethyl-2-{N-[(methyloxy)carbonyl]-L-valyl}-6,10-dioxa-2-azaspiro[4.5]decane-3-carboxylate (Intermediate 14) (366 mg, yield: 44%) as an oil. ¹H NMR (400 MHz, CHLOROFORM-d) δ ppm 5.38-5.51 (m, 1H) 4.54 (t, J=8.03 Hz, 1H) 4.25-4.36 (m, 1H) 3.91-4.05 (m, 2H) 3.85 (d, J=10.04 Hz, 1H) 3.54-3.77 (m, 6H) 2.46-2.53 (m, 1H) 2.12 (dd, J=12.92, 7.65 Hz, 1H) 2.00-2.06 (m, 1H) 1.54-1.75 (m, 3H) 1.10-1.25 (m, 6H) 1.03 (d, J=6.78 Hz, 3H) 0.84-0.96 (m, 3H). ES LC-MS m/z=409.3 (M+Na)⁺.

Intermediates 15 and 17 were prepared using procedures similar to the procedures outlined in the preparation of Intermediate 2:

Intermediate 15: (3S,7R,9R)-7,9-dimethyl-2-{N-[(methyloxy)carbonyl]-L-valyl}-6,10-dioxa-2-azaspiro[4.5]decane-3-carboxylic acid

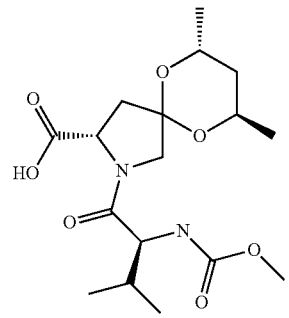 [SMILES: COC(=O)N[C@H](C(=O)N1CC2(C[C@H]1C(=O)O)O[C@H](C)C[C@@H](C)O2)C(C)C]

¹H NMR (400 MHz, DMSO-d₆) δ ppm 12.53 (br. s., 1H), 7.49 (d, 1H), 4.34 (d, 1H), 4.24 (t, 1H), 4.06 (br. m, 2H), 3.93 (t, 1H), 3.37 (m, 4H), 2.35 (m, 1H), 2.09-1.86 (br. m, 2H), 1.59 (m, 2H), 1.17 (m, 6H), 0.91 (m, 6H).

Intermediate 16: methyl(8S)-7-{N-[(methyloxy)carbonyl]-L-valyl}-1,4-dioxa-7-azaspiro[4.4]nonane-8-carboxylate

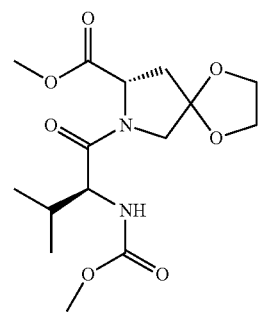 [SMILES: COC(=O)N[C@H](C(=O)N1CC2(C[C@H]1C(=O)OC)OCCO2)C(C)C]

ES LC-MS m/z=345.3 (M+H)⁺.

Intermediate 17: (8S)-7-{N-[(methyloxy)carbonyl]-L-valyl}-1,4-dioxa-7-azaspiro[4.4]nonane-8-carboxylic acid

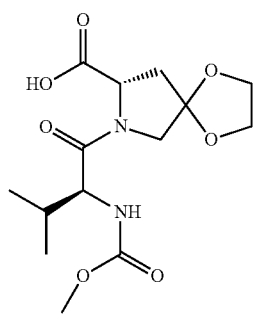 [SMILES: COC(=O)N[C@H](C(=O)N1CC2(C[C@H]1C(=O)O)OCCO2)C(C)C]

$^1$H NMR (400 MHz, DMSO-d$_6$) δ ppm 12.56 (br. s., 1H) 7.40 (d, J=8.39 Hz, 1H) 4.33 (dd, J=8.78, 7.02 Hz, 1H) 3.81-4.10 (m, 5H) 3.41-3.66 (m, 5H) 2.28-2.43 (m, 1H) 1.94-2.11 (m, 1H) 1.74-1.94 (m, 1H) 0.67-1.05 (m, 6H). ES LC-MS m/z=331.6 (M+H)$^+$.

Example 1 methyl [(1S)-1-({(2S)-2-[4-(4'-{2-[(3S,7S,9S)-7,9-dimethyl-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate mmol) and HATU (108 mg, 0.284 mmol). After ~3 min stirring, methyl {(1S)-1-[((2S)-2-{4-[4'-(aminoacetyl)-4-biphenylyl]-1H-imidazol-2-yl}-1-pyrrolidinyl)carbonyl]-2-methylpropyl}carbamate dihydrochloride (Intermediate 1) (149 mg, 0.258 mmol) was introduced. After the reaction was stirred for additional 2 hrs at rt, the mixture was directly loaded to RP HPLC, eluting with 5 to 80% acetonitrile/water (0.2% NH$_3$H$_2$O (conc.)) to give methyl [(1S)-1-({(2S)-2-[4-(4'-{2-[(3S,7S,9S)-7,9-dimethyl-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate (Intermediate 3) as solid (135 mg, yield: 61%). $^1$HNMR (400 MHz, CHLOROFORM-d) δ ppm

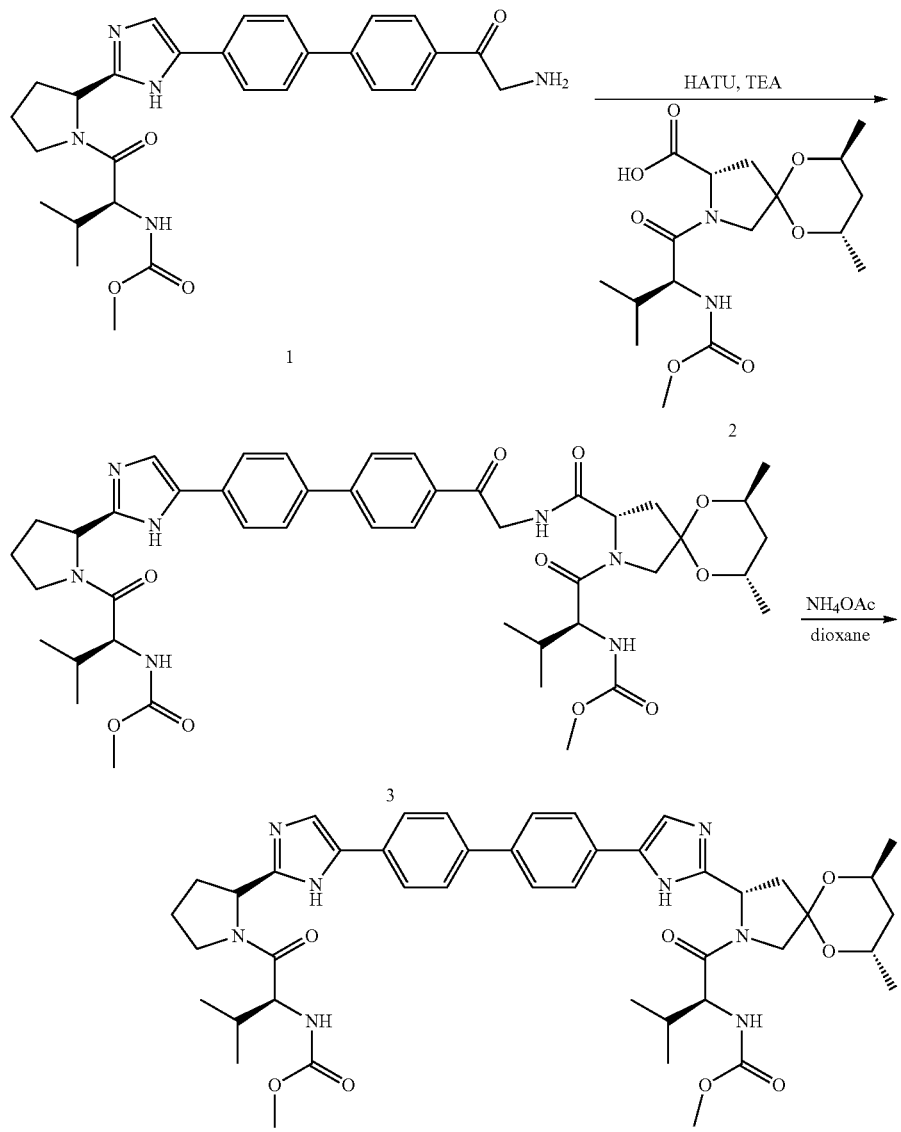

Example 1

To a stirred solution of ((3S,7S,9S)-7,9-dimethyl-2-{N-[(methyloxy)carbonyl]-L-valyl}-6,10-dioxa-2-azaspiro[4.5]decane-3-carboxylic acid (Intermediate 2) (96 mg, 0.258 mmol) in DMF (2 mL) were added TEA (78 mg, 0.773

10.40-11.01 (m, 1H) 7.32-8.30 (m, 10H) 5.28 (br. s., 2H) 4.53-4.96 (m, 4H) 4.17-4.53 (m, 1H) 3.40-4.17 (m, 11H) 2.83-3.22 (m, 1H) 2.26-2.74 (m, 3H) 1.54-2.26 (m, 8H) 0.47-1.43 (m, 18H). ES LC-MS m/z=858.6 (M+H)$^+$.

To a stirred solution of methyl [(1S)-1-({(2S)-2-[4-(4'-{2-[(3S,7S,9S)-7,9-dimethyl-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate (Intermediate 3) (135 mg, 0.157 mmol) in dioxane (3 mL) was added ammonium acetate (121 mg, 1.57 mmol). The reaction mixture was heated to 110° C. in a sealed tube overnight. Cooled down to rt, filtered off excess of ammonium acetate. The filtrate was evaporated and the residue was purified by column chromatography (silica gel, 0-15% methanol in ethyl acetate) to give methyl [(1S)-1-({(2S)-2-[4-(4'-{2-[(3S,7S,9S)-7,9-dimethyl-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate (Example 1) as solid (81 mg, yield: 58%).
¹HNMR (400 MHz, CHLOROFORM-d) δ ppm 10.23-11.01 (m, 1H) 7.31-8.08 (m, 8H) 7.23 (d, J=8.03 Hz, 2H) 5.13-5.89 (m, 4H) 3.34-4.69 (m, 13H) 2.84-3.31 (m, 2H) 2.63-2.84 (m, 1H) 2.29-2.53 (m, 1H) 1.85-2.29 (m, 4H) 1.56-1.85 (m, 4H) 1.16-1.47 (m, 6H) 0.63-1.16 (m, 12H). HRMS: (M+H)⁺ calcd: 835.4456. found: 835.4458.

Example 2 methyl [(1S)-2-methyl-1-({(2S)-2-[4-(4'-{2-[(8S)-7-((2S)-3-methyl-2-{[(methyloxy)carbonyl]amino}butanoyl)-1,4-dioxa-7-azaspiro[4.4]non-8-yl]-1H-imidazol-4-yl}-4-biphenylyl)-1H-imidazol-2-yl]-1-pyrrolidinyl}carbonyl)propyl]carbamate Methyl [(1S)-2-methyl-1-({(2S)-2-[4-(4'-{2-[(8S)-7-((2S)-3-methyl-2-{[(methyloxy)carbonyl]amino}butanoyl)-1,4-dioxa-7-azaspiro[4.4]non-8-yl]-1H-imidazol-4-yl}-4-biphenylyl)-1H-imidazol-2-yl]-1-pyrrolidinyl}carbonyl)propyl]carbamate was obtained from (8S)-7-{N-[(methyloxy)carbonyl]-L-valyl}-1,4-dioxa-7-azaspiro[4.4]nonane-8-carboxylic acid (Intermediate 17) and methyl {(1S)-1-[((2S)-2-{4-[4'-(aminoacetyl)-4-biphenylyl]-1H-imidazol-2-yl}-1-pyrrolidinyl)carbonyl]-2-methylpropyl}carbamate dihydrochloride (Intermediate 1), following the similar two-step synthetic procedures outlined in Example 1. ¹H NMR (400 MHz, CHLOROFORM-d) δ ppm 10.00-11.36 (m, 2H) 7.56 (br. s., 10H) 7.02-7.34 (m, 2H) 5.05-5.89 (m, 4H) 3.76-4.65 (m, 6H) 3.53-3.83 (m, 6H) 2.77-3.54 (m, 2H) 2.26-2.70 (m, 2H) 1.45-2.26 (m, 6H) 0.61-1.25 (m, 12H). HRMS: (M+H)⁺ calcd: 797.3986. found: 797.3981.

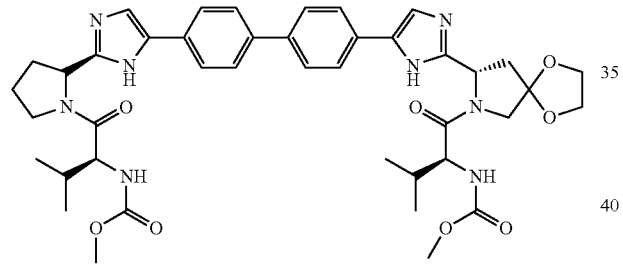

Example 3 dimethyl (4,4'-biphenyldiylbis{1H-imidazole-4,2-diyl[(3S,7S,9S)-7,9-dimethyl-6,10-dioxa-2-azaspiro[4.5]decane-3,2-diyl][(2S)-3-methyl-1-oxo-1,2-butanediyl]})biscarbamate

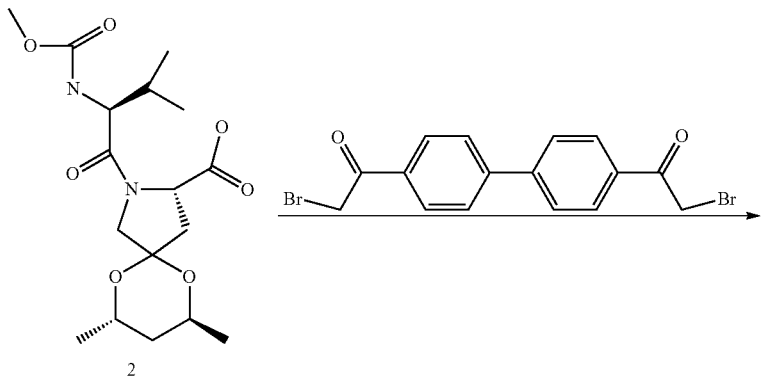

-continued

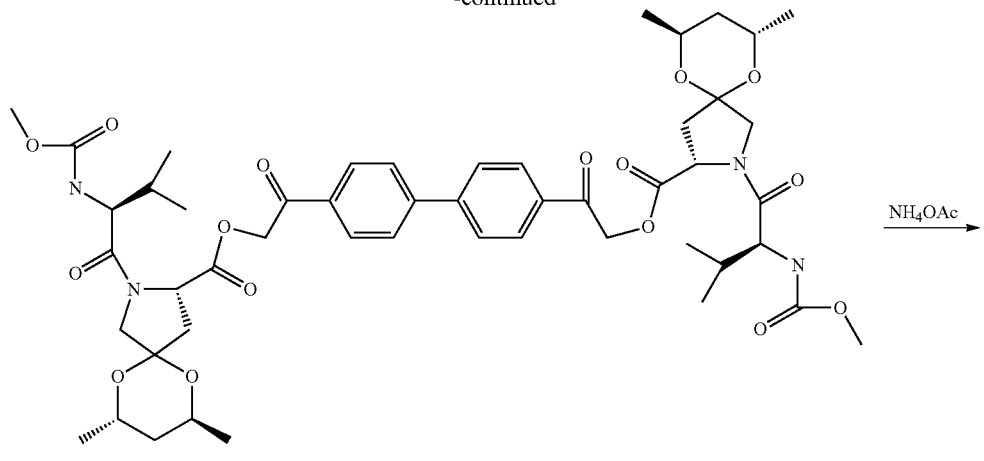

18

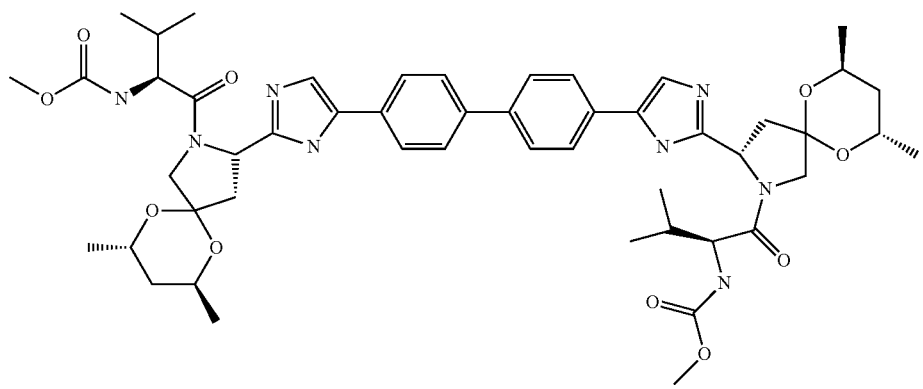

Example 3

Under N₂ atmosphere, to a stirred suspension of 1,1'-(4,4'-biphenyldiyl)bis(2-bromoethanone) (113 mg, 0.285 mmol, prepared according to the procedures provided in WO2009020825) in acetonitrile (5 mL) was added (3S,7S,9S)-7,9-dimethyl-2-{N-[(methyloxy)carbonyl]-L-valyl}-6,10-dioxa-2-azaspiro[4.5]decane-3-carboxylic acid (Intermediate 2) (212 mg, 0.571 mg), followed by addition of TEA (57.5 mg, 0.571 mmol). The mixture was stirred at 50° C. until the suspension became clear. After it was cooled down to rt, the reaction mixture was diluted with ethyl acetate and washed with brine. The organic phase was dried over MgSO₄, filtered and evaporated to give 4,4'-biphenyldiylbis-2-oxo-2,1-ethanediyl(3S,7S,9S,3'S,7'S,9'S)bis(7,9-dimethyl-2-{N-[(methyloxy)carbonyl]-L-valyl}-6,10-dioxa-2-azaspiro[4.5]decane-3-carboxylate) (Intermediate 18) (280 mg, quant.). ES LC-MS m/z=979.6 (M+H)⁺.

To a stirred solution of 4,4'-biphenyldiylbis-2-oxo-2,1-ethanediyl(3S,7S,9S,3'S,7'S,9'S)bis(7,9-dimethyl-2-{N-[(methyloxy)carbonyl]-L-valyl}-6,10-dioxa-2-azaspiro[4.5]decane-3-carboxylate) (Intermediate 18) (280 mg, 0.286 mmol) in dioxane (5 mL) in a sealed tube was added ammonium acetate (441 mg, 5.72 mmol). The reaction mixture was heated to 110° C. overnight. Cooled down to rt, filtered off excess of ammonium acetate. The filtrate was evaporated and the residue was purified by column (silica gel, 0-15% methanol in ethyl acetate) to give dimethyl (4,4'-biphenyldiylbis{1H-imidazole-4,2-diyl[(3S,7S,9S)-7,9-dimethyl-6,10-dioxa-2-azaspiro[4.5]decane-3,2-diyl][(2S)-3-methyl-1-oxo-1,2-butanediyl]})biscarbamate (Example 3) as a solid (112 mg, yield: 40%). ¹H NMR (400 MHz, CHLOROFORM-d) δ ppm 10.30-10.99 (m, 2H) 7.68-8.00 (m, 2H) 7.61 (d, J=7.53 Hz, 6H) 7.26-7.35 (m, 4H) 5.59 (d, J=8.53 Hz, 1H) 5.23-5.39 (m, 1H) 4.44 (dd, J=8.41, 5.14 Hz, 2H) 4.02-4.23 (m, 4H) 3.97 (d, J=10.29 Hz, 2H) 3.72 (s, 6H) 3.62 (d, J=10.29 Hz, 2H) 3.04-3.32 (m, 2H) 2.70 (d, J=13.05 Hz, 2H) 1.93 (br. s., 2H) 1.56-1.82 (m, 4H) 1.13-1.46 (m, 12H) 0.60-1.02 (m, 12H). HRMS: (M+H)⁺ calcd: 939.4980. found: 939.4981.

Example 4 dimethyl (4,4'-biphenyldiylbis{1H-imidazole-4,2-diyl(8S)-1,4-dioxa-7-azaspiro[4.4]nonane-8,7-diyl[(2S)-3-methyl-1-oxo-1,2-butanediyl]})biscarbamate

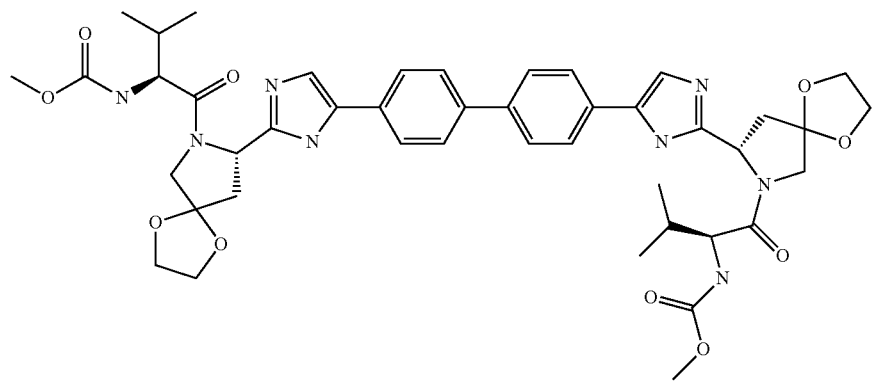 [SMILES: COC(=O)N[C@H](C(=O)N1CC2(C[C@H]1c1ncc(-c3ccc(-c4ccc(-c5cnc([C@@H]6CC7(CN6C(=O)[C@@H](NC(=O)OC)C(C)C)OCCO7)[nH]5)cc4)cc3)[nH]1)OCCO2)C(C)C]

Dimethyl (4,4'-biphenyldiylbis{1H-imidazole-4,2-diyl(8S)-1,4-dioxa-7-azaspiro[4.4]nonane-8,7-diyl[(2S)-3-methyl-1-oxo-1,2-butanediyl]})biscarbamate was obtained from 1,1'-(4,4'-biphenyldiyl)bis(2-bromoethanone) and (8S)-7-{N-[(methyloxy)carbonyl]-L-valyl}-1,4-dioxa-7-azaspiro[4.4]nonane-8-carboxylic acid (Intermediate 17) using a process similar to the two-step procedures outlined in Example 3. $^1$H NMR (400 MHz, CHLOROFORM-d) δ ppm 11.10-11.23 (m, 1H) 10.10-11.63 (m, 2H) 7.40-8.15 (m, 8H) 7.27-7.40 (m, 2H) 5.23-5.88 (m, 2H) 4.31 (dd, J=8.68, 6.54 Hz, 2H) 3.83-4.21 (m, 10H) 3.57-3.83 (m, 6H) 3.05-3.46 (m, 3H) 2.47 (dd, J=13.46, 8.59 Hz, 2H) 1.51-2.20 (m, 2H) 1.08 (d, J=6.83 Hz, 2H) 0.60-0.97 (m, 12H). HRMS: (M+H)$^+$ calcd: 855.4041. found: 855.4039.

Example 5 methyl ((1S)-1-methyl-2-{(3S)-3-[4-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-1H-imidazol-2-yl]-6,10-dioxa-2-azaspiro[4.5]dec-2-yl}-2-oxoethyl)carbamate

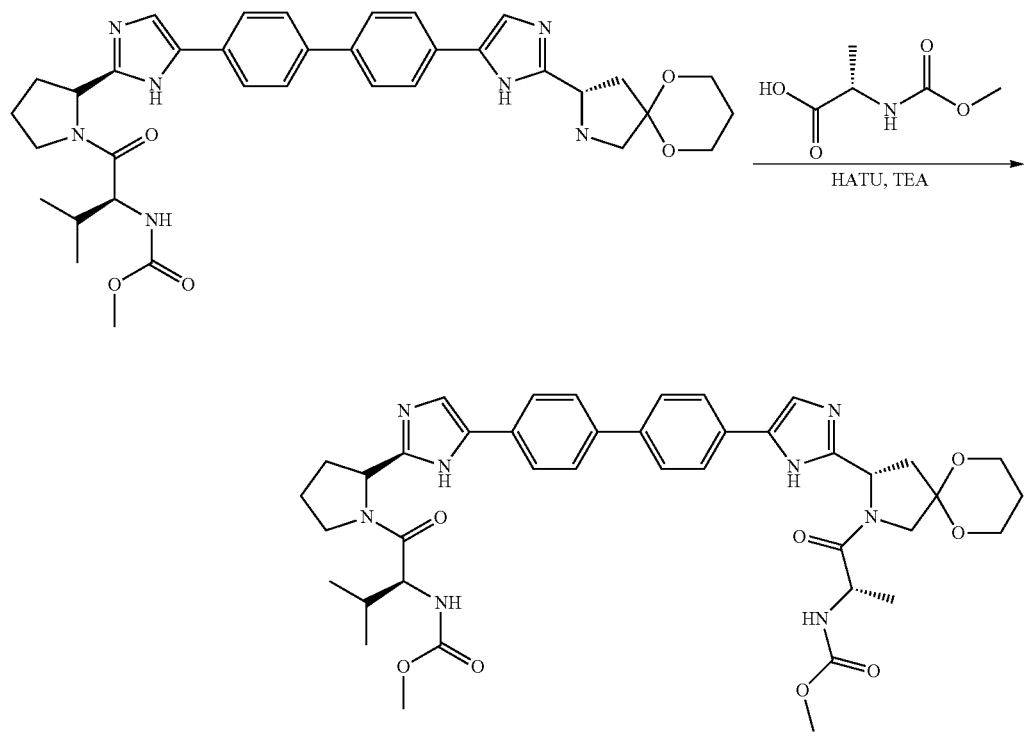

To a stirred solution of N-[(methyloxy)carbonyl]-L-alanine (22.5 mg, 0.153 mmol, prepared according to the procedure provided in WO2003055474) in DMF (2 mL) were added TEA (15.5 mg, 0.153 mmol) and HATU (58.2 mg, 0.153 mmol). After ~3 min stirring, methyl [(1S)-1-({(2S)-2-[4-(4'-{2-[(3S)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate (Example 19) (100 mg, 0.153 mmol) was introduced. After stirred for additional 2 hrs at rt, the reaction mixture was directly loaded to RP HPLC, eluting with 5 to 80% acetonitrile/water (0.2% $NH_3H_2O$ (conc.)), to give methyl ((1S)-1-methyl-2-{(3S)-3-[4-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-1H-imidazol-2-yl]-6,10-dioxa-2-azaspiro[4.5]dec-2-yl}-2-oxoethyl)carbamate (Example 5) as solid (36 mg, yield: 29%). $^1$H NMR (400 MHz, CHLOROFORM-d) δ ppm 10.04-11.11 (m, 2H) 7.37-8.02 (m, 8H) 7.18-7.36 (m, 2H) 5.60 (br. s., 2H) 5.17-5.40 (m, 2H) 3.17-4.73 (m, 14H) 2.79-3.19 (m, 1H) 2.45-2.81 (m, 1H) 2.29-2.45 (m, 1H) 1.49-2.29 (m, 8H) 1.22-1.47 (m, 3H) 0.73-1.16 (m, 6H). HRMS: $(M+H)^+$ calcd: 783.3830. found: 783.3832.

Intermediate 19: Preparation of methyl [(1S)-1-({(2S)-2-[4-(4'-{2-[(3S)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate Intermediate 19 can be prepared as illustrated in the reaction scheme below.

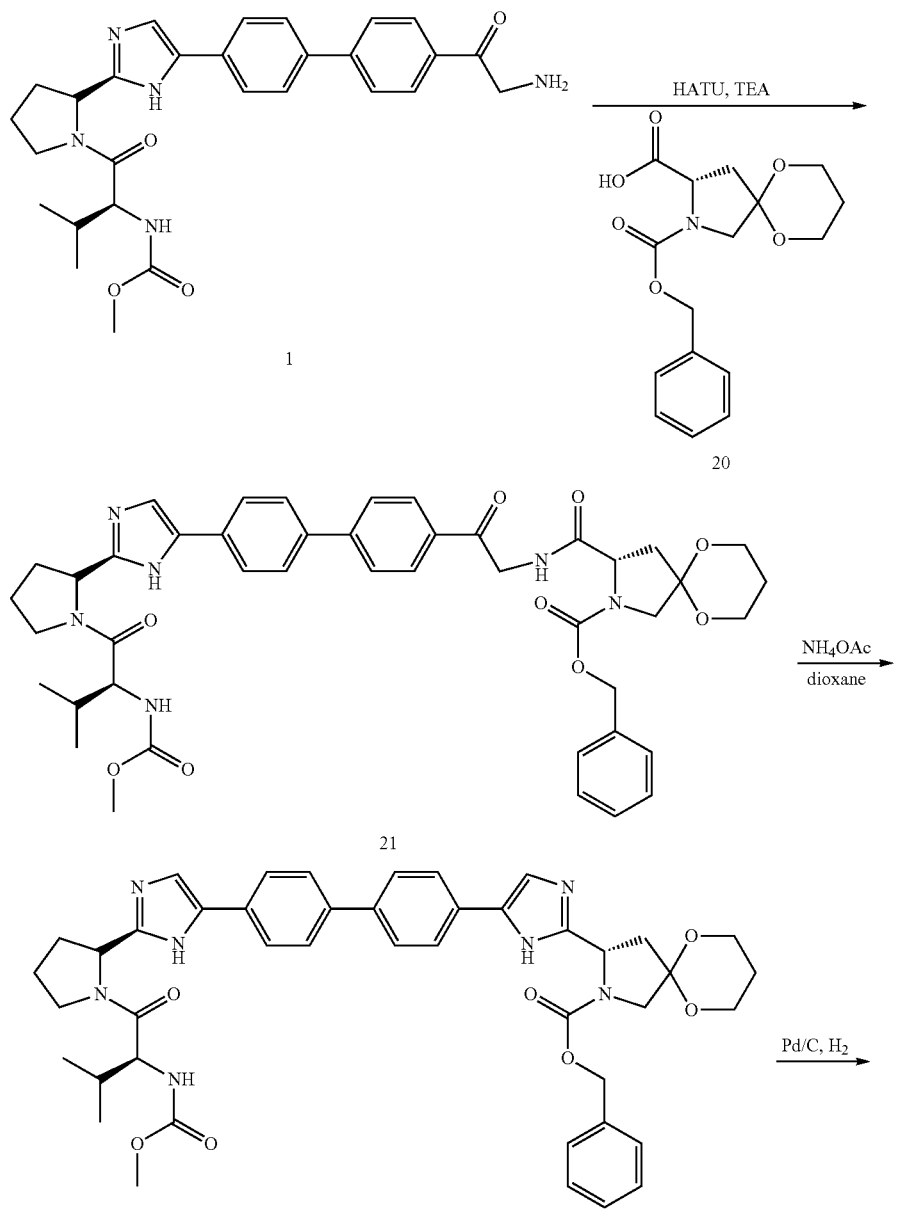

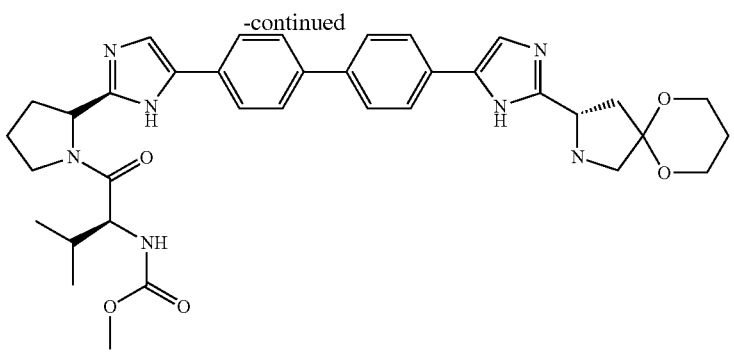

19

Intermediate 21: phenylmethyl(3S)-3-({[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]amino}carbonyl)-6,10-dioxa-2-azaspiro[4.5]decane-2-carboxylate

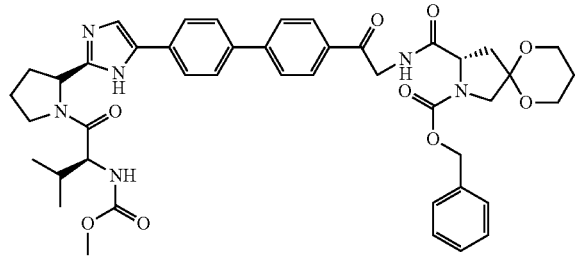

To a stirred solution of (3S)-2-{[(phenylmethyl)oxy]carbonyl}-6,10-dioxa-2-azaspiro[4.5]decane-3-carboxylic acid (Intermediate 20) (878 mg, 2.73 mmol) in DMF (10 mL) were added TEA (829 mg, 8.20 mmol) and HATU (1039 mg, 2.73 mmol). After ~3 min stirring, methyl [(1S)-1-({(2S)-2-[4-(4'-{2-[(3S)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate (Intermediate 1) (1575 mg, 2.73 mmol) was added. The resulting mixture was stirred for additional 2 hrs at rt before quenched with NaHCO3 (ss) and extracted with EtOAc (3×). The combined organic layers was dried over Na₂SO₄, filtered and evaporated. The crude product was purified by column chromatography (silica gel, 0 to 6% MeOH (2M ammonia) in DCM) to give phenylmethyl (3S)-3-({[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]amino}carbonyl)-6,10-dioxa-2-azaspiro[4.5]decane-2-carboxylate (Intermediate 21) as a solid (1.76 g, yield: 80%). ES LC-MS m/z=807.5 (M+H)⁺.

Intermediate 22: phenylmethyl(3S)-3-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-6,10-dioxa-2-azaspiro[4.5]decane-2-carboxylate

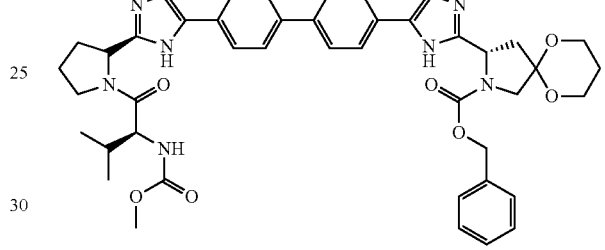

To a stirred solution of (3S)-3-({[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]amino}carbonyl)-6,10-dioxa-2-azaspiro[4.5]decane-2-carboxylate (Intermediate 21) (1.76 g, 2.18 mmol) in dioxane (5 mL) in a sealed tube was added ammonium acetate (1.68 d, 21.8 mmol). The reaction mixture was heated to 110° C. overnight. Cooled down to rt, filtered off excess of ammonium acetate. The filtrate was evaporated and the residue was purified by column (silica gel, 0-15% methanol in ethyl acetate) to give phenylmethyl (3S)-3-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-6,10-dioxa-2-azaspiro[4.5]decane-2-carboxylate (Intermediate 22) (1.44 g, yield 84%) as foam. ES LC-MS m/z=788.5 (M+H)⁺.

Intermediate 19: methyl [(1S)-1-({(2S)-2-[4-(4'-{2-[(3S)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate

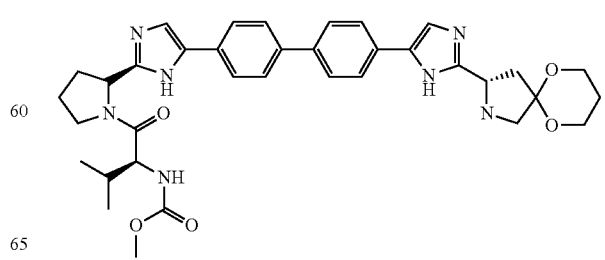

Phenylmethyl (3S)-3-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-6,10-dioxa-2-azaspiro[4.5]decane-2-carboxylate (Intermediate 22) (1.44 g, 1.83 mmol) was hydrogenated in ethanol (100 mL) with balloon under the catalysis of Pd/C for 20 hrs to give methyl [(1S)-1-({(2S)-2-[4-(4'-{2-[(3S)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate (Intermediate 19). ES LC-MS m/z=654.4 (M+H)+.

Intermediate 20: (3S)-2-{[(phenylmethyl)oxy]carbonyl}-6,10-dioxa-2-azaspiro[4.5]decane-3-carboxylic acid Intermediate 20 can be prepared as illustrated in the reaction scheme below.

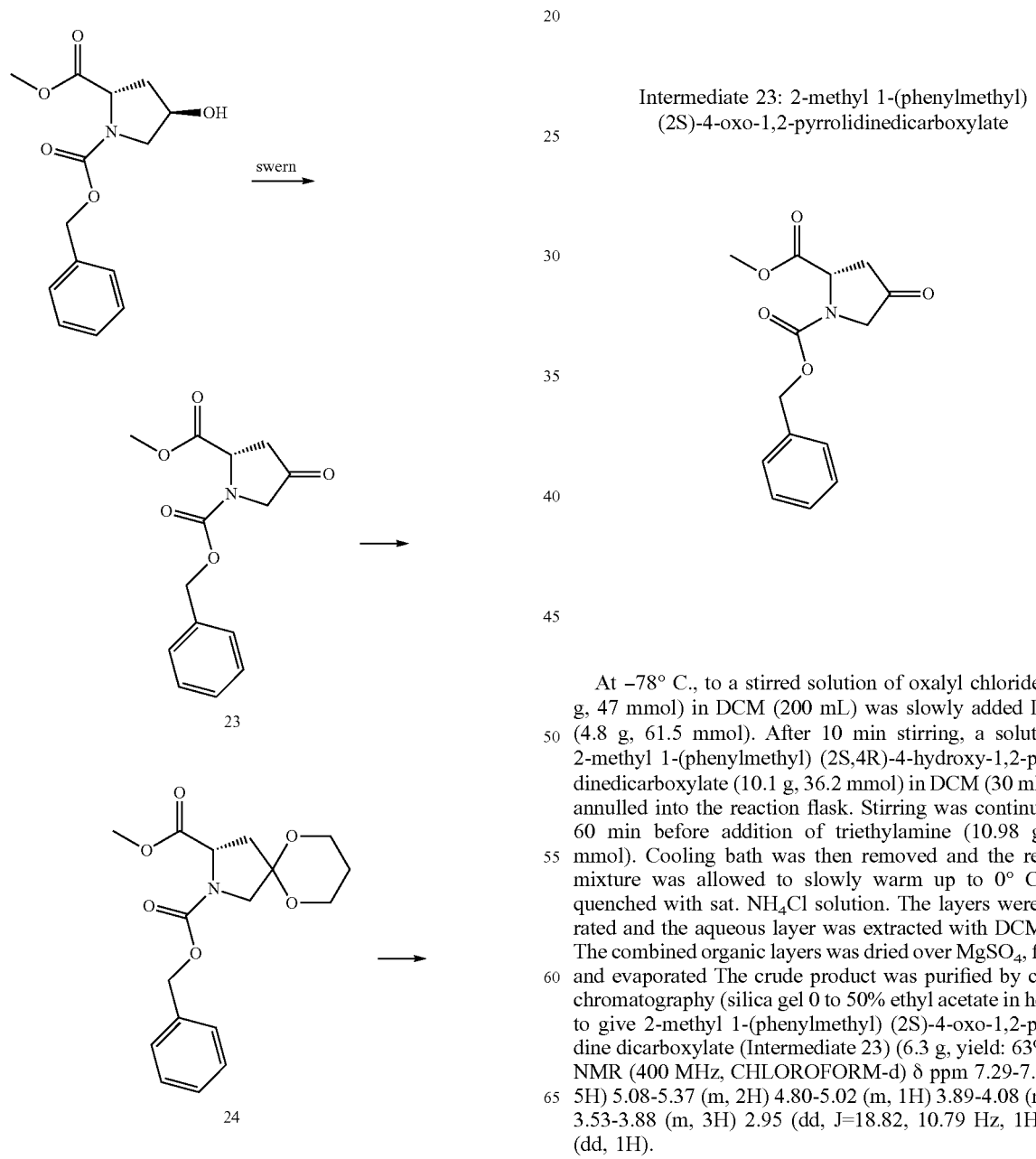

23

24

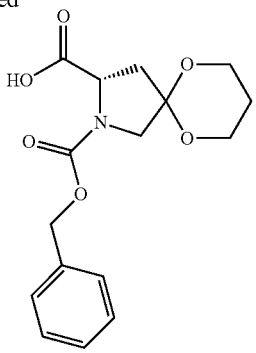

20

Intermediate 23: 2-methyl 1-(phenylmethyl) (2S)-4-oxo-1,2-pyrrolidinedicarboxylate At −78° C., to a stirred solution of oxalyl chloride (5.97 g, 47 mmol) in DCM (200 mL) was slowly added DMSO (4.8 g, 61.5 mmol). After 10 min stirring, a solution of 2-methyl 1-(phenylmethyl) (2S,4R)-4-hydroxy-1,2-pyrrolidinedicarboxylate (10.1 g, 36.2 mmol) in DCM (30 mL) was annulled into the reaction flask. Stirring was continued for 60 min before addition of triethylamine (10.98 g, 108 mmol). Cooling bath was then removed and the reaction mixture was allowed to slowly warm up to 0° C., and quenched with sat. NH₄Cl solution. The layers were separated and the aqueous layer was extracted with DCM (2×). The combined organic layers was dried over MgSO₄, filtered and evaporated The crude product was purified by column chromatography (silica gel 0 to 50% ethyl acetate in hexane) to give 2-methyl 1-(phenylmethyl) (2S)-4-oxo-1,2-pyrrolidine dicarboxylate (Intermediate 23) (6.3 g, yield: 63%). ¹H NMR (400 MHz, CHLOROFORM-d) δ ppm 7.29-7.56 (m, 5H) 5.08-5.37 (m, 2H) 4.80-5.02 (m, 1H) 3.89-4.08 (m, 2H) 3.53-3.88 (m, 3H) 2.95 (dd, J=18.82, 10.79 Hz, 1H) 2.63 (dd, 1H).

Intermediate 24: 3-methyl 2-(phenylmethyl) (3S)-6,10-dioxa-2-azaspiro[4.5]decane-2,3-dicarboxylate

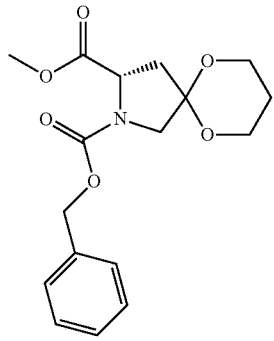 [SMILES: COC(=O)[C@@H]1CC2(CN1C(=O)OCc1ccccc1)OCCCO2]

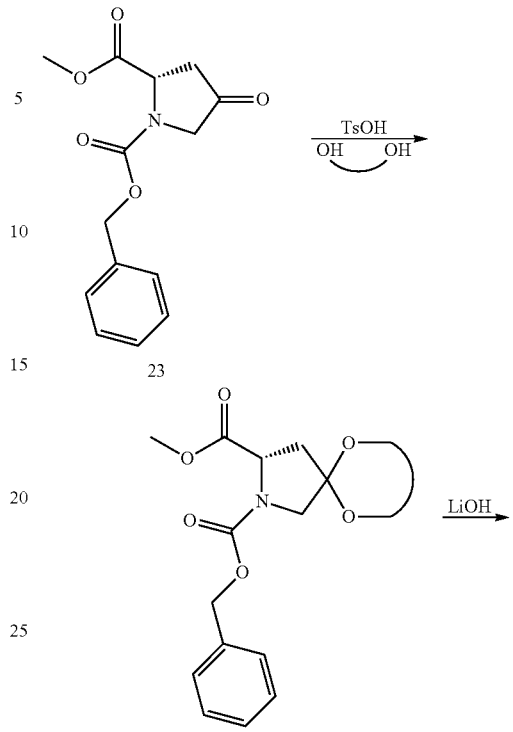

3-Methyl 2-(phenylmethyl) (3S)-6,10-dioxa-2-azaspiro[4.5]decane-2,3-dicarboxylate (Intermediate 24) (1.02 g, yield 84%) was prepared from 2-methyl 1-(phenylmethyl) (2S)-4-oxo-1,2-pyrrolidinedicarboxylate (1.0 g, 3.61 mmol) and 1,3-propanediol (0.55 g, 7.21 mmol) following the similar procedure outlined in the preparation of Intermediate 14 $^1$H NMR (400 MHz, CHLOROFORM-d) δ ppm 7.05-7.61 (m, 5H) 4.91-5.25 (m, 2H) 4.29-4.68 (m, 1H) 3.75-4.07 (m, 5H) 3.38-3.75 (m, 4H) 2.25-2.67 (m, 2H) 1.51-2.00 (m, 1H). ES LC-MS m/z=336.6 (M+H)$^+$.

Intermediate 20: (3S)-2-{[(phenylmethyl)oxy]carbonyl}-6,10-dioxa-2-azaspiro[4.5]decane-3-carboxylic acid

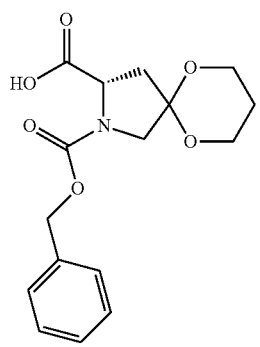 [SMILES: O=C(O)[C@@H]1CC2(CN1C(=O)OCc1ccccc1)OCCCO2]

(3S)-2-{[(phenylmethyl)oxy]carbonyl}-6,10-dioxa-2-azaspiro[4.5]decane-3-carboxylic acid (Intermediate 20) (878 mg, yield: 90%) was obtained from 3-methyl 2-(phenylmethyl) (3S)-6,10-dioxa-2-azaspiro[4.5]decane-2,3-dicarboxylate (Intermediate 24) (1.02 g, 3.04 mmol) and LiOH (80 mg, 3.35 mmol), following the similar procedure outlined in the preparation of intermediate 2. ES LC-MS m/z=322.2 (M+H)$^+$.

Intermediates 26, 27, 28, 29, 31, 33 and 34 were prepared using procedures similar to those described in the preparation of Intermediate 20:

Intermediate 25: 3-methyl 2-(phenylmethyl) (3S)-6,10-dioxa-2-azaspiro[4.5]decane-2,3-dicarboxylate-d$_2$

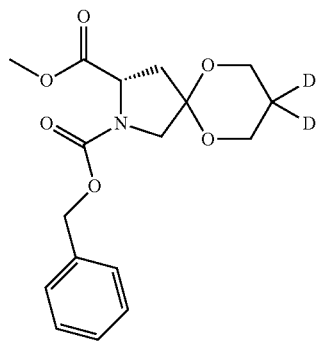 [SMILES: [2H]C1([2H])COC2(C[C@@H](C(=O)OC)N(C(=O)OCc3ccccc3)C2)OC1]

$^1$H NMR (400 MHz, CHLOROFORM-d) δ ppm 7.27-7.46 (m, 5H) 4.97-5.27 (m, 2H) 4.29-4.64 (m, 1H) 3.72-4.02 (m, 6H) 3.49-3.72 (m, 3H) 2.19-2.67 (m, 2H). ES LC-MS m/z=338.2 (M+H)$^+$.

Intermediate 26: (3S)-2-{[(phenylmethyl)oxy]carbonyl}-6,10-dioxa-2-azaspiro[4.5]decane-3-carboxylic acid-d₂

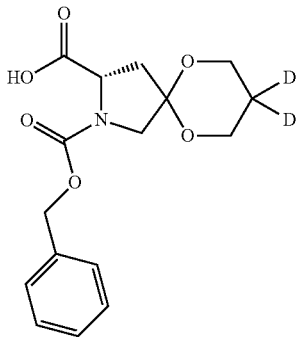 [SMILES: [2H]C1([2H])COC2(C[C@@H](C(=O)O)N(C(=O)OCc3ccccc3)C2)OC1]

ES LC-MS m/z=324.2 (M+H)⁺.

Intermediate 27: (3S)-8,8-dimethyl-2-{[(phenylmethyl)oxy]carbonyl}-6,10-dioxa-2-azaspiro[4.5]decane-3-carboxylic acid

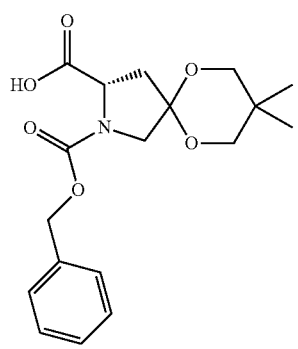 [SMILES: CC1(C)COC2(C[C@@H](C(=O)O)N(C(=O)OCc3ccccc3)C2)OC1]

Intermediate 28: (3S)-2-{[(phenylmethyl)oxy]carbonyl}-6,10-dioxa-2-azaspiro[4.5]decane-3-carboxylic acid-d₆

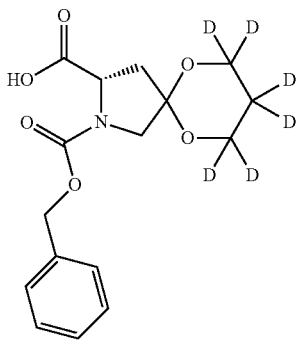 [SMILES: [2H]C1([2H])OC2(C[C@@H](C(=O)O)N(C(=O)OCc3ccccc3)C2)OC([2H])([2H])C1([2H])[2H]]

Intermediate 29: (8S)-7-{[(phenylmethyl)oxy]carbonyl}-1,4-dioxa-7-azaspiro[4.4]nonane-8-carboxylic acid-d₄

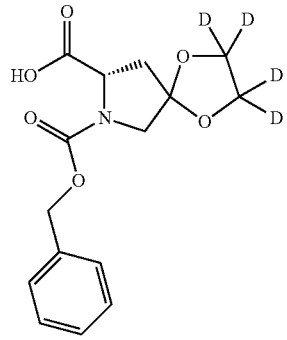 [SMILES: [2H]C1([2H])OC2(C[C@@H](C(=O)O)N(C(=O)OCc3ccccc3)C2)OC1([2H])[2H]]

Intermediate 30: 8-methyl 7-(phenylmethyl)(2R,3R,8S)-2,3-dimethyl-1,4-dioxa-7-azaspiro[4.4]nonane-7,8-dicarboxylate

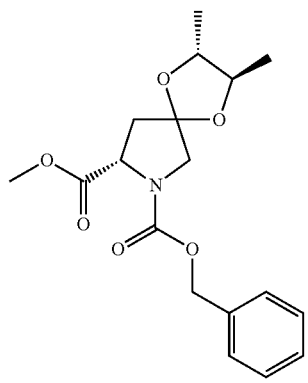 [SMILES: COC(=O)[C@@H]1CC2(CN1C(=O)OCc1ccccc1)O[C@H](C)[C@@H](C)O2]

¹H NMR (400 MHz, DMSO-d6) δ ppm 1.12-1.24 (m, 6H), 2.00-2.18 (m, 1H), 2.35-2.46 (m, 1H), 3.32 (s, 1H), 3.35-3.44 (m, 1H), 3.56 (s, 2H), 3.64 (s, 3H), 4.28-4.37 (m, 1H), 4.38-4.45 (m, 0H), 5.09 (s, 2H), 7.24-7.41 (m, 5H) LC-MS (ESI): m/z=350.1 (M+H)⁺;

Intermediate 31: (2R,3R,8S)-2,3-dimethyl-7-{[(phenylmethyl)oxy]carbonyl}-1,4-dioxa-7-azaspiro[4.4]nonane-8-carboxylic acid

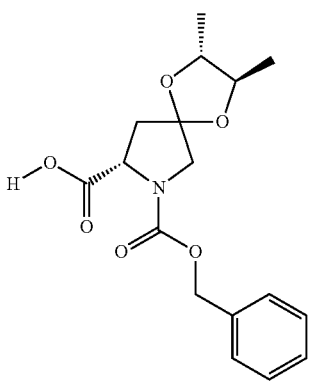 [SMILES: C[C@H]1OC2(C[C@@H](C(=O)O)N(C(=O)OCc3ccccc3)C2)O[C@@H]1C]

LC-MS (ESI): m/z=336.2 (M+H)⁺;

Intermediate 32: 8-methyl 7-(phenylmethyl) (2S,3S,8S)-2,3-dimethyl-1,4-dioxa-7-azaspiro[4.4]nonane-7,8-dicarboxylate

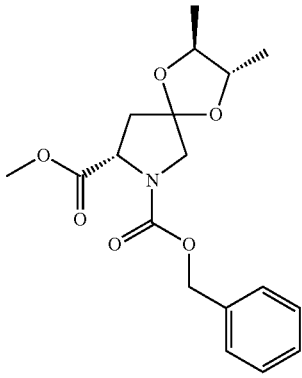 [SMILES: COC(=O)[C@@H]1CC2(CN1C(=O)OCc1ccccc1)O[C@@H](C)[C@H](C)O2]

¹HNMR (400 MHz, CHLOROFORM-d) δ □ppm 1.18-1.31 (m, 6H), 2.23 (dd, J=13.1, 5.9 Hz, 1H), 2.39 (dt, J=13.1, 8.0 Hz, 1H), 3.49-3.66 (m, 6H), 3.76 (s, 1H), 4.39-4.56 (m, 1H), 4.98-5.26 (m, 2H), 7.36 (s, 5H)

LC-MS (ESI): m/z=350.1 (M+H)⁺;

Intermediate 33: (2S,3S,8S)-2,3-dimethyl-7-{[(phenylmethyl)oxy]carbonyl}-1,4-dioxa-7-azaspiro[4.4]nonane-8-carboxylic acid

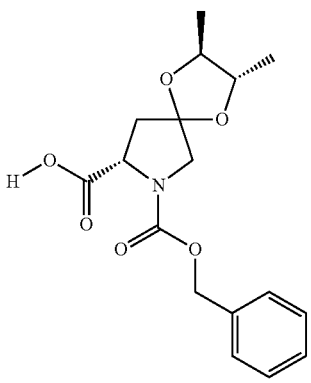 [SMILES: C[C@@H]1OC2(C[C@@H](C(=O)O)N(C(=O)OCc3ccccc3)C2)O[C@H]1C]

LC-MS (ESI): m/z=336.2 (M+H)⁺;

Intermediate 34: (5'S)-1'-{[(phenylmethyl)oxy]carbonyl}tetrahydrospiro[furo[3,4-d][1,3]dioxole-2,3'-pyrrolidine]-5'-carboxylic acid

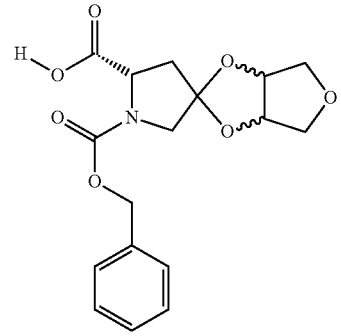

LC-MS (ESI): m/z=350.2 (M+H)⁺;

Example 6 methyl [(1S)-2-methyl-1-({(2S)-2-[4-(4'-{2-[(3S)-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)propyl]carbamate

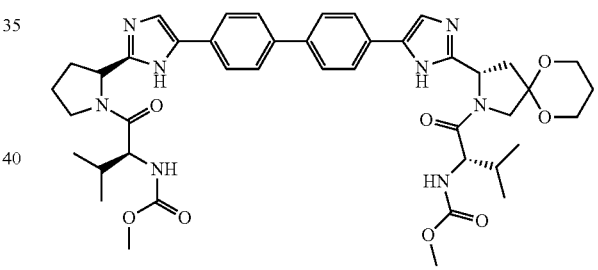

Methyl [(1S)-2-methyl-1-({(2S)-2-[4-(4'-{2-[(3S)-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)propyl]carbamate (47 mg, yield: 53%) was prepared from methyl [(1S)-1-({(2S)-2-[4-(4'-{2-[(3S)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate (Intermediate 19) (68 mg, 0.104 mmol), N-[(methyloxy)carbonyl]-L-valine (18.2 mg, 0.104) and HATU (40 mg, 0.104 mmol), following the similar procedure outlined in Example 5. ¹H NMR (400 MHz, CHLOROFORM-d) δ ppm 10.20-11.06 (m, 2H) 7.35-8.02 (m, 8H) 7.22 (d, J=7.78 Hz, 2H) 4.97-5.89 (m, 4H) 3.22-4.58 (m, 15H) 2.83-3.20 (m, 1H) 2.58-2.83 (m, 1H) 2.29-2.58 (m, 1H) 1.57-2.31 (m, 8H) 0.64-1.22 (m, 12H). HRMS: (M+H)⁺ calcd: 811.4143. found: 811.4142.

Examples 7 to 11 were prepared using the similar synthetic sequence described for synthesis of Example 5

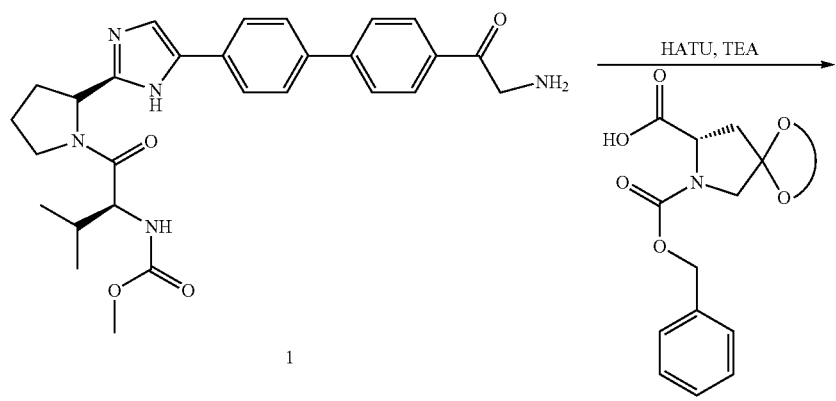
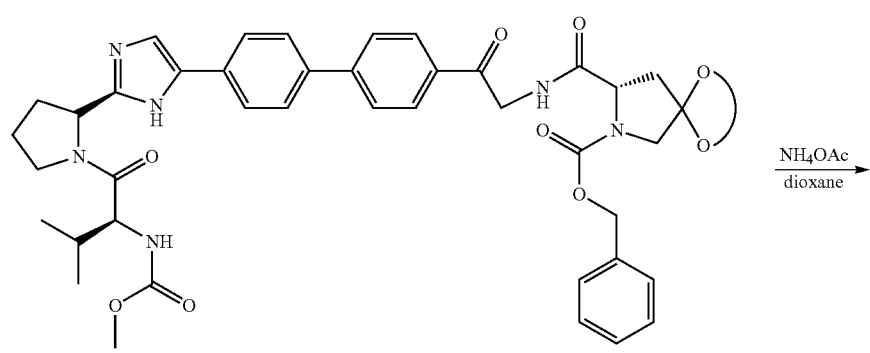
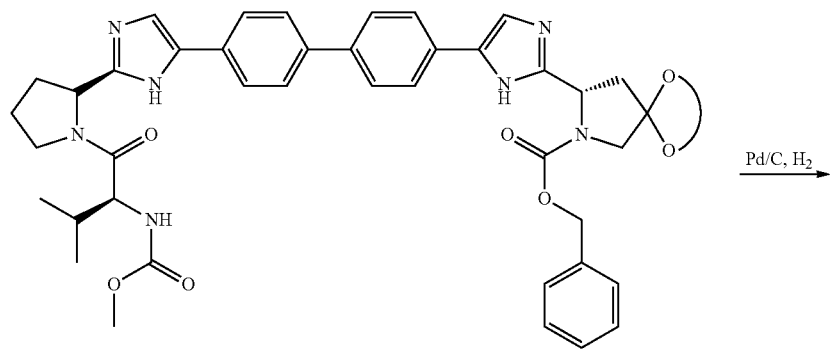
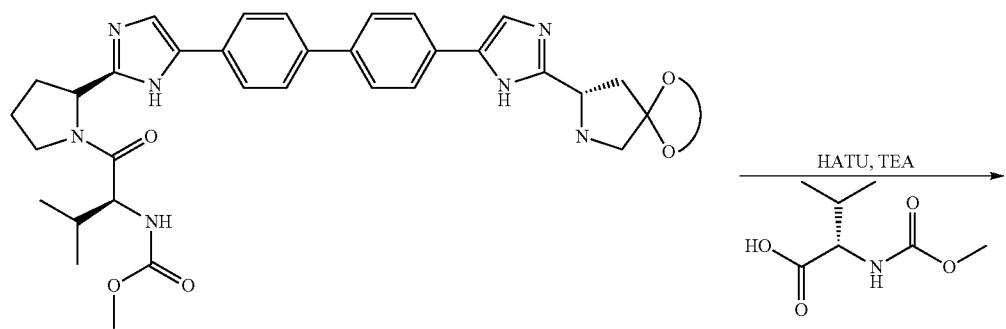

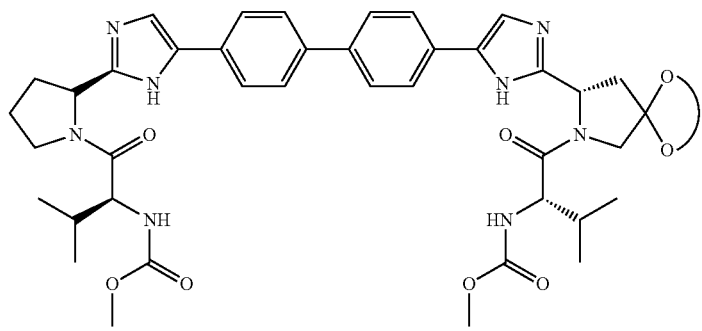
Example 7
methyl [(1S)-1-({(2S)-2-[4-(4'-{2-[(3S)-8,8-dimethyl-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl] carbamate
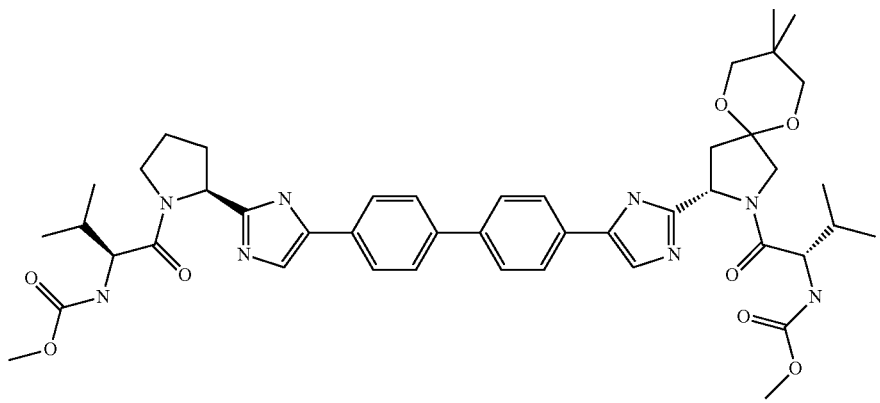 [SMILES: COC(=O)N[C@H](C(=O)N1CCC[C@H]1c1ncc(-c2ccc(-c3ccc(-c4cnc([C@@H]5CC6(CN5C(=O)[C@@H](NC(=O)OC)C(C)C)OCC(C)(C)CO6)[nH]4)cc3)cc2)[nH]1)C(C)C]
$^1$H NMR (400 MHz, DMSO-$d_6$) δ (ppm) 11.84 (br. s., 1H), 11.80 (br. s, 1H), 7.90-7.60 (br. m, 9H), 7.52 (s, 1H), 7.36-7.25 (br. m, 2H), 5.09 (br. m, 1H), 4.98 (m, 1H), 4.49 (br. m, 1H), 4.14-4.02 (br. m, 2H), 3.81 (br, 2H), 3.73-3.40 (br. m, 11H), 2.65 (m, 1H), 2.43-2.09 (br. m, 3H), 2.07-1.81 (br. m, 4H), 1.05-0.75 (br. m, 18H) ES LC-MS m/z=839 (M+H)$^+$ Purity (LC/MS) 96%

Example 8 methyl [(1S)-2-methyl-1-({(2S)-2-[4-(4'-{2-[(3S)-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)propyl]carbamate-d$_6$

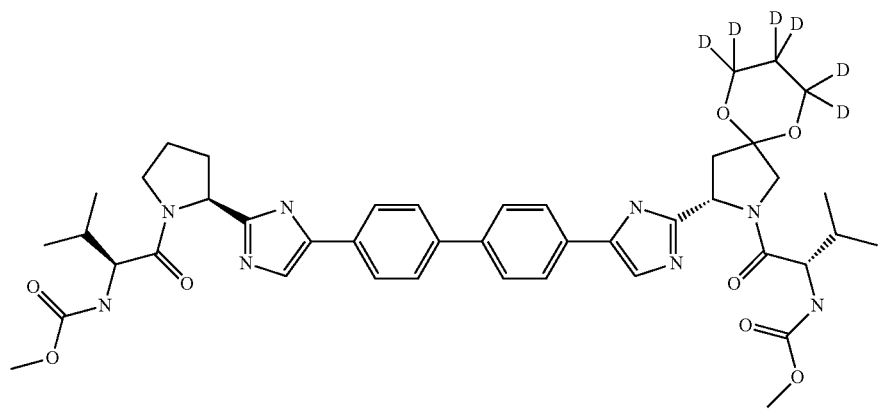 [SMILES: [2H]C1([2H])OC2(C[C@@H](c3ncc(-c4ccc(-c5ccc(-c6cnc([C@@H]7CCCN7C(=O)[C@@H](NC(=O)OC)C(C)C)[nH]6)cc5)cc4)[nH]3)N(C(=O)[C@@H](NC(=O)OC)C(C)C)C2)OC([2H])([2H])C1([2H])[2H]]

$^1$H NMR (400 MHz, CD$_3$OD) δ ppm 7.62 (m, 8H), 7.29 (m, 2H), 5.17 (m, 2H), 4.20 (m, 2H), 4.00 (m, 2H), 3.88 (m, 2H), 3.65 (s, 6H), 2.65-2.03 (m, 8H), 0.90 (m, 12H).

LC-MS for C$_{43}$H$_{48}$N$_8$O$_8$D$_6$ (M+H)$^+$ calc: 817. found: 817.

HRMS for C$_{43}$H$_{48}$N$_8$O$_8$D$_6$ (M+H)$^+$ calc: 817.4519. found: 817.4517.

Purity (LC/MS) 95%

Example 9 methyl [(1S)-2-methyl-1-({(2S)-2-[4-(4'-{2-[(8S)-7-((2S)-3-methyl-2-{[(methyloxy)carbonyl]amino}butanoyl)-1,4-dioxa-7-azaspiro[4.4]non-8-yl]-1H-imidazol-4-yl}-4-biphenylyl)-1H-imidazol-2-yl]-1-pyrrolidinyl}carbonyl)propyl]carbamate-d$_4$

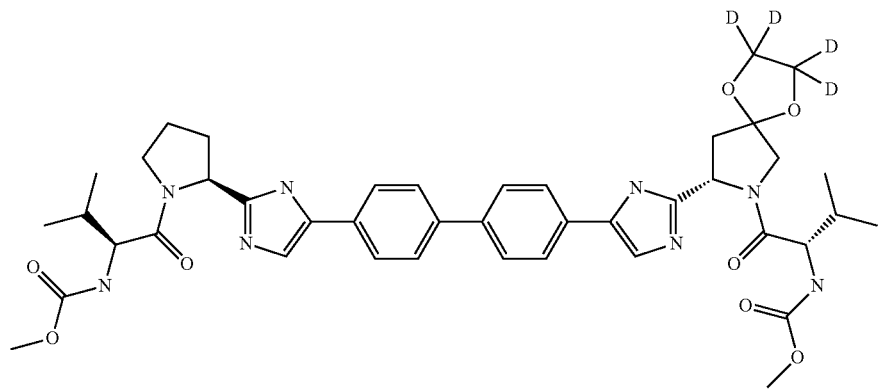 [SMILES: [2H]C1([2H])OC2(C[C@@H](c3ncc(-c4ccc(-c5ccc(-c6cnc([C@@H]7CCCN7C(=O)[C@@H](NC(=O)OC)C(C)C)[nH]6)cc5)cc4)[nH]3)N(C(=O)[C@@H](NC(=O)OC)C(C)C)C2)OC1([2H])[2H]]

$^1$H NMR (400 MHz, CD$_3$OD) δ ppm 7.60 (m, 8H), 7.28 (m, 2H), 5.17 (m, 2H), 4.23 (m, 1H), 4.15 (m, 1H), 4.06 (m, 1H), 3.97 (m, 1H), 3.88 (m, 2H), 3.64 (s, 6H), 2.50-2.00 (m, 8H), 0.90 (m, 12H). LC-MS for C$_{42}$H$_{48}$N$_8$O$_8$D$_4$ (M+H)$^+$ calc: 801. found: 801.

HRMS for C$_{42}$H$_{48}$N$_8$O$_8$D$_4$ (M+H)$^+$ calc: 801.4237. found: 801.4238.

Purity (LC/MS) 91%

Example 10 methyl [(1S)-1-({(2S)-2-[4-(4'-{2-[(2R,3R,8S)-2,3-dimethyl-7-((2S)-3-methyl-2-{[(methyloxy)carbonyl]amino}butanoyl)-1,4-dioxa-7-azaspiro[4.4]non-8-yl]-1H-imidazol-5-yl}-4-biphenylyl)-1H-imidazol-2-yl]-1-pyrrolidinyl}carbonyl)-2-methylpropyl] carbamate

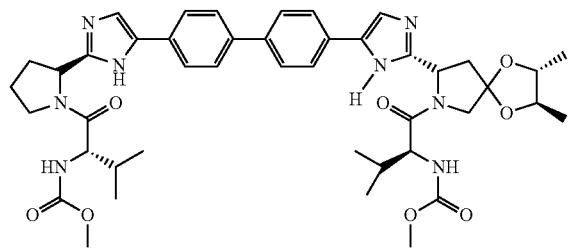

$^1$H NMR (400 MHz, DMSO-d6) δ □ppm 0.85 (d, J=6.4 Hz, 12H), 1.24 (dd, J=11.9, 5.8 Hz, 6H), 1.87-2.06 (m, 4H), 2.08-2.21 (m, 2H), 2.34-2.43 (m, 1H), 3.54 (s, 6H), 3.59-3.68 (m, 2H), 3.69-3.75 (m, 2H), 3.81 (br. s., 2H), 3.97-4.14 (m, 3H), 5.00-5.17 (m, 2H), 7.25-7.33 (m, 2H), 7.49-7.54 (m, 2H), 7.62-7.71 (m, 4H), 7.78 (d, J=7.7 Hz, 4H), 11.79 (br. s., 2H); LC-MS (ESI): m/z=825.5 (M+H)$^+$; HRMS: (M+H)$^+$ calcd, 825.4299. found, 825.4302. Purity: 92%

Example 11 methyl [(1S)-1-({(2S)-2-[4-(4'-{2-[(2S,3S,8S)-2,3-dimethyl-7-((2S)-3-methyl-2-{[(methyloxy)carbonyl]amino}butanoyl)-1,4-dioxa-7-azaspiro[4.4]non-8-yl]-1H-imidazol-5-yl}-4-biphenylyl)-1H-imidazol-2-yl]-1-pyrrolidinyl}carbonyl)-2-methylpropyl] carbamate

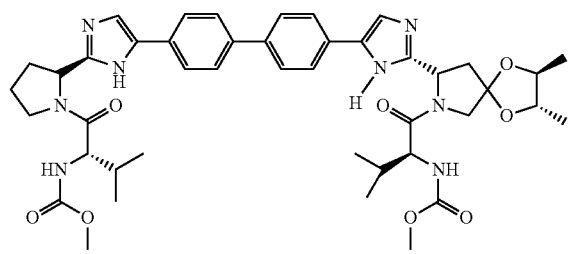

$^1$H NMR (400 MHz, DMSO-d6) δ □ppm 0.70-0.96 (m, 7H), 1.12-1.35 (m, 4H), 1.85-2.04 (m, 3H), 2.04-2.25 (m, 2H), 2.31-2.47 (m, 1H), 3.33 (s, 7H), 3.45-3.61 (m, 8H), 3.63-3.89 (m, 7H), 3.94-4.15 (m, 4H), 4.91-5.17 (m, 2H), 7.20-7.40 (m, 2H), 7.49-7.59 (m, 1H), 7.60-7.70 (m, 2H), 7.70-7.81 (m, 2H), 7.81-7.93 (m, 2H), 7.96-8.08 (m, 0H), 11.59-12.00 (m, 2H); LC-MS (ESI): m/z 825.5 (M+H)$^+$; HRMS: (M+H)$^+$ calcd, 825.4299. found, 825.4302.

Intermediate 36: (8S)-7-{[(phenylmethyl)oxy]carbonyl}-1,4-dithia-7-azaspiro[4.4]nonane-8-carboxylic acid

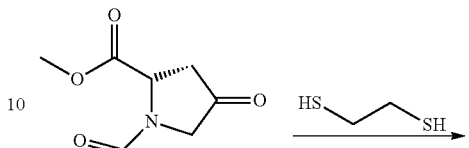

Intermediate 35: 8-methyl 7-(phenylmethyl) (8S)-1,4-dithia-7-azaspiro[4.4]nonane-7,8-dicarboxylate To a stirred solution of 2-methyl 1-(phenylmethyl) (2S)-4-oxo-1,2-pyrrolidinedicarboxylate (Intermediate 23) (680 mg, 2.452 mmol) in anhydrous DCM (50 mL) was added 1,2-ethanethiodiol (462 mg, 4.9 mmol) and followed by addition of BF$_3$ etherate (139 mg, 0.4 mmol). The resulting mixture was stirred overnight at rt. before quenched with NaHCO$_3$ (ss). Layers were separated and the organic layer was dried, filtered and evaporated. The residue was purified by column chromatography (silica gel, 0 to 50% ethyl acetate in hexane) to give 8-methyl 7-(phenylmethyl) (8S)-1,4-dithia-7-azaspiro[4.4]nonane-7,8-dicarboxylate (Intermediate 35) as an oil. $^1$H NMR (400 MHz, CHLOROFORM-d) δ ppm 7.28-7.48 (m, 5H) 4.95-5.35 (m, 2H) 4.34-4.63 (m, 1H) 3.90-4.11 (m, 1H) 3.82-3.90 (m, 1H) 3.78 (s, 2H) 3.50-3.69 (m, 1H) 3.15-3.45 (m, 4H) 2.74 (ddd, J=13.30, 7.78, 1.25 Hz, 1H) 2.40-2.64 (m, 1H). ES LC-MS m/z=354.2 (M+H).

Intermediate 36: (8S)-7-{[(phenylmethyl)oxy]carbonyl}-1,4-dithia-7-azaspiro[4.4]nonane-8-carboxylic acid

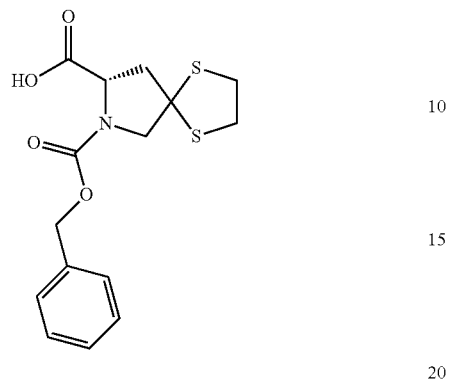

(8S)-7-{[(Phenylmethyl)oxy]carbonyl}-1,4-dithia-7-azaspiro[4.4]nonane-8-carboxylic (Intermediate 36) acid (36) (640 mg, yield: 84%) was obtained from 8-methyl 7-(phenylmethyl) (8S)-1,4-dithia-7-azaspiro[4.4]nonane-7,8-dicarboxylate (798 mg, 2.25 mmol) and LiOH (60 mg, 2.5 mmol), following the procedure outlined in the preparation of intermediate 2. ES LC-MS m/z=340.1 (M+H).

Intermediate 39: Preparation of methyl [(1S)-1-({(2S)-2-[4-(4'-{2-[(8S)-1,4-dithia-7-azaspiro[4.4]non-8-yl]-1H-imidazol-4-yl}-4-biphenylyl)-1H-imidazol-2-yl]-1-pyrrolidinyl}carbonyl)-2-methylpropyl]carbamate

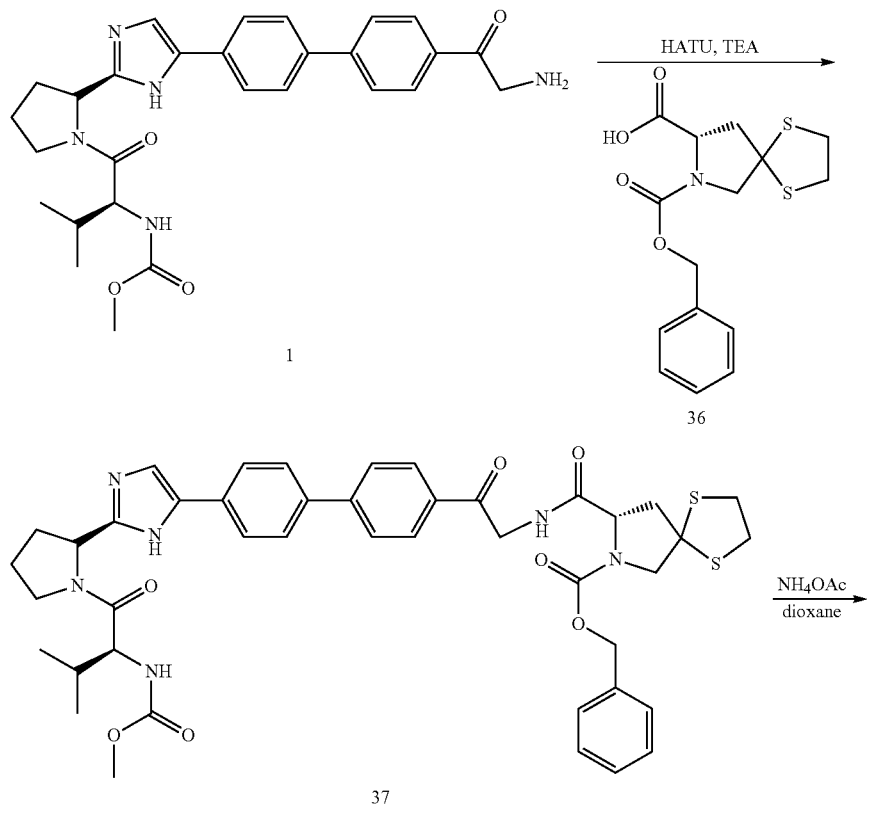

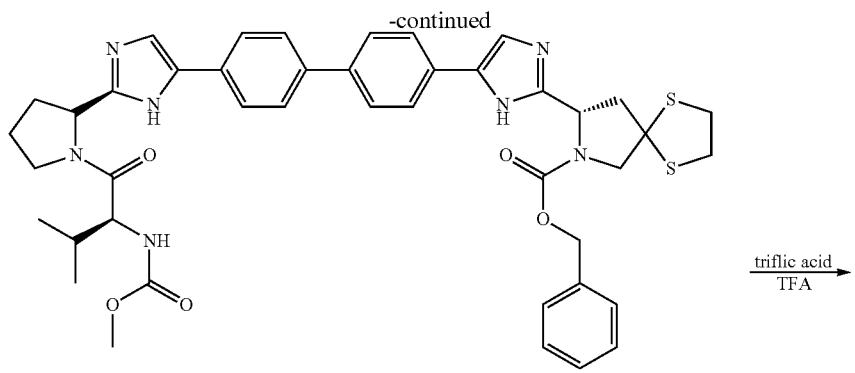

-continued

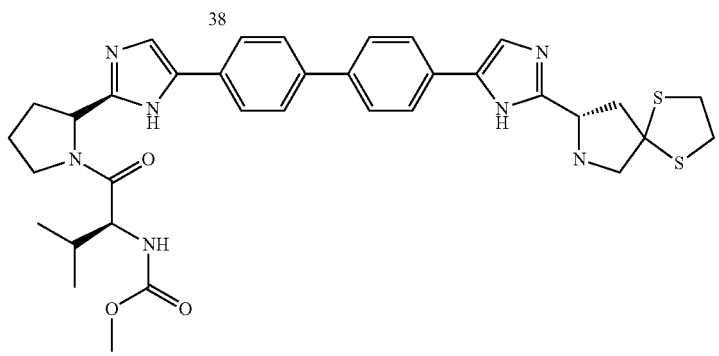

39

Intermediate 37: phenylmethyl(8S)-8-({[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]amino}carbonyl)-1,4-dithia-7-azaspiro[4.4]nonane-7-carboxylate

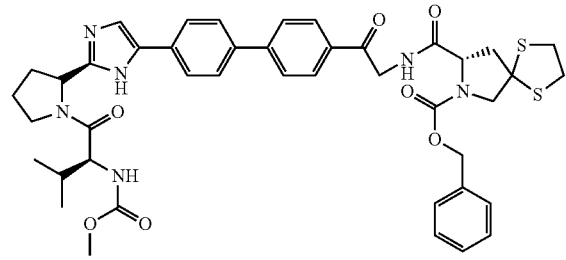

Phenylmethyl (8S)-8-({[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]amino}carbonyl)-1,4-dithia-7-azaspiro[4.4]nonane-7-carboxylate (Intermediate 37) (584 mg, yield 68%) was obtained from methyl {(1S)-1-[((2S)-2-{4-[4'-(aminoacetyl)-4-biphenylyl]-1H-imidazol-2-yl}-1-pyrrolidinyl)carbonyl]-2-methylpropyl}carbamate dihydrochloride (Intermediate 1) (603 mg, 1.046 mmol), (8S)-7-{[(phenylmethyl)oxy]carbonyl}-1,4-dithia-7-azaspiro[4.4]nonane-8-carboxylic acid (Intermediate 36) (355 mg, 1.046 mmol) and HATU (498 mg, 1.046 mmol), following similar procedure outlined in preparation of intermediate 21. $^1$H NMR (400 MHz, CHLOROFORM-d) δ ppm 7.88-8.03 (m, 2H) 7.45-7.85 (m, 6H) 7.05-7.45 (m, 6H) 5.61 (br. s., 1H) 4.98-5.41 (m, 2H) 4.42-4.92 (m, 2H) 4.35 (t, J=7.78 Hz, 1H) 3.93-4.06 (m, 1H) 3.86 (d, J=8.78 Hz, 3H) 3.62-3.80 (m, 4H) 3.35 (d, J=5.02 Hz, 4H) 3.21 (d, J=7.28 Hz, 1H) 2.61-2.96 (m, 2H) 2.24 (br. s., 2H) 1.93-2.16 (m, 2H) 0.98-1.17 (m, 3H) 0.91 (t, J=7.15 Hz, 6H). ES LC-MS m/z=825.2 (M+H).

Intermediate 38: phenylmethyl (8S)-8-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-1,4-dithia-7-azaspiro[4.4]nonane-7-carboxylate

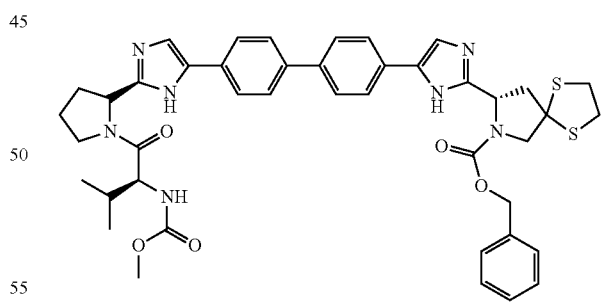

Phenylmethyl (8S)-8-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-1,4-dithia-7-azaspiro[4.4]nonane-7-carboxylate (Intermediate 38) (497 mg, 87%) was obtained from phenylmethyl (8S)-8-({[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]amino}carbonyl)-1,4-dithia-7-azaspiro[4.4]nonane-7-carboxylate (Intermediate 37) (584 mg, 0.71 mmol) and ammonium acetate (546 mg, 7.1 mmol), following the similar procedure outlined in the preparation of Intermediate (22). ES LC-MS m/z=806.4 (M+H).

Intermediate 39: methyl [(1S)-1-({(2S)-2-[4-(4'-{2-[(8S)-1,4-dithia-7-azaspiro[4.4]non-8-yl]-1H-imidazol-4-yl}-4-biphenylyl)-1H-imidazol-2-yl]-1-pyrrolidinyl}carbonyl)-2-methylpropyl]carbamate

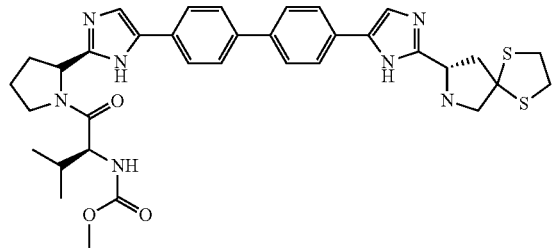

At rt, to a stirred solution of phenylmethyl (8S)-8-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-1,4-dithia-7-azaspiro[4.4]nonane-7-carboxylate (Intermediate 38) (497 mg, 0.617 mmol) in TFA (6 mL) was added triflic acid (278 mg, 1.85 mmol). The resulting mixture was stirred at rt for 3 hrs. Evaporated solvents, neutralized with NaHCO₃(SS) and the aqueous phase was extracted with DCM (15% IPA) (3×). The combined organic phases was dried, filtered and evaporated to give methyl [(1S)-1-({(2S)-2-[4-(4'-{2-[(8S)-1,4-dithia-7-azaspiro[4.4]non-8-yl]-1H-imidazol-4-yl}-4-biphenylyl)-1H-imidazol-2-yl]-1-pyrrolidinyl}carbonyl)-2-methylpropyl]carbamate (Intermediate 39) (400 mg, yield: 97%). ES LC-MS m/z=672.2 (M+H).

Example 12 methyl [(1S)-2-methyl-1-({(2S)-2-[4-(4'-{2-[(8S)-7-((2S)-3-methyl-2-{[(methyloxy)carbonyl]amino}butanoyl)-1,4-dithia-7-azaspiro[4.4]non-8-yl]-1H-imidazol-4-yl}-4-biphenylyl)-1H-imidazol-2-yl]-1-pyrrolidinyl}carbonyl)propyl]carbamate

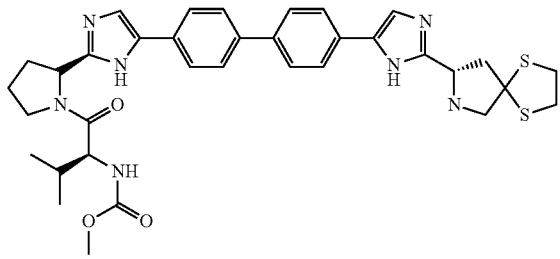

Methyl [(1S)-2-methyl-1-({(2S)-2-[4-(4'-{2-[(8S)-7-((2S)-3-methyl-2-{[(methyloxy)carbonyl]amino}butanoyl)-1,4-dithia-7-azaspiro[4.4]non-8-yl]-1H-imidazol-4-yl}-4-biphenylyl)-1H-imidazol-2-yl]-1-pyrrolidinyl}carbonyl)propyl]carbamate (88 mg, yield: 27%) was obtained from methyl [(1S)-1-({(2S)-2-[4-(4'-{2-[(8S)-1,4-dithia-7-azaspiro[4.4]non-8-yl]-1H-imidazol-4-yl}-4-biphenylyl)-1H-imidazol-2-yl]-1-pyrrolidinyl}carbonyl)-2-methylpropyl]carbamate (Intermediate 39) (250 mg, 0.372 mmol), N-[(methyloxy)carbonyl]-L-valine (65 mg, 0.372 mmol) and HATU (141 mg, 0.372 mmol), following the similar procedure outlined in Example 5. ¹H NMR (400 MHz, CHLOROFORM-d) δ ppm 10.07-11.08 (m, 2H) 7.82 (br. s., 3H) 7.58 (d, J=6.02 Hz, 5H) 7.10-7.30 (m, 2H) 5.54 (d, J=9.29 Hz, 2H) 5.17-5.42 (m, 3H) 4.01-4.48 (m, 2H) 3.23-4.03 (m, 10H) 2.70-3.19 (m, 2H) 2.30-2.49 (m, 1H) 1.91-2.29 (m, 4H) 1.19-1.56 (m, 4H) 1.07 (dd, J=10.54, 7.03 Hz, 2H) 0.58-0.97 (m, 10H). HRMS: (M+H)⁺ calcd: 829.3530. found: 829.3534.

Example 13 methyl[(1S)-2-methyl-1-({(2S)-2-[4-(4'-{2-[(8S)-7-((2S)-2-{[(methyloxy)carbonyl]amino}butanoyl)-1,4-dithia-7-azaspiro[4.4]non-8-yl]-1H-imidazol-4-yl}-4-biphenylyl)-1H-imidazol-2-yl]-1-pyrrolidinyl}carbonyl)propyl]carbamate

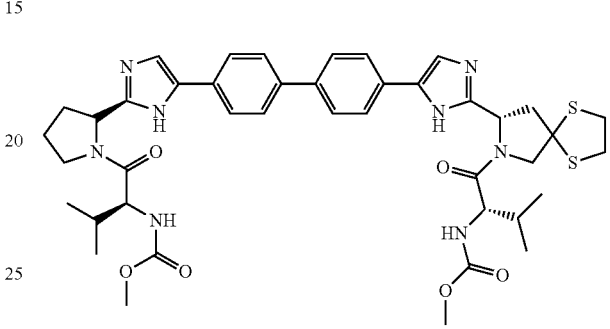

Methyl [(1S)-2-methyl-1-({(2S)-2-[4-(4'-{2-[(8S)-7-((2S)-2-{[(methyloxy)carbonyl]amino}butanoyl)-1,4-dithia-7-azaspiro[4.4]non-8-yl]-1H-imidazol-4-yl}-4-biphenylyl)-1H-imidazol-2-yl]-1-pyrrolidinyl}carbonyl)propyl]carbamate (35 mg, yield: 27%) was obtained from methyl [(1S)-1-({(2S)-2-[4-(4'-{2-[(8S)-1,4-dithia-7-azaspiro[4.4]non-8-yl]-1H-imidazol-4-yl}-4-biphenylyl)-1H-imidazol-2-yl]-1-pyrrolidinyl}carbonyl)-2-methylpropyl]carbamate (Intermediate 39) (100 mg, 0.149 mmol), (2S)-2-{[(methyloxy)carbonyl]amino}butanoic acid (24 mg, 0.15 mmol) and HATU (56.5 mg, 0.149 mmol), following the similar procedure outlined in Example 5. ¹H NMR (400 MHz, CHLOROFORM-d) δ ppm 9.99-11.64 (m, 2H) 7.53 (br. s., 8H) 7.12-7.34 (m, 2H) 5.26 (br. s., 2H) 3.18-4.64 (m, 17H) 2.79 (br. s., 2H) 1.43-2.62 (m, 8H) 0.70-1.19 (m, 9H). HRMS: (M+H)⁺ calcd: 815.3373. found: 815.3373.

Example 14 methyl [(1S)-2-methyl-1-({(2S)-2-[4-(4'-{2-[(8S)-7-({[(methyloxy)carbonyl]amino}acetyl)-1,4-dithia-7-azaspiro[4.4]non-8-yl]-1H-imidazol-4-yl}-4-biphenylyl)-1H-imidazol-2-yl]-1-pyrrolidinyl}carbonyl)propyl]carbamate

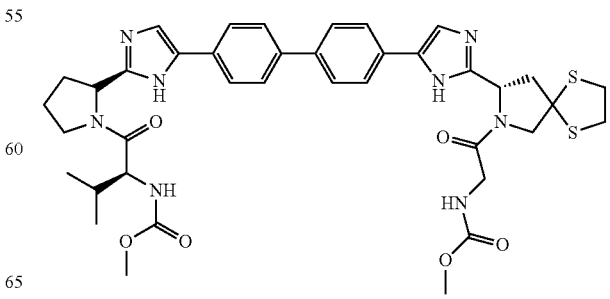

Methyl [(1S)-2-methyl-1-({(2S)-2-[4-(4'-{2-[(8S)-7-({[(methyloxy)carbonyl]amino}acetyl)-1,4-dithia-7-azaspiro[4.4]non-8-yl]-1H-imidazol-4-yl}-4-biphenylyl)-1H-imidazol-2-yl]-1-pyrrolidinyl}carbonyl)propyl]carbamate (14 mg, yield: 24%) was obtained from methyl [(1S)-1-({(2S)-2-[4-(4'-{2-[(8S)-1,4-dithia-7-azaspiro[4.4]non-8-yl]-1H-imidazol-4-yl}-4-biphenylyl)-1H-imidazol-2-yl]-1-pyrrolidinyl}carbonyl)-2-methylpropyl]carbamate (Intermediate 39) (50 mg, 0.074 mmol), N-[(methyloxy)carbonyl]glycine (10 mg, 0.074 mmol) and HATU (28.3 mg, 0.074 mmol), following the similar procedure outlined in Example 5. $^1$H NMR (400 MHz, CHLOROFORM-d) δ ppm 9.86-11.31 (m, 2H) 7.50 (br. s., 8H) 6.91-7.27 (m, 2H) 5.41-6.31 (m, 2H) 5.24 (br. s., 2H) 3.12-4.45 (m, 18H) 2.77 (br. s., 2H) 1.77-2.50 (m, 4H) 0.58-1.15 (m, 6H). HRMS: (M+H)$^+$ calcd: 787.3055. found: 787.3056.

Example 15 methyl [(1S)-2-methyl-1-({(2S)-2-[4-(4'-{2-[((2S)-3-methyl-2-{[(methyloxy)carbonyl]amino}butanoyl)-8-oxa-2-azaspiro[4.5]dec-3-yl]-1H-imidazol-4-yl}-4-biphenylyl)-1H-imidazol-2-yl]-1-pyrrolidinyl}carbonyl)propyl]carbamate

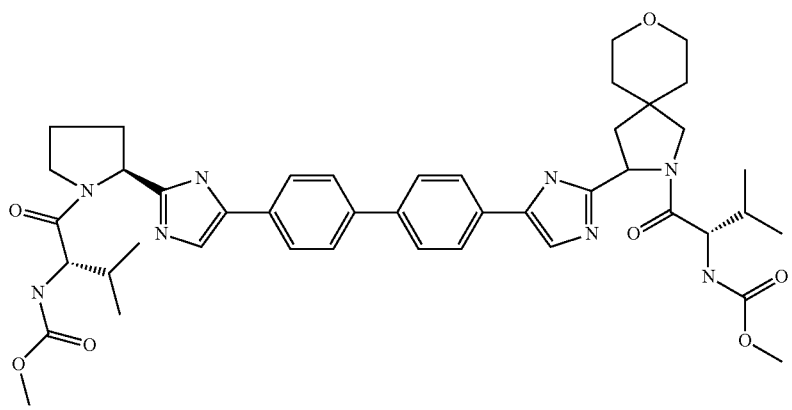 [SMILES: COC(=O)N[C@H](C(=O)N1CC2(CCOCC2)CC1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]

A solution of methyl ((1S)-2-methyl-1-{[(2S)-2-(4-{4'-[({[2-((2S)-3-methyl-2-{[(methyloxy)carbonyl]amino}butanoyl)-8-oxa-2-azaspiro[4.5]dec-3-yl]carbonyl}amino)acetyl]-4-biphenylyl}-1H-imidazol-2-yl)-1-pyrrolidinyl]carbonyl}propyl)carbamate (Intermediate 104) (131 mg, 0.16 mmol) and ammonium acetate (122 mg, 1.6 mmol) in dioxane (2 mL) was degassed and heated to 110° C. in a sealed tube for 18 h. The reaction was cooled to room temperature and diluted with ethyl acetate and filtered and concentrated in vacuo. The residue was purified by C$_{18}$ RP chromatography eluting with 10-90% water/acetonitrile/0.2% NH$_4$OH, to afford an off-white solid (44 mg, 34% yield). $^1$H NMR (400 MHz, METHANOL-d$_4$) δ ppm 7.55-7.87 (m, 8H) 7.32 (br. s., 4H) 5.02-5.23 (m, 3H) 4.13-4.34 (m, 4H) 3.93-4.04 (m, 1H) 3.88 (br. s., 2H) 3.49-3.84 (m, 8H) 1.86-2.54 (m, 10H) 1.45-1.84 (m, 4H) 0.69-1.12 (m, 12H). HRMS for C$_{44}$H$_{57}$N$_8$O$_7$ (M+H)$^+$ calc: 809.4350. found: 809.4346. Purity (LC-MS): 96%.

Preparation of Intermediate 104

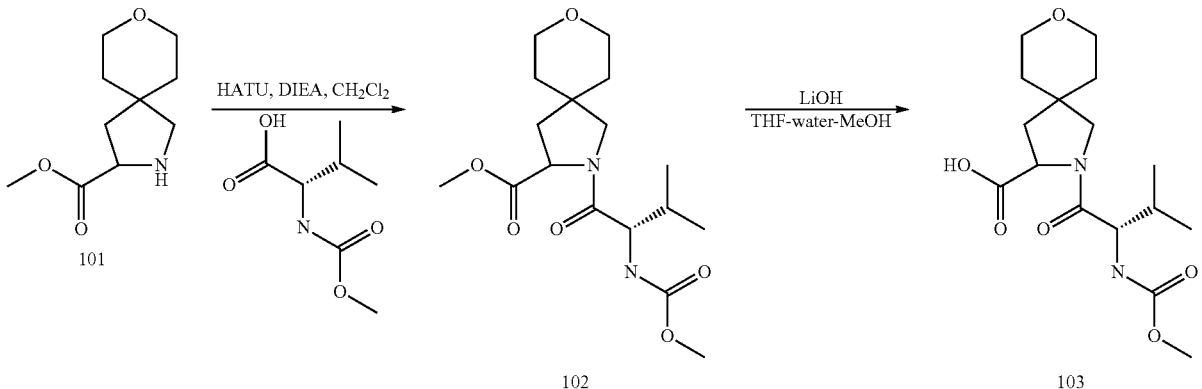

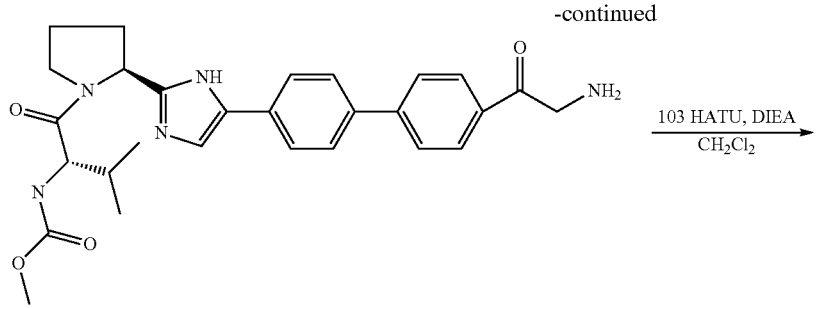

1

-continued

103 HATU, DIEA
———————→
CH₂Cl₂

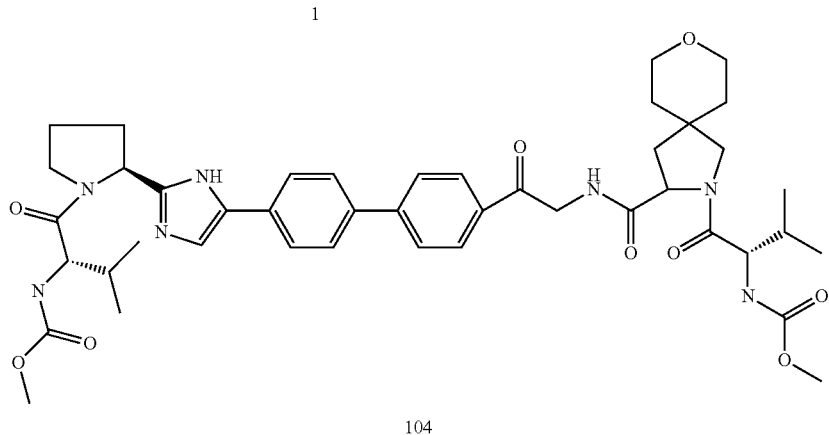

104

Intermediate 101: ethyl 8-oxa-2-azaspiro[4.5]decane-3-carboxylate

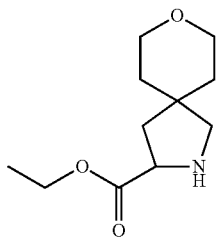

Intermediate 101 was obtained in quantitative yield as a racemate from tetrahydro-2H-pyran-4-carbaldehyde (1.0 g, 8.8 mmol) following the procedure outlined in WO 98/08850 pp. 50.

Intermediate 102: ethyl 2-{N-[(methyloxy)carbonyl]-L-valyl}-8-oxa-2-azaspiro[4.5]decane-3-carboxylate

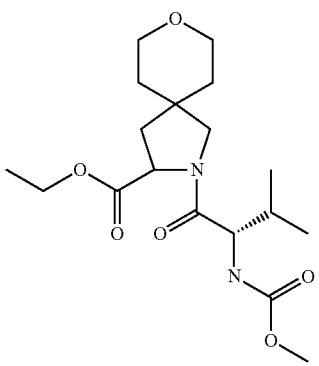 [SMILES: CCOC(=O)C1CC2(CCOCC2)CN1C(=O)[C@@H](NC(=O)OC)C(C)C]

To a solution of ethyl 8-oxa-2-azaspiro[4.5]decane-3-carboxylate (101) (200 mg, 0.94 mmol), HATU (392 mg, 1.03 mmol) and N-[(methyloxy)carbonyl]-L-valine (181 mg, 1.03 mmol) in anhydrous CH₂Cl₂ (6 mL) was added Hunig's base (0.33 mL, 1.88 mmol) and the solution stirred at rt under nitrogen. After 2 h, the reaction was concentrated in vacuo, purified by C₁₈ RP chromatography, eluting with 10-90% ACN/water/0.2% NH₄OH, to afford the product as a yellow oil (313 mg, 90% yield).

Intermediate 103: 2-{N-[(methyloxy)carbonyl]-L-valyl}-8-oxa-2-azaspiro[4.5]decane-3-carboxylic acid

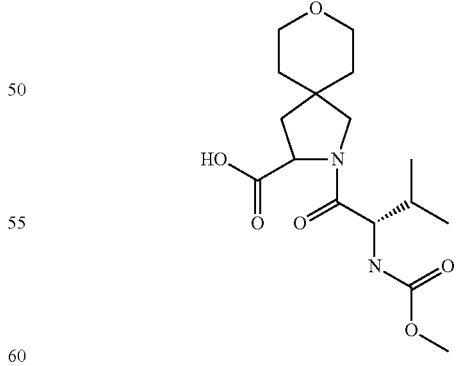

To a solution of ethyl 2-{N-[(methyloxy)carbonyl]-L-valyl}-8-oxa-2-azaspiro[4.5]decane-3-carboxylate (102) (310 mg, 0.84 mmol) in a 2:1:1 mixture of THF/water/methanol (6 mL) was added lithium hydroxide monohydrate (70 mg, 1.67 mmol) and the reaction stirred at room temperature for 2 h. Treated with 1 N HCl (1.6 mL), partitioned between EtOAc and water (30 mL each), organic layer extracted with EtOAc (30 mL), dried (MgSO₄) and concentrated to give a white foam (211 mg, 74% yield). This material was used in subsequent steps without additional purification. ¹H NMR (400 MHz, DMSO-d₆) δ ppm 12.43 (br. s., 1H) 7.19-7.41 (m, 1H) 4.05-4.28 (m, 1H) 3.91-4.05 (m, 2H) 3.40-3.71 (m, 6H) 3.20-3.28 (m, 1H) 1.81-1.98 (m, 2H) 1.70-1.80 (m, 1H) 1.46-1.69 (m, 2H) 1.32-1.46 (m, 1H) 0.65-1.03 (m, 10H).

Intermediate 104: methyl ((1S)-2-methyl-1-{[(2S)-2-(4-{4'-[({[2-((2S)-3-methyl-2-{[(methyloxy)carbonyl]amino}butanoyl)-8-oxa-2-azaspiro[4.5]dec-3-yl]carbonyl}amino)acetyl]-4-biphenylyl}-1H-imidazol-2-yl)-1-pyrrolidinyl]carbonyl}propyl)carbamate

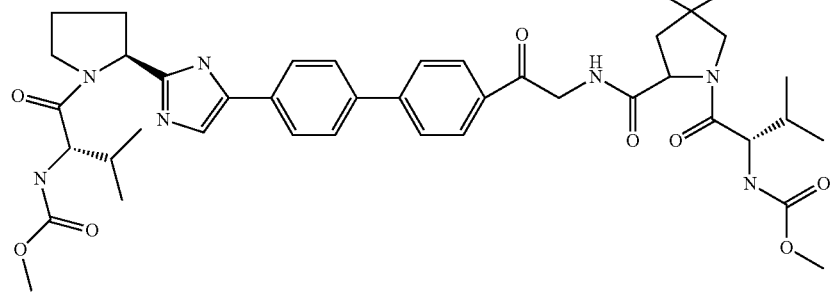

To a solution of 2-{N-[(methyloxy)carbonyl]-L-valyl}-8-oxa-2-azaspiro[4.5]decane-3-carboxylic acid (103) (100 mg, 0.29 mmol), HATU (111 mg, 0.29 mmol) and methyl {(1S)-1-[((2S)-2-{4-[4'-(aminoacetyl)-4-biphenylyl]-1H-imidazol-2-yl}-1-pyrrolidinyl)carbonyl]-2-methylpropyl}carbamate dihydrochloride (1) (168 mg, 0.29 mmol), prepared as described in Example 1 in anhydrous CH₂Cl₂ (2 mL), was added Hunig's base (0.2 mL, 1.17 mmol) and the solution stirred at rt under nitrogen. After 1 h, the reaction was concentrated in vacuo, purified by C₁₈ RP chromatography, eluting with 10-90% ACN/water/0.2% NH₄OH, to afford the product as a yellow solid (133 mg, 55% yield).

Example 16 methyl [(1S)-2-methyl-1-({(2S)-2-[4-(4'-{2-[2-((2S)-3-methyl-2-{[(methyloxy)carbonyl]amino}butanoyl)-8,8-dioxido-8-thia-2-azaspiro[4.5]dec-3-yl]-1H-imidazol-4-yl}-4-biphenylyl)-1H-imidazol-2-yl]-1-pyrrolidinyl}carbonyl)propyl]carbamate

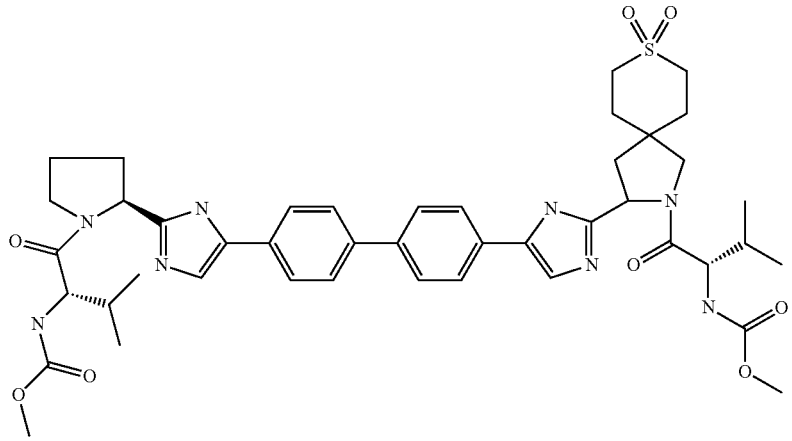 [SMILES: COC(=O)N[C@H](C(=O)N1CC2(CCS(=O)(=O)CC2)CC1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]

A solution of methyl ((1S)-2-methyl-1-{[(2S)-2-(4-{4'-[({[2-((2S)-3-methyl-2-{[(methyloxy)carbonyl]amino}butanoyl)-8,8-dioxido-8-thia-2-azaspiro[4.5]dec-3-yl]carbonyl}amino)acetyl]-4-biphenylyl}-1H-imidazol-2-yl)-1-pyrrolidinyl]carbonyl}propyl)carbamate (108) (107 mg, 0.12 mmol) and ammonium acetate (94 mg, 1.2 mmol) in dioxane (1.5 mL) was degassed with nitrogen and heated to 110° C. in a sealed tube for 18 h. The reaction was cooled to room temperature and diluted with ethyl acetate and filtered and concentrated in vacuo. Purified by SFC to afford the product as a tan solid (39 mg, 37% yield). $^1$H NMR (400 MHz, METHANOL-$d_4$) δ ppm 7.64 (br. s., 10H) 7.32 (br. s., 2H) 5.05-5.24 (m, 1H) 4.04-4.29 (m, 1H) 3.99 (br. s., 1H) 3.81 (br. s., 1H) 3.55-3.73 (m, 6H) 3.03-3.25 (m, 4H) 1.80-2.47 (m, 14H) 0.68-1.06 (m, 16H). HRMS for $C_{44}H_{57}N_8O_8S$ (M+H)$^+$ calc: 857.4020. found: 857.4020. Purity (LC-MS): 97%.

Preparation of Intermediate 108

Intermediate 105: ethyl 8-thia-2-azaspiro[4.5]decane-3-carboxylate 8,8-dioxide

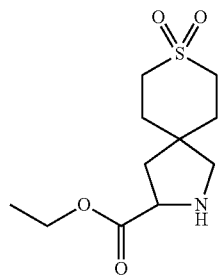 [SMILES: CCOC(=O)C1CC2(CCS(=O)(=O)CC2)CN1]

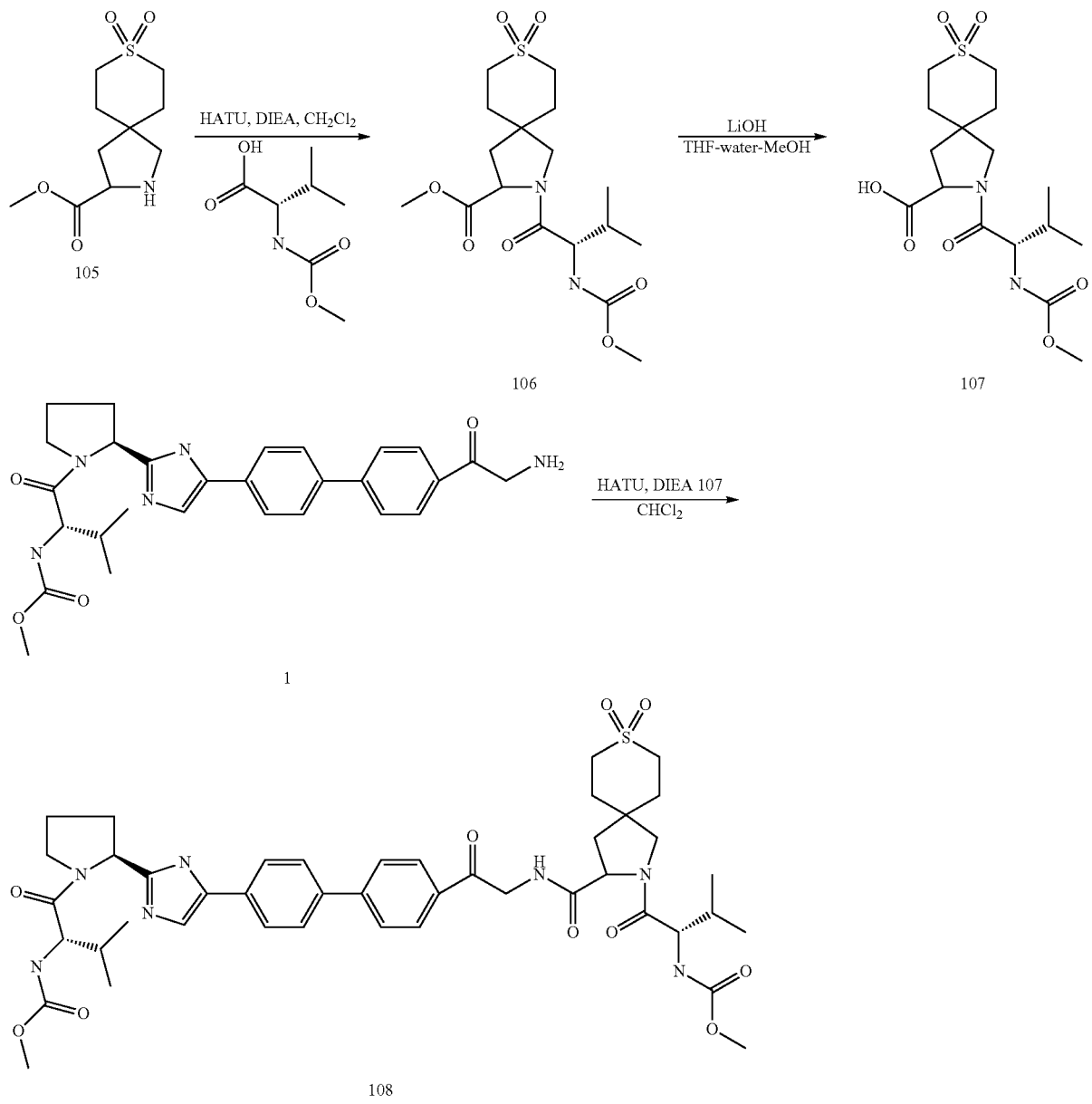

This compound was prepared in 90% yield from tetrahydro-2H-thiopyran-4-carbaldehyde 1,1-dioxide (1.05 g, 6.47 mmol) in an analogous fashion to Example 15.

Intermediate 106: ethyl 2-{N-[(methyloxy)carbonyl]-L-valyl}-8-thia-2-azaspiro[4.5]decane-3-carboxylate 8,8-dioxide

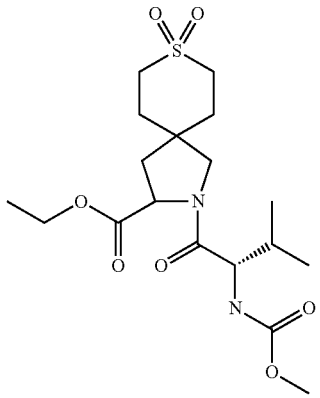 [SMILES: CCOC(=O)C1CC2(CCS(=O)(=O)CC2)CN1C(=O)[C@@H](NC(=O)OC)C(C)C]

Intermediate 106 was prepared in 60% yield from ethyl 8-thia-2-azaspiro[4.5]decane-3-carboxylate 8,8-dioxide (105) (200 mg, 0.77 mmol) in an analogous fashion to Example 15.

Intermediate 107: 2-{N-[(methyloxy)carbonyl]-L-valyl}-8-thia-2-azaspiro[4.5]decane-3-carboxylic acid 8,8-dioxide

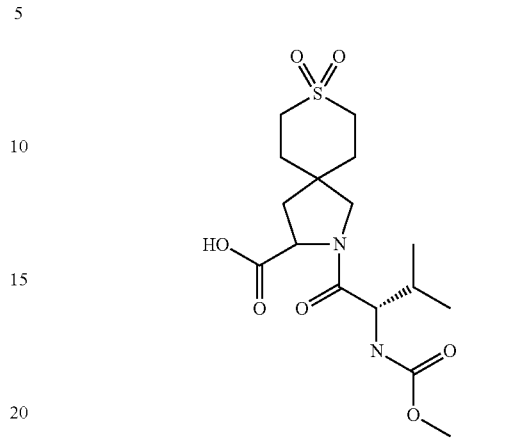

Intermediate 107 was prepared in quantitative yield from ethyl 2-{N-[(methyloxy)carbonyl]-L-valyl}-8-thia-2-azaspiro[4.5]decane-3-carboxylate 8,8-dioxide (106) (187 mg, 0.45 mmol) in an analogous fashion to Example 15. Used in subsequent steps without additional purification. $^1$H NMR (400 MHz, DMSO-d$_6$) δ ppm 12.48 (br. s., 1H) 7.13-7.44 (m, 1H) 4.10-4.31 (m, 1H) 3.46-3.61 (m, 3H) 2.93-3.24 (m, 3H) 2.32 (dd, J=3.7, 1.76 Hz, 1H) 1.93-2.13 (m, 3H) 1.73-1.94 (m, 2H) 1.55-1.71 (m, 1H) 0.66-1.04 (m, 10H).

Intermediate 108: methyl ((1S)-2-methyl-1{[(2S)-2-(4-{4'-[({[2-((2S)-3-methyl-2-{[(methyloxy)carbonyl]amino}butanoyl)-8,8-dioxido-8-thia-2-azaspiro[4.5]dec-3-yl]carbonyl}amino)acetyl]-4-biphenylyl}-1H-imidazol-2-yl)-1-pyrrolidinyl]carbonyl}propyl)carbamate

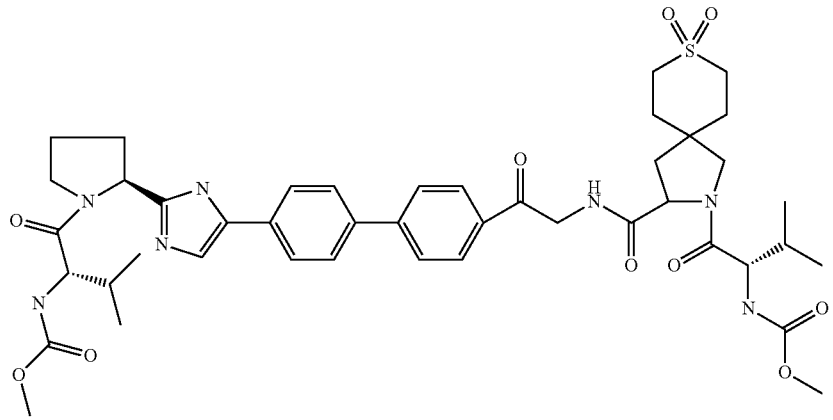 [SMILES: COC(=O)N[C@H](C(=O)N1CC2(CCS(=O)(=O)CC2)CC1C(=O)NCC(=O)c1ccc(-c2ccc(-c3cnc([C@@H]4CCCN4C(=O)[C@@H](NC(=O)OC)C(C)C)[nH]3)cc2)cc1)C(C)C]

Prepared in 49% yield from 2-{N-[(methyloxy)carbonyl]-L-valyl}-8-thia-2-azaspiro[4.5]decane-3-carboxylic acid 8,8-dioxide (107) (100 mg, 0.26 mmol) and methyl {(1S)-1-[((2S)-2-{4-[4'-(aminoacetyl)-4-biphenylyl]-1H-imidazol-2-yl}-1-pyrrolidinyl)carbonyl]-2-methylpropyl}carbamate dihydrochloride (1) (148 mg, 0.26 mmol), in an analogous fashion as described in Example 15.

Example 17 methyl [(1S)-1-({(2S)-2-[4-(4'-{2-[8,8-difluoro-2-((2S)-3-methyl-2-{[(methyloxy)carbonyl]amino}butanoyl)-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate

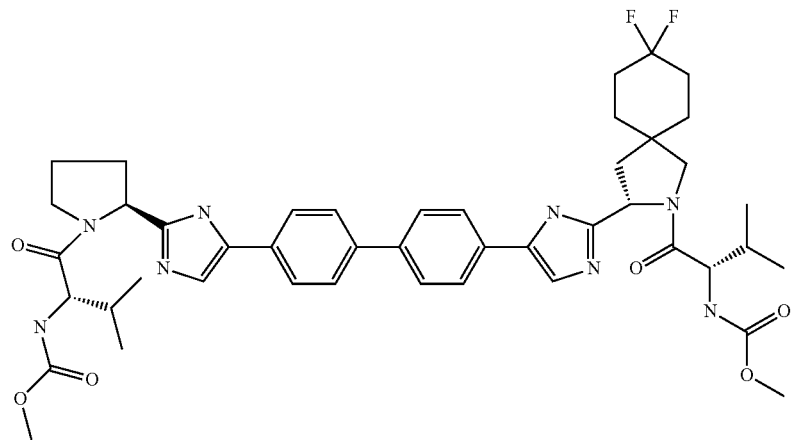 [SMILES: COC(=O)N[C@H](C(=O)N1CCC[C@H]1c1ncc(-c2ccc(-c3ccc(-c4cnc([C@@H]5CC6(CCC(F)(F)CC6)CN5C(=O)[C@@H](NC(=O)OC)C(C)C)[nH]4)cc3)cc2)[nH]1)C(C)C]

A solution of ammonium acetate (540 mg, 6.9 mmol) and 2-{4'-[({[(2S)-1-((2S)-3-methyl-2-{[(methyloxy)carbonyl]amino}butanoyl)-2-pyrrolidinyl]carbonyl}oxy)acetyl]-4-biphenylyl}-2-oxoethyl (3S)-8,8-difluoro-2-((2S)-3-methyl-2-{[(methyloxy)carbonyl]amino}butanoyl)-2-azaspiro[4.5]decane-3-carboxylate (Intermediate 117) (307 mg, 0.35 mmol) in anhydrous dioxane (3.5 mL) was degassed with nitrogen and heated to 110° C. in a sealed tube for 3 h. The reaction was cooled to room temperature and partitioned between EtOAc and sat. NaHCO₃ (35 mL each), the organic layer was washed with brine and dried (MgSO₄) and concentrated in vacuo. The residue was purified by C₁₈ reverse phase chromatography eluting with 10-100% acetonitrile/water/0.2% NH₄OH to afford the title compound as a yellow solid (235 mg, 80% yield). ¹H NMR (400 MHz, METHANOL-d₄) □□ppm 7.69-7.82 (m, 3H) 7.63 (br. s., 5H) 7.17-7.37 (m, 2H) 5.03-5.19 (m, 1H) 4.20 (br. s., 1H) 4.06-4.16 (m, 1H) 3.96 (br. s., 1H) 3.85 (br. s., 1H) 3.62 (d, J=3.1 Hz, 6H) 2.24-2.38 (m, 3H) 2.15 (br. s., 3H) 1.85-2.09 (m, 8H) 1.77-1.85 (m, 2H) 1.53-1.76 (m, 3H) 0.96 (br. s., 4H) 0.87 (d, J=6.3 Hz, 12H). HRMS for $C_{45}H_{57}N_8O_6F_2$ (M+H)⁺ calc: 843.4369. found: 843.4371. Purity (LC-MS): 97%.

Preparation of Intermediate 70

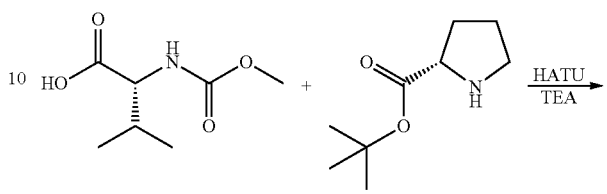

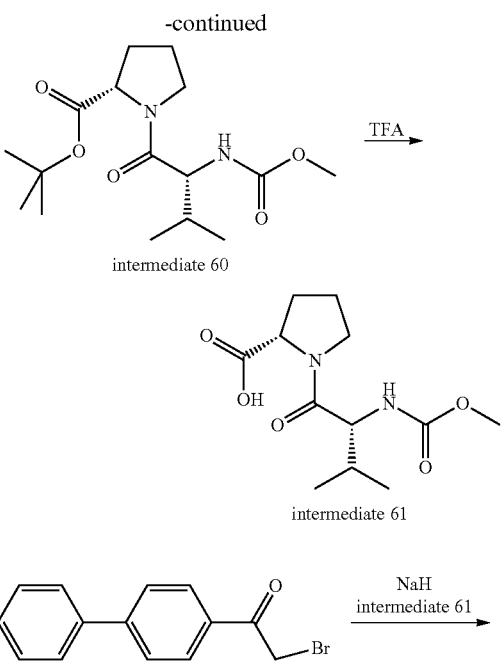

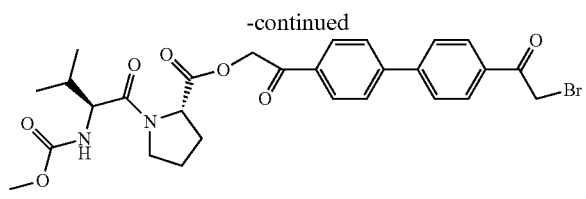

intermediate 70

Intermediate 60

(2S)-2-{[((2S)-2-{[(1,1-dimethylethyl)oxy]carbonyl}-1-pyrrolidinyl)carbonyl]amino}-3-methylbutanoic acid (24.57 g, 143 mmol) and N-[(methyloxy)carbonyl]-L-valine (25.1 g, 143 mmol) were dissolved in DCM (50 mL). DIPEA (75 mL, 430 mmol) and HOBT (21.97 g, 143 mmol) were added. After 5 min EDC (27.5 g, 143 mmol) was added. The reaction was stirred at rt for 3 h. Diluted with water (50 mL) and 1N HCl (1 mL) was added. The precipitate was filtered off and organic/aqueous layers were filtered through a hydrophobic frit and concentrated to dryness to afford 42.92 g of a colorless oil.

Intermediate 61

1,1-dimethylethyl N-[(methyloxy)carbonyl]-L-valyl-L-prolinate (61 g, 186 mmol) was dissolved in HCl (50 ml, 1646 mmol) (150 mL0 of a 4M sol) and stirred for 5 h. Concentrated to dryness to afford 47.9 g of product as a light yellow sticky foam.

Intermediate 70

1,1'-(4,4'-biphenyldiyl)bis(2-bromoethanone) (37.8 g, 95 mmol) was dissolved in DMF (800 mL) and degassed for 15 min (N2). Intermediate 61 (21.99 g, 81 mmol) was dissolved in DMF (100 mL), followed by careful addition of NaH (2.94 g, 73.4 mmol, 60% in oil) under nitrogen over 15 min. The solution was stirred under N2 for 15 min, then slowly added over 15 min drop-wise to a solution of 1,1'-(4,4'-biphenyldiyl)bis(2-bromoethanone), followed by stirring for 1 h at RT. Solvent volume was then reduced in vacuo to ~100 mL and cooled to 20° C. 100 mL of water was slowly added and resulting slight grey-yellow solid was filtered and washed with water (200 mL), hexane (200 mL) and dried under the vacuum (12 h). The crude compound was purified on 500 g of silica with hexane/ethyl acetate (increasing gradient from 50% to 100% EA), yielding 14.5 g (37.3%) of Intermediate 70. $^1$H NMR (400 MHz, DMSO-$d_6$) δ ppm 8.11 (dd, J=12.0, 8.5 Hz, 4H) 7.96 (d, J=8.4 Hz, 4H) 7.41 (d, J=8.4 Hz, 1H) 5.43-5.75 (m, 2H) 4.99 (s, 2H) 4.53 (dd, J=8.6, 4.7 Hz, 1H) 4.03 (t, J=8.6 Hz, 1H) 3.76-3.90 (m, 1H) 3.60-3.73 (m, 1H) 3.53 (s, 3H) 2.22-2.37 (m, 1H) 2.12-2.21 (m, 1H) 1.85-2.06 (m, 3H) 0.90 (dd, J=10.7, 6.6 Hz, 6H).

Preparation of Intermediate 117

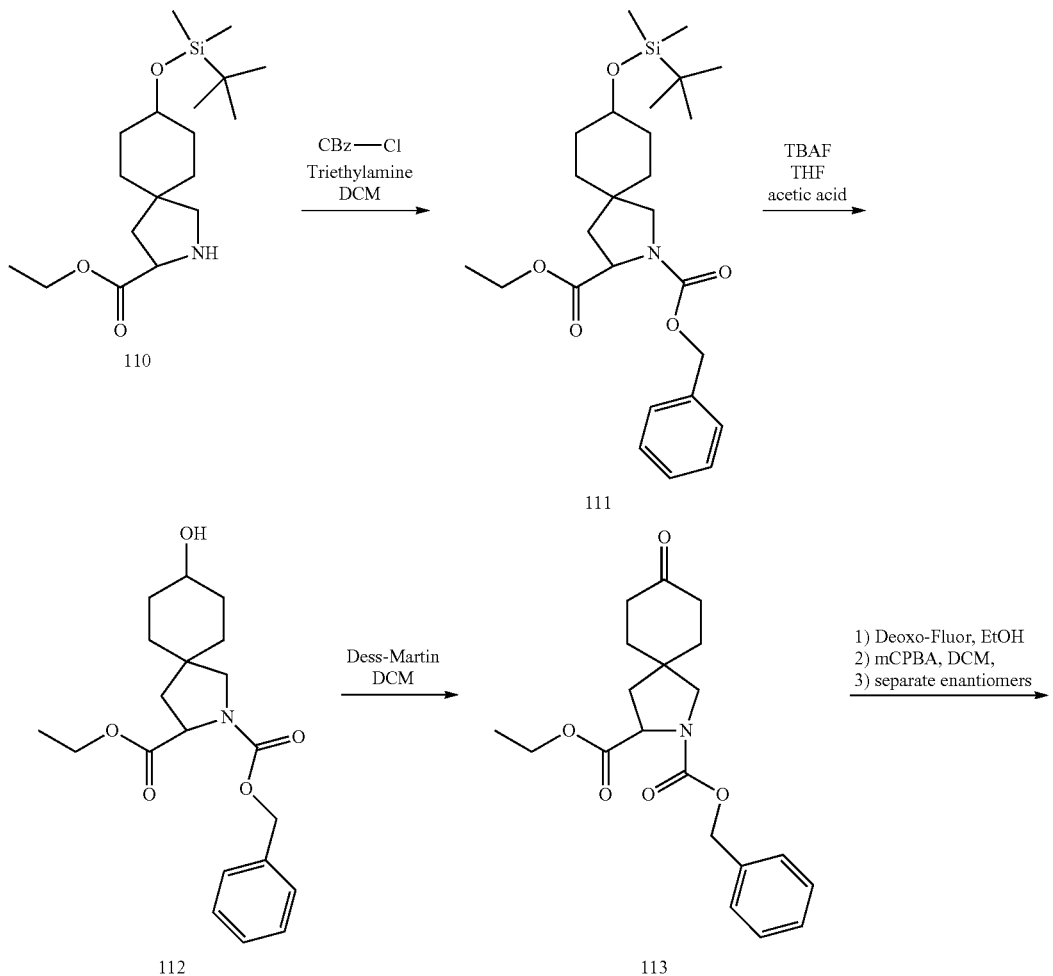

-continued
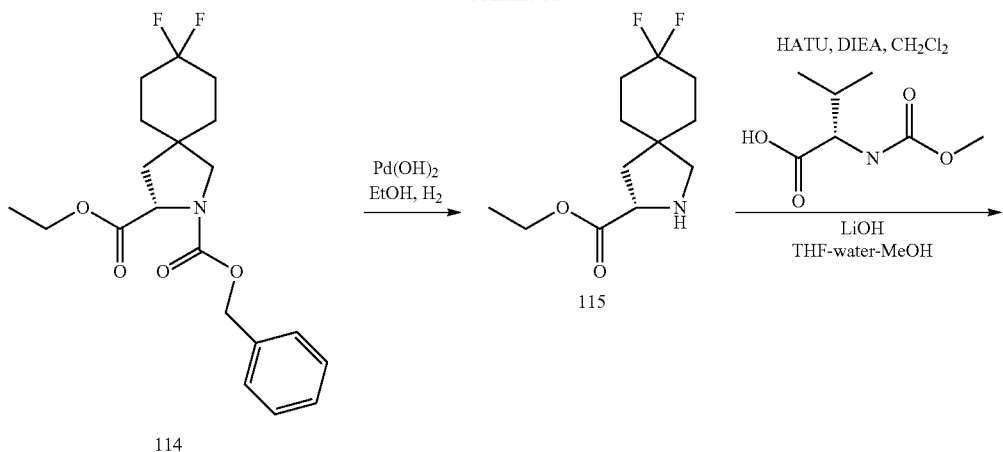
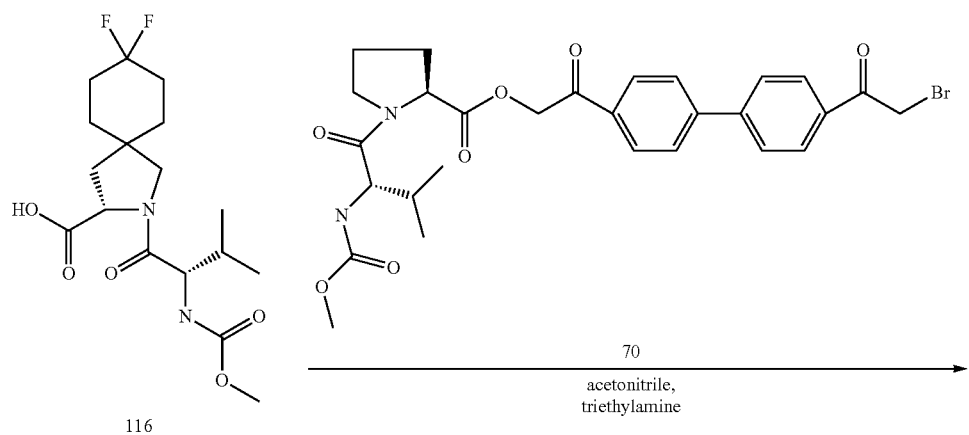
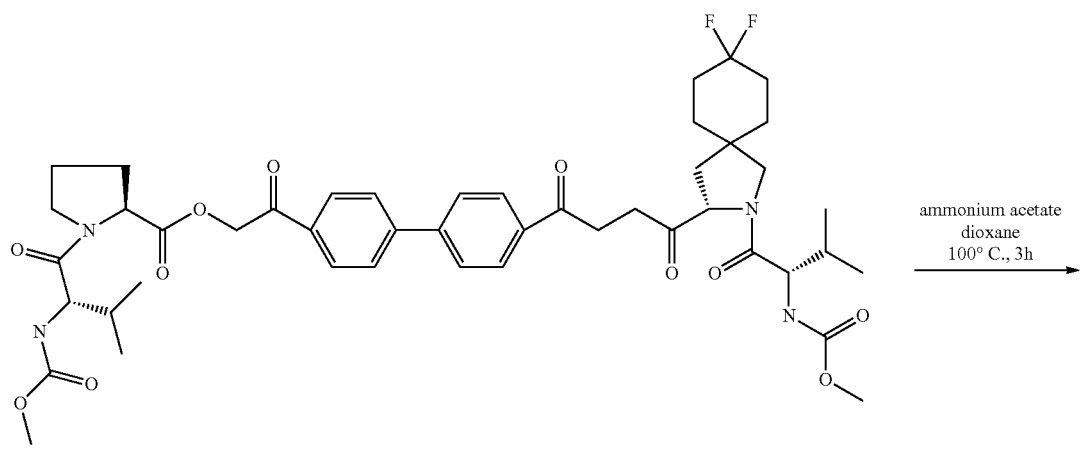

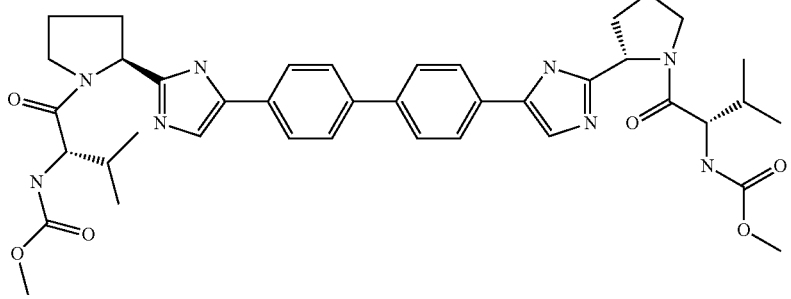

example 17

Intermediate 110: ethyl 8-{[(1,1-dimethylethyl)(dimethyl)silyl]oxy}-2-azaspiro[4.5]decane-3-carboxylate

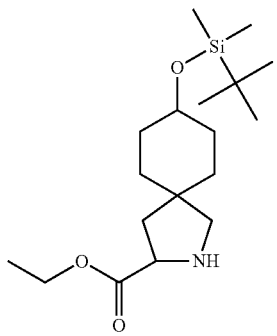 [SMILES: CCOC(=O)C1CC2(CCC(O[Si](C)(C)C(C)(C)C)CC2)CN1]

This compound was obtained in 98% yield as a racemate from 4-{[(1,1-dimethylethyl)(dimethyl)silyl]oxy}cyclohexanecarbaldehyde (mixture of cis/trans isomers) (7.35 g, 30.3 mmol) in an analogous fashion to Example 15.

Intermediate 111: 3-ethyl 2-(phenylmethyl) 8-{[(1,1-dimethylethyl)(dimethyl)silyl]oxy}-2-azaspiro[4.5]decane-2,3-dicarboxylate

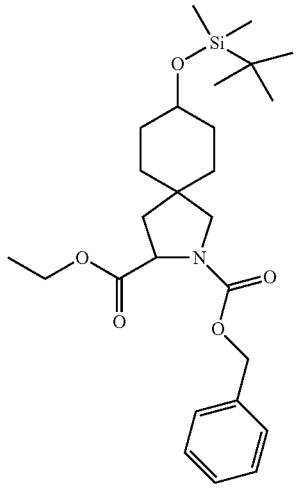 [SMILES: CCOC(=O)C1CC2(CCC(O[Si](C)(C)C(C)(C)C)CC2)CN1C(=O)OCc1ccccc1]

To a solution of ethyl 8-{[(1,1-dimethylethyl)(dimethyl)silyl]oxy}-2-azaspiro[4.5]decane-3-carboxylate (110) (10.61 g, 31.3 mmol) dissolved in dry DCM, triethylamine was added (10.8 mL, 78 mmol), cooled to 0° C. followed by the addition of Cbz-Cl (6.2 mL, 43.5 mmol), and the reaction stirred at 0° C., for 5 min, rt for 1 h. Reaction diluted with DCM (700 mL), washed with 0.1N HCl (700 mL), dried (MgSO$_4$) and concentrated in vacuo. The residue was purified by silica gel chromatography eluting with 10-60% hexanes/EtOAc to afford the title compound as a yellow oil (5.73 g, 39% yield).

Intermediate 112: 3-ethyl 2-(phenylmethyl) 8-hydroxy-2-azaspiro[4.5]decane-2,3-dicarboxylate

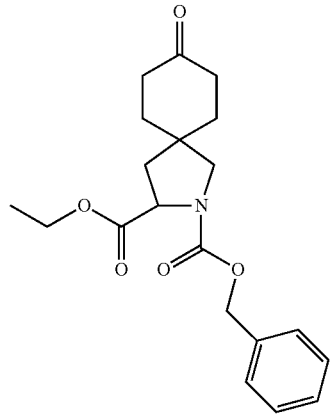 [SMILES: CCOC(=O)C1CC2(CCC(=O)CC2)CN1C(=O)OCc1ccccc1]

To a solution of 3-ethyl 2-(phenylmethyl) 8-{[(1,1-dimethylethyl)(dimethyl)silyl]oxy}-2-azaspiro[4.5]decane-2,3-dicarboxylate (111) (5.73 g, 12.05 mmol) in THF (60 mL) was added glacial acetic acid (1.38 mL, 24.0 mmol) followed by TBAF (24 mL) as a 1 M solution in THF. The reaction was stirred at room temperature for 72 h. The reaction was partitioned between EtOAc and water (250 mL) each, the organic layer was separated and washed with saturated NaHCO$_3$ (100 mL) and dried (MgSO$_4$) and concentrated in vacuo. The reaction was found to be incomplete by TLC. The residue was dissolved in dry THF (60 mL), cooled to 0° C. and treated with HF-pyridine (1.6 mL, 18.0 mmol), warmed to room temperature and stirred for 2 h under nitrogen. The reaction was poured into saturated NaHCO₃ (100 mL) and solid potassium carbonate was added until gas evolution ceased. Extracted with EtOAc (2×150 mL), the organic layers were combined and washed with 0.1 N HCl (100 mL), dried (MgSO₄) and concentrated in vacuo to afford the title compound in quantitative yield as a yellow oil which was used in subsequent reactions without additional purification.

Intermediate 113: 3-ethyl 2-(phenylmethyl) 8-oxo-2-azaspiro[4.5]decane-2,3-dicarboxylate

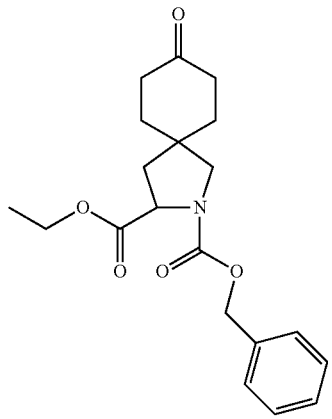

To a solution of 3-ethyl 2-(phenylmethyl) 8-hydroxy-2-azaspiro[4.5]decane-2,3-dicarboxylate (112) (4.36 g, 120.05 mmol) in dry DCM (60 mL) was added Dess-Martin Periodinane (10.22 g, 24.1 mmol) and the reaction stirred at rt under nitrogen for 18 h. The reaction was poured into 10% aq sodium thiosulfate (150 mL) and sat. NaHCO₃ (150 mL) and stirred for 10 min. Extracted with DCM (2×150 mL), dried (MgSO₄) and concentrated in vacuo. The residue was purified by silica gel chromatography eluting with 25-80% hexanes/EtOAc to afford the title compound as a pale yellow oil (2.89 g, 67% yield).

Intermediate 114: 3-ethyl 2-(phenylmethyl) (3S)-8,8-difluoro-2-azaspiro[4.5]decane-2,3-dicarboxylate

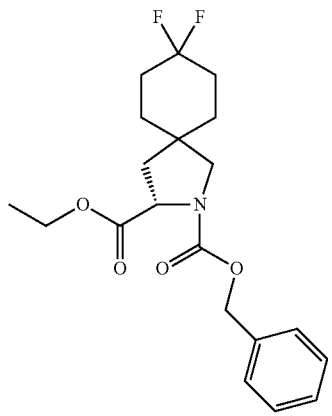 [SMILES: CCOC(=O)[C@@H]1CC2(CCC(F)(F)CC2)CN1C(=O)OCc1ccccc1]

To a solution of 3-ethyl 2-(phenylmethyl) 8-oxo-2-azaspiro[4.5]decane-2,3-dicarboxylate (113) (2.89 g, 7.13 mmol) in anhydrous CH₂Cl₂ (50 mL) was added Deoxo-Fluor (2.2 mL, 12.1 mmol) followed by a catalytic amount of ethanol and the reaction stirred at rt under nitrogen. After 2.5 h the reaction is poured into sat NaHCO₃ (150 mL), stirred for 10 min. Extracted with DCM (2×150 mL), and the organic layer was washed with 0.1 N HCl (100 mL), dried (MgSO₄) and concentrated in vacuo to afford the desired compound as a yellow oil (3.01 g) which was found to be contaminated with 3-ethyl 2-(phenylmethyl) (3S)-8-fluoro-2-azaspiro[4.5]dec-7-ene-2,3-dicarboxylate in a 1:1 ratio. The residue was dissolved in dry DCM (35 mL), and treated with mCPBA (77%, 1.66 g, 7.45 mmol) and stirred under nitrogen for 18 h. The reaction was poured into saturated NaHCO₃ (40 mL) and 10% aqueous sodium thiosulfate (40 mL) and stirred for 10 min. Extracted with DCM (100 mL) and dried (MgSO₄) and concentrated in vacuo. The residue was purified by silica gel chromatography eluting with 5-50% hexanes/EtOAc. The racemate was then separated by chiral HPLC on a 10 μm OD column eluting with 25% isopropanol in hexanes to afford the title compound as a clear oil (632 mg, 23% yield). The absolute configurations were determined by vibrational circular dichroism (VCD).
¹H NMR (400 MHz, CHLOROFORM-d) δ ppm 7.28-7.41 (m, 5H) 4.98-5.23 (m, 2H) 4.37 (ddd, J=19.3, 8.1, 8.0 Hz, 1H) 4.22 (q, J=7.2 Hz, 1H) 3.93-4.12 (m, 1H) 3.45-3.70 (m, 1H) 3.36 (dd, J=10.8, 2.0 Hz, 1H) 2.22 (dd, J=12.8, 8.5 Hz, 1H) 1.79-2.03 (m, 4H) 1.59-1.78 (m, 4H) 1.56 (br. s., 1H) 1.28 (t, J=7.1 Hz, 1H) 1.22 (d, J=6.1 Hz, 1H) 1.13 (t, J=7.1 Hz, 1H). LC-MS ESI (M+H)⁺=381.68.

Intermediate 115: ethyl (3S)-8,8-difluoro-2-azaspiro[4.5]decane-3-carboxylate

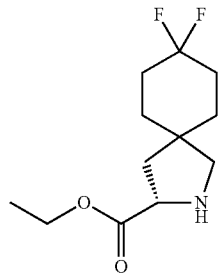 [SMILES: CCOC(=O)[C@@H]1CC2(CCC(F)(F)CC2)CN1]

To a solution of 3-ethyl 2-(phenylmethyl) (3S)-8,8-difluoro-2-azaspiro[4.5]decane-2,3-dicarboxylate (114) (630 mg, 1.65 mmol) in absolute ethanol (12 mL), was added 20% Pd(OH)₂ on carbon (65 mg) and the reaction hydrogenated on a Fisher-Porter apparatus for 18 h at 60 psi. The reaction was filtered through celite and concentrated in vacuo to afford the title compound as a clear oil (380 mg, 93% yield).

Intermediate 116: (3S)-8,8-difluoro-2-{N-[(methyloxy)carbonyl]-L-valyl}-2-azaspiro[4.5]decane-3-carboxylic acid

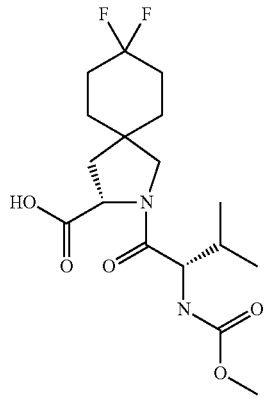 [SMILES: COC(=O)N[C@H](C(=O)N1CC2(CCC(F)(F)CC2)C[C@H]1C(=O)O)C(C)C]

To a solution of ethyl (3S)-8,8-difluoro-2-azaspiro[4.5]decane-3-carboxylate (115), (380 mg, 1.54 mmol) in anhydrous $CH_2Cl_2$ (10 mL) was added HATU (614 mg, 1.6 mmol), N-[(methyloxy)carbonyl]-L-valine (283 mg, 1.6 mmol) followed by triethylamine (0.43 mL, 3.1 mmol) and the reaction stirred at room temperature under nitrogen for 1 h. The reaction was concentrated in vacuo and the residue purified by silica gel chromatography eluting with 15-80% hexanes/EtOAc. Appropriate fractions were combined and concentrated in vacuo. The residue was dissolved in THF/water/methanol (5 mL/2.5 mL/2.5 mL) and lithium hydroxide monohydrate was added (119 mg, 2.8 mmol) and the solution stirred at room temperature for 30 min. The reaction was treated with 1N HCl (3.5 mL) and partitioned between EtOAc and water (50 mL each). The aqueous layer was extracted with ethyl acetate (50 mL), the organic layers were combined and dried ($MgSO_4$) and concentrated in vacuo. The residue was triturated in diethyl ether and concentrated in vacuo to afford the title compound as a white solid (542 mg, 93% yield). $^1$H NMR (400 MHz, DMSO-$d_6$) δ ppm 12.47 (br. s., 1H) 7.41 (d, J=8.0 Hz, 1H) 4.24 (t, J=8.6 Hz, 1H) 3.95-4.14 (m, 2H) 3.52 (s, 3H) 3.25-3.33 (m, 1H) 2.22 (dd, J=12.3, 8.4 Hz, 1H) 1.79-2.11 (m, 5H) 1.58-1.77 (m, 3H) 1.41-1.59 (m, 2H) 0.93 (dd, J=12.7, 6.6 Hz, 6H). LC-MS ESI (M+H)$^+$=377.23.

Intermediate 117: 2-{4'-[({[(2S)-1-((2S)-3-methyl-2-{[(methyloxy)carbonyl]amino}butanoyl)-2-pyrrolidinyl]carbonyl}oxy)acetyl]-4-biphenylyl}-2-oxoethyl (3S)-8,8-difluoro-2-((2S)-3-methyl-2-{[(methyloxy)carbonyl]amino}butanoyl)-2-azaspiro[4.5]decane-3-carboxylate

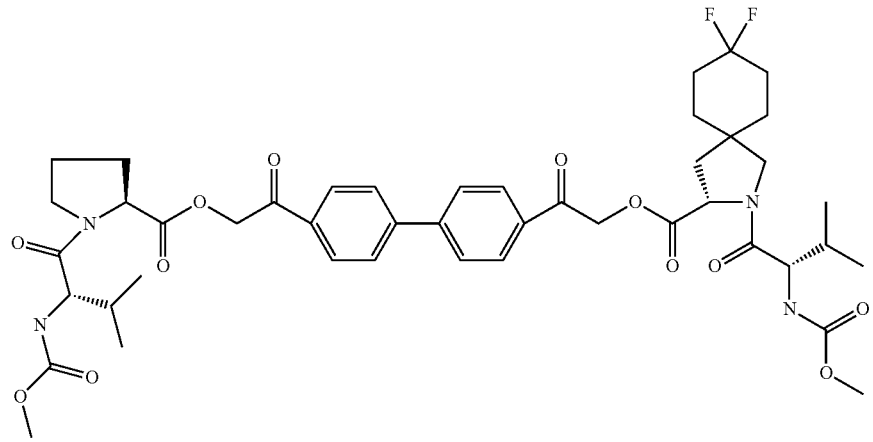 [SMILES: COC(=O)N[C@H](C(=O)N1CCC[C@H]1C(=O)OCC(=O)c1ccc(-c2ccc(C(=O)COC(=O)[C@@H]3CC4(CCC(F)(F)CC4)CN3C(=O)[C@@H](NC(=O)OC)C(C)C)cc2)cc1)C(C)C]

To a solution of (3S)-8,8-difluoro-2-{N-[(methyloxy)carbonyl]-L-valyl}-2-azaspiro[4.5]decane-3-carboxylic acid (116) (168 mg, 0.45 mmol) and 2-[4'-(bromoacetyl)-4-biphenylyl]-2-oxoethyl N-[(methyloxy)carbonyl]-L-valyl-L-prolinate (70) (250 mg, 0.43 mmol) in anhydrous acetonitrile (2 mL) was added triethylamine (0.09 mL, 0.64 mmol) and the reaction stirred at room temperature under nitrogen for 1 h. The reaction was partitioned between EtOAc and 0.1 N HCl (30 mL each), the organic layer was washed with brine and dried ($MgSO_4$) and concentrated in vacuo. The residue was purified by silica gel chromatography eluting with 65-100% hexanes/EtOAc to afford the title compound as an off white solid (309 mg, 82% yield).

Example 18 dimethyl (4,4'-biphenyldiylbis{1H-imidazole-4,2-diyl(3S)-8-oxa-2-azaspiro[4.5]decane-3,2-diyl[(2S)-3-methyl-1-oxo-1,2-butanediyl]})biscarbamate

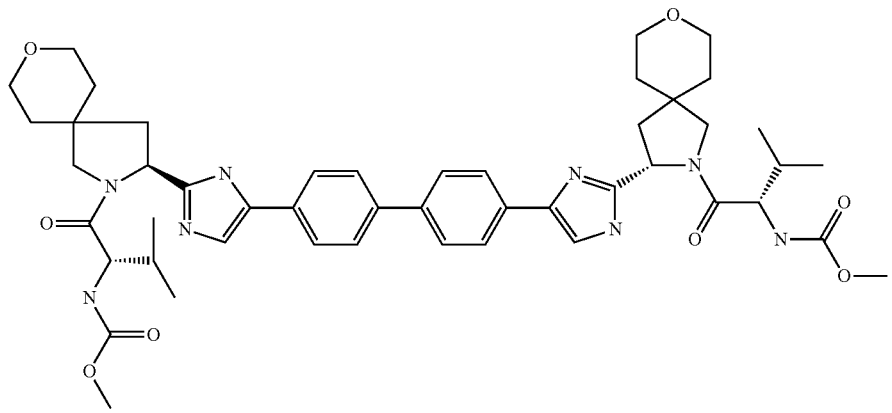 [SMILES: COC(=O)N[C@H](C(=O)N1CC2(CCOCC2)C[C@H]1c1nc(-c2ccc(-c3ccc(-c4cnc([C@@H]5CC6(CCOCC6)CN5C(=O)[C@@H](NC(=O)OC)C(C)C)[nH]4)cc3)cc2)c[nH]1)C(C)C]

To a solution of bis(phenylmethyl) (3S,3'S)-3,3'-[4,4'-biphenyldiylbis(1H-imidazole-4,2-diyl)]bis(8-oxa-2-azaspiro[4.5]decane-2-carboxylate) (119) (210 mg, 0.25 mmol) in trifluoroacetic acid (2 mL) cooled to 0° C. was added trifluoromethanesulfonic acid (0.13 mL) and the reaction warmed to room temperature and stirred for 30 min. The reaction was concentrated in vacuo and rotovaped. The residue was rotovaped from toluene and the residue suspended in dichloromethane (3 mL) and treated with 4N HCl in dioxane (0.65 mL). The reaction was concentrated in vacuo and triturated in ether and filtered to obtain a brown solid.

To a solution of the solid in anhydrous DMF (2.5 mL) was added N-[(methyloxy)carbonyl]-L-valine (88 mg, 0.5 mmol), HATU (183 mg, 0.48 mmol) and triethylamine (0.4 mL, 2.88 mmol) and the reaction stirred at room temperature for 1 h. The crude reaction mixture was purified by HPLC eluting with 10-90% acetonitrile/water/0.2% NH$_4$OH to afford the title compound as a pale yellow solid (79 mg, 37% yield). $^1$H NMR (400 MHz, METHANOL-d$_4$) δ ppm 7.60-7.79 (m, 10H) 7.33 (s, 2H) 5.11 (dd, J=9.9, 7.9 Hz, 2H) 4.30 (d, J=10.2 Hz, 2H) 4.17 (d, J=8.2 Hz, 2H) 3.70-3.87 (m, 6H) 3.56-3.71 (m, 10H) 2.40 (dd, J=12.9, 7.8 Hz, 2H) 2.13 (dd, J=12.6, 10.3 Hz, 2H) 1.88-2.00 (m, 2H) 1.70-1.84 (m, 4H) 1.46-1.69 (m, 6H) 0.83-0.97 (m, 12H). HRMS for C$_{48}$H$_{63}$N$_8$O$_8$ (M+H)$^+$ calc: 879.4769. found: 879.4769. Purity (LC-MS): 98%.

Preparation of Intermediate 119

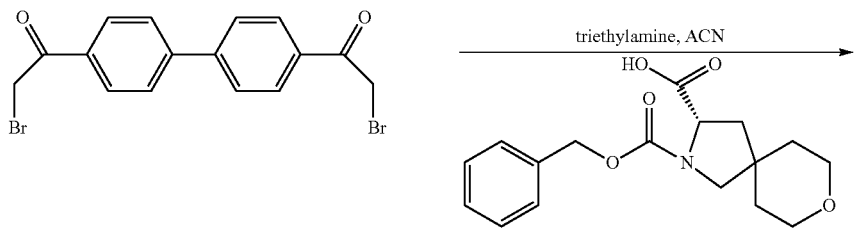

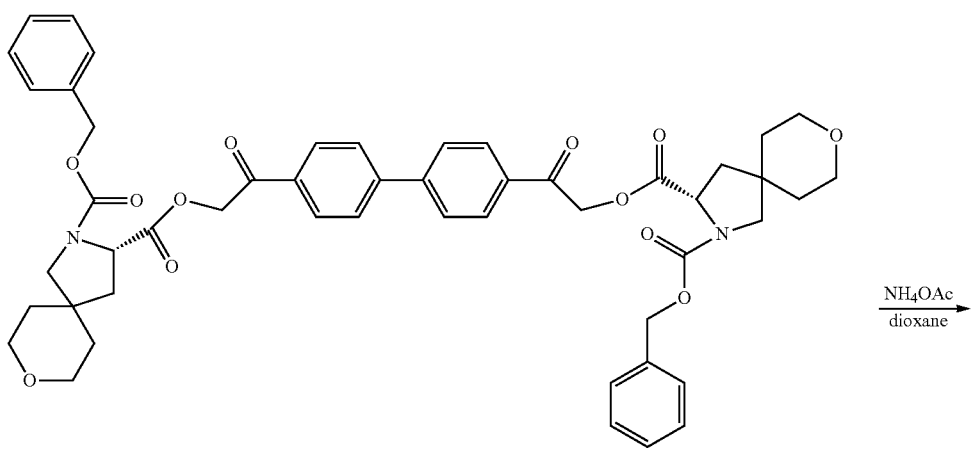

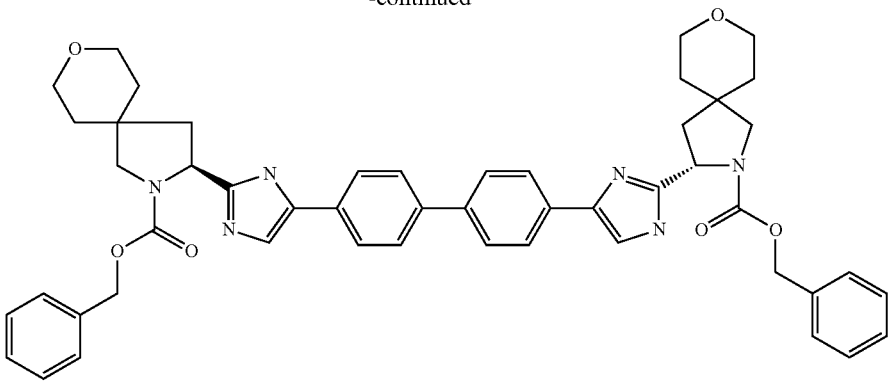

119

Intermediate 118: 3,3'-[4,4'-biphenyldiylbis(2-oxo-2,1-ethanediyl)]2,2'-bis(phenylmethyl)(3S,3'S)bis(-8-oxa-2-azaspiro[4.5]decane-2,3-dicarboxylate)

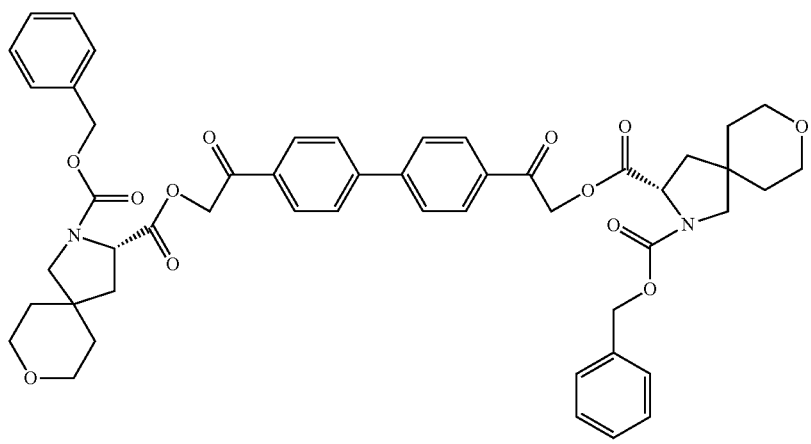 [SMILES: O=C(COC(=O)[C@@H]1CC2(CCOCC2)CN1C(=O)OCc1ccccc1)c1ccc(-c2ccc(C(=O)COC(=O)[C@@H]3CC4(CCOCC4)CN3C(=O)OCc3ccccc3)cc2)cc1]

To a solution of 1,1'-(4,4'-biphenyldiyl)bis(2-bromoethanone) (155 mg, 0.39 mmol) and (3S)-2-{[(phenylmethyl)oxy]carbonyl}-8-oxa-2-azaspiro[4.5]decane-3-carboxylic acid (121) (275 mg, 0.86 mmol) in anhydrous acetonitrile (4 mL) was added triethylamine (0.19 mL, 1.4 mmol) and the solution stirred at room temperature under nitrogen for 3.5 h. The reaction was partitioned between EtOAc and 0.1 N HCl (40 mL each), the organic layer washed with brine and dried (MgSO$_4$) and concentrated in vacuo. The residue was purified by silica gel chromatography eluting with 20-100% hexanes/EtOAc to afford the title compound as a white solid (225 mg, 66% yield).

Intermediate 119: bis(phenylmethyl) (3S,3'S)-3,3'-[4,4'-biphenyldiylbis(1H-imidazole-4,2-diyl)]bis(8-oxa-2-azaspiro[4.5]decane-2-carboxylate)

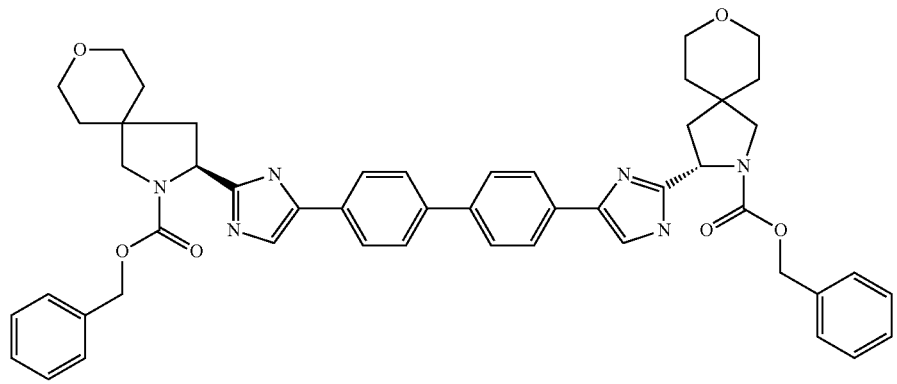 [SMILES: O=C(OCc1ccccc1)N1CC2(CCOCC2)C[C@H]1c1nc(-c2ccc(-c3ccc(-c4cnc([C@@H]5CC6(CCOCC6)CN5C(=O)OCc5ccccc5)[nH]4)cc3)cc2)c[nH]1]

To a solution of 3,3'-[4,4'-biphenyldiylbis(2-oxo-2,1-ethanediyl)] 2,2'-bis(phenylmethyl) (3S,3'S)bis(-8-oxa-2-azaspiro[4.5]decane-2,3-dicarboxylate) (118) (225 mg, 0.26 mmol) in dioxane (3.5 mL) was added ammonium acetate (318 mg, 4.1 mmol). The reaction was degassed with nitrogen and heated to 110° C. in a sealed tube for 18 h. The reaction was partitioned between EtOAc and sat. NaHCO₃ (35 mL each), the organic layer was washed with brine, dried (MgSO₄) and concentrated in vacuo to afford the title compound in quantitative yield.

Preparation of Intermediate 121

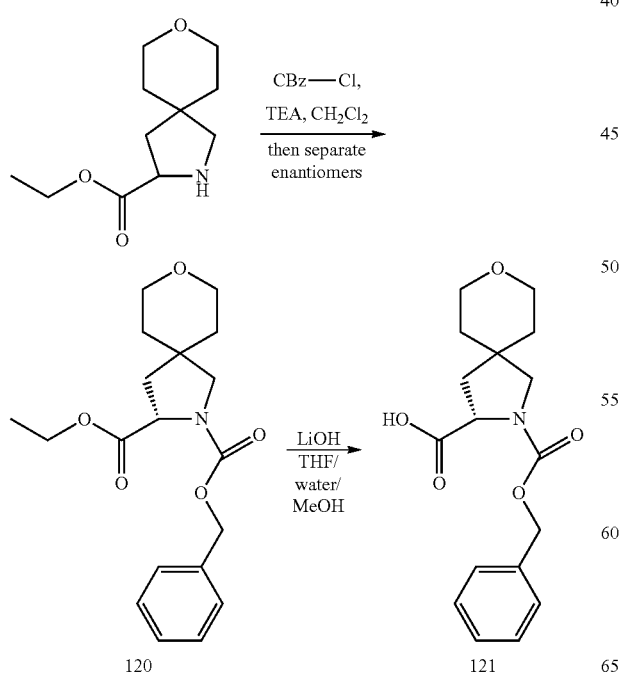

Intermediate 120: 3-ethyl 2-(phenylmethyl) (3S)-8-oxa-2-azaspiro[4.5]decane-2,3-dicarboxylate

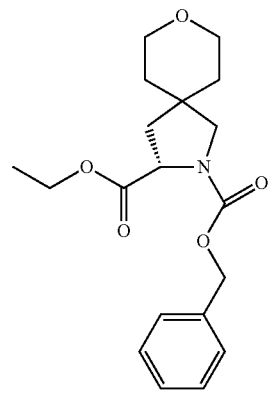 [SMILES: CCOC(=O)[C@@H]1CC2(CCOCC2)CN1C(=O)OCc1ccccc1]

Ethyl 8-oxa-2-azaspiro[4.5]decane-3-carboxylate (3.54 g, 16.6 mmol) was dissolved in dry dichloromethane (80 mL), triethylamine (5.8 mL, 41.5 mmol) was added followed by benzylchloroformate (3.5 mL, 24.9 mmol) and the reaction is stirred at room temperature for 2 h under nitrogen. The reaction was diluted with dichloromethane, washed with 0.2 N HCl, dried over MgSO₄ and concentrated in vacuo. The residue was purified by silica gel chromatography eluting with 20-100% hexanes/EtOAc to afford a yellow oil. The racemate was then separated by chiral HPLC on a 10 μm OD column eluting with 25% isopropanol in hexanes to afford the title compound as a clear oil (1.66 g, 29% yield).

Intermediate 121: (3S)-2-{[(phenylmethyl)oxy]carbonyl}-8-oxa-2-azaspiro[4.5]decane-3-carboxylic acid

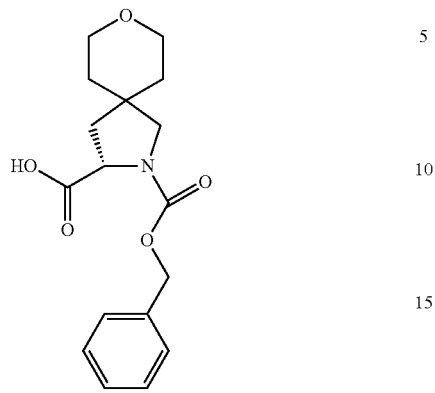

To a solution of 3-ethyl 2-(phenylmethyl) (3S)-8-oxa-2-azaspiro[4.5]decane-2,3-dicarboxylate (120) (300 mg, 0.86 mmol) in THF/water/methanol (3 mL/1.5 mL/1.5 mL) was added lithium hydroxide monohydrate (72 mg, 1.7 mmol) and the reaction stirred at room temperature for 30 min. The reaction was treated with 1N HCl (2 mL) and partitioned between EtOAc and water. The aqueous layer was extracted with EtOAc and the organic layer dried over MgSO$_4$ and concentrated in vacuo to afford the title compound in quantitative yield. $^1$H NMR (400 MHz, DMSO-d$_6$) δ ppm 12.54-12.93 (m, 1H) 7.21-7.47 (m, 5H) 4.90-5.20 (m, 2H) 4.11-4.41 (m, 1H) 3.44-3.70 (m, 5H) 3.24 (dd, J=15.0, 11.7 Hz, 1H) 2.32 (td, J=13.6, 8.5 Hz, 1H) 1.73 (ddd, J=16.8, 12.9, 7.2 Hz, 1H) 1.38-1.64 (m, 4H). LC-MS ESI (M−H)$^-$=318.19.

Example 19

1,1-dimethylethyl 2-{N-[(methyloxy)carbonyl]-L-valyl}-3-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,8-diazaspiro[4.5]decane-8-carboxylate

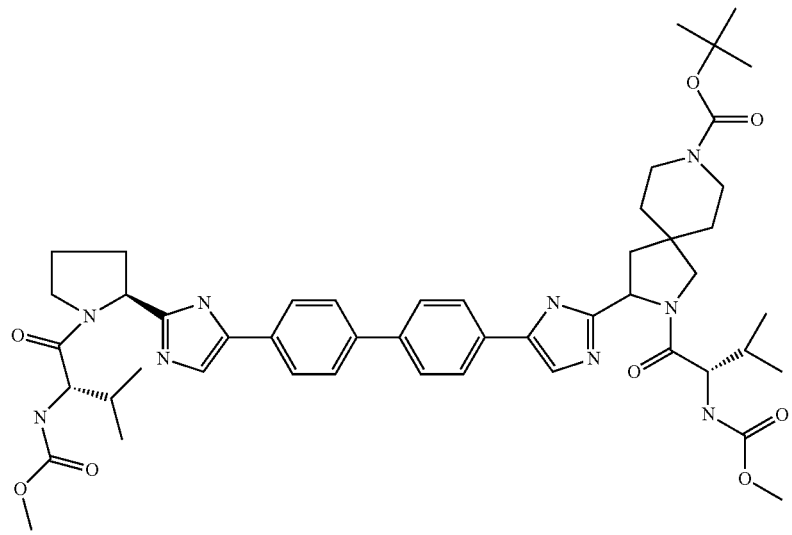 [SMILES: COC(=O)N[C@H](C(=O)N1CC2(CCN(C(=O)OC(C)(C)C)CC2)CC1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]

A solution of 1,1-dimethylethyl 2-((2S)-3-methyl-2-{[(methyloxy)carbonyl]amino}butanoyl)-3-({[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]amino}carbonyl)-2,8-diazaspiro[4.5]decane-8-carboxylate (134) (126 mg, 0.14 mmol) and ammonium acetate (105 mg, 1.4 mmol) in anhydrous dioxane (1.5 mL) was degassed with nitrogen and heated in a sealed tube to 110° C. for 18 h. The reaction was concentrated in vacuo and purified by HPLC eluting with 10-90% acetonitrile/water/0.2% NH$_4$OH to afford the title compound as a tan solid (84 mg, 68% yield). $^1$H NMR (400 MHz, METHANOL-d$_4$) δ ppm 7.56-7.87 (m, 10H) 7.31 (br. s., 2H) 5.04-5.23 (m, 1H) 4.11-4.32 (m, 2H) 3.93-4.04 (m, 1H) 3.80-3.92 (m, 1H) 3.63 (s, 6H) 3.33-3.61 (m, 6H) 1.86-2.49 (m, 9H) 1.68 (br. s., 1H) 1.56 (br. s., 2H) 1.37-1.49 (m, 9H) 0.81-1.08 (m, 15H). HRMS for C$_{49}$H$_{65}$N$_9$O$_8$ (M+H)$^+$ calc: 908.5034. found: 908.5031. Purity (LC-MS): 93%.

Preparation of Intermediate 134

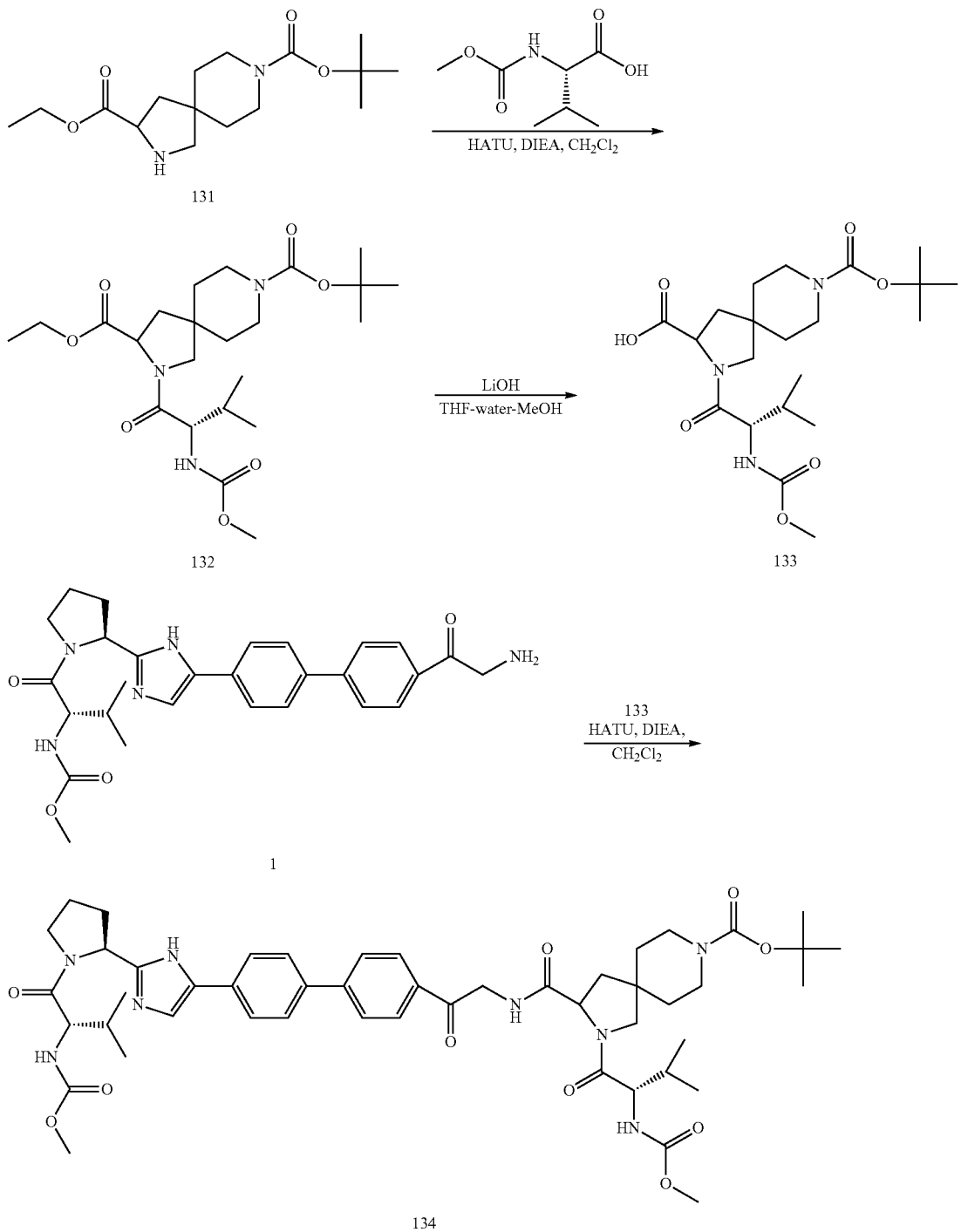

Intermediate 131: 8-(1,1-dimethylethyl) 3-ethyl 2,8-diazaspiro[4.5]decane-3,8-dicarboxylate

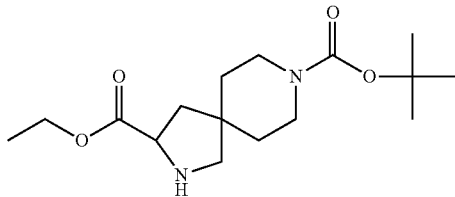 [SMILES: CCOC(=O)C1CC2(CCN(C(=O)OC(C)(C)C)CC2)CN1]

This compound was obtained as a racemate from 1,1-dimethylethyl 4-formyl-1-piperidinecarboxylate following the procedure outlined in WO 98/08850 pp. 50.

Intermediate 132: 8-(1,1-dimethylethyl) 3-ethyl 2-{N-[(methyloxy)carbonyl]-L-valyl}-2,8-diazaspiro[4.5]decane-3,8-dicarboxylate

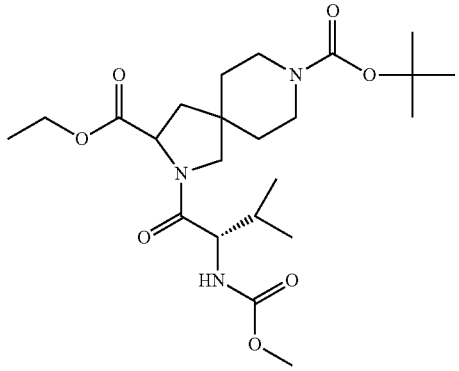 [SMILES: CCOC(=O)C1CC2(CCN(C(=O)OC(C)(C)C)CC2)CN1C(=O)[C@@H](NC(=O)OC)C(C)C]

To a solution of 8-(1,1-dimethylethyl) 3-ethyl 2,8-diazaspiro[4.5]decane-3,8-dicarboxylate (131) (150 mg, 0.48 mmol), HATU (183 mg, 0.48 mmol) and N-[(methyloxy)carbonyl]-L-valine (93 mg, 0.53 mmol) in anhydrous $CH_2Cl_2$ (4 mL) was added Hunig's base (0.17 mL, 0.96 mmol) and the reaction stirred at room temperature under nitrogen for 2 h. The reaction was concentrated in vacuo and purified by silica gel chromatography eluting with 15-80% hexanes/EtOAc to afford the title compound as a pale yellow oil (125 mg, 55% yield).

Intermediate 133: 8-{[(1,1-dimethylethyl)oxy]carbonyl}-2-{N-[(methyloxy)carbonyl]-L-valyl}-2,8-diazaspiro[4.5]decane-3-carboxylic acid

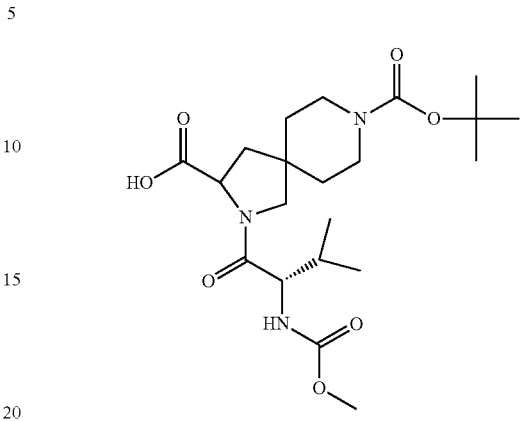

To a solution of 8-(1,1-dimethylethyl) 3-ethyl 2-{N-[(methyloxy)carbonyl]-L-valyl}-2,8-diazaspiro[4.5]decane-3,8-dicarboxylate (132) (125 mg, 0.27 mmol) in THF/water/MeOH (1.2 mL/0.6 mL/0.6 mL) was added lithium hydroxide monohydrate (22 mg, 0.53 mmol) and the reaction stirred at room temperature for 1.5 h. The reaction was treated with 1N HCl (0.5 mL) and partitioned between EtOAc and 0.1 N HCl (10 mL each) and the aqueous layer extracted with EtOAc (10 mL). The organic layers were combined and dried ($MgSO_4$) and concentrated in vacuo to afford the title compound as a white solid (107 mg, 91% yield). $^1$H NMR (400 MHz, DMSO-$d_6$) δ ppm 12.29-12.54 (m, 1H) 7.08-7.44 (m, 1H) 4.47 (t, J=5.4 Hz, 1H) 4.13-4.30 (m, 1H) 3.86-4.13 (m, 3H) 3.45-3.58 (m, 3H) 3.16-3.27 (m, 2H) 2.64 (br. s., 1H) 2.15-2.31 (m, 1H) 1.81-1.95 (m, 1H) 1.43-1.67 (m, 3H) 1.29-1.43 (m, 11H) 0.69-1.03 (m, 6H). LC-MS ESI (M−H)$^-$=440.59.

Intermediate 134: 1,1-dimethylethyl 2-((2S)-3-methyl-2-{[(methyloxy)carbonyl]amino}butanoyl)-3-({[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]amino}carbonyl)-2,8-diazaspiro[4.5]decane-8-carboxylate

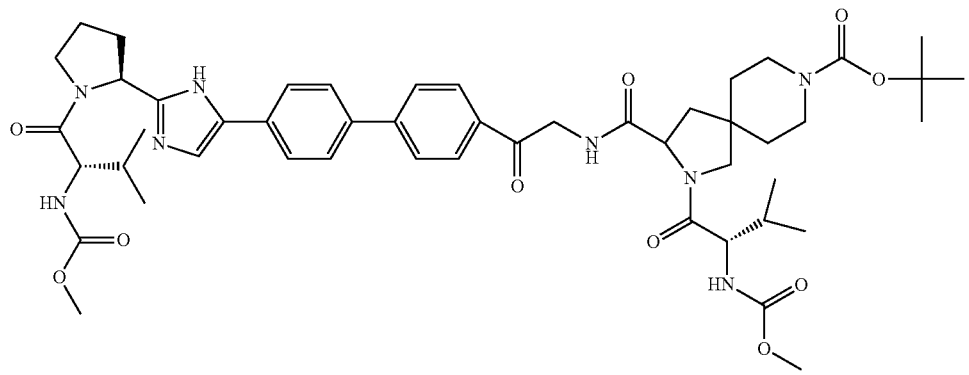 [SMILES: COC(=O)N[C@H](C(=O)N1CC2(CCN(C(=O)OC(C)(C)C)CC2)CC1C(=O)NCC(=O)c1ccc(-c2ccc(-c3cnc([C@@H]4CCCN4C(=O)[C@@H](NC(=O)OC)C(C)C)[nH]3)cc2)cc1)C(C)C]

To a solution of 8-{[(1,1-dimethylethyl)oxy]carbonyl}-2-{N-[(methyloxy)carbonyl]-L-valyl}-2,8-diazaspiro[4.5]decane-3-carboxylic acid (133) (106 mg, 0.24 mmol), HATU (91 mg, 0.24 mmol) and methyl {(1S)-1-[((2S)-2-{4-[4'-(aminoacetyl)-4-biphenylyl]-1H-imidazol-2-yl}-1-pyrrolidinyl)carbonyl]-2-methylpropyl}carbamate dihydrochloride(1) (138 mg, 0.24 mmol) in anhydrous CH$_2$Cl$_2$ (4 mL) was added Hunig's base (0.17 mL, 0.96 mmol) and the reaction stirred at room temperature under nitrogen for 1 h. The reaction was concentrated in vacuo and purified by HPLC eluting with 10-90% acetonitrile/water/0.2% NH$_4$OH to afford the title compound as an off-white solid (129 mg, 58% yield).

Example 20 methyl [(1S)-2-methyl-1-({(2S)-2-[4-(4'-{2-[2-((2S)-3-methyl-2-{[(methyloxy)carbonyl]amino}butanoyl)-2,8-diazaspiro[4.5]dec-3-yl]-1H-imidazol-4-yl}-4-biphenylyl)-1H-imidazol-2-yl]-1-pyrrolidinyl}carbonyl)propyl]carbamate

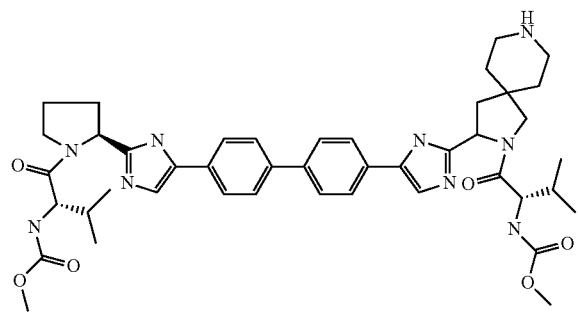 [SMILES: COC(=O)N[C@H](C(=O)N1CC2(CCNCC2)CC1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]

To a solution of 1,1-dimethylethyl 2-{N-[(methyloxy)carbonyl]-L-valyl}-3-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,8-diazaspiro[4.5]decane-8-carboxylate (68 mg, 0.08 mmol) in anhydrous CH$_2$Cl$_2$ (1 mL) was added trifluoroacetic acid (0.3 mL) and the reaction stirred at room temperature for 2 h. The reaction was concentrated in vacuo and purified by HPLC eluting with 10-90% acetonitrile/water/0.2% NH$_4$OH to afford the title compound as a tan solid (49 mg, 81% yield). $^1$H NMR (400 MHz, METHANOL-d$_4$) δ ppm 7.56-7.83 (m, 10H) 7.31 (br. s., 2H) 5.00-5.22 (m, 2H) 4.12-4.30 (m, 3H) 4.01 (br. s., 1H) 3.80-3.91 (m, 1H) 3.57-3.70 (m, 6H) 2.76-3.07 (m, 4H) 1.89-2.48 (m, 10H) 1.69-1.81 (m, 1H) 1.61 (br. s., 2H) 0.82-1.09 (m, 15H). HRMS for C$_{44}$H$_{58}$N$_9$O$_6$ (M+H)$^+$ calc: 808.4510. found: 808.4509. Purity (LC-MS): 94%.

Example 21 methyl [(1S)-1-({(2S)-2-[4-(4'-{2-[8-acetyl-2-((2S)-3-methyl-2-{[(methyloxy)carbonyl]amino}butanoyl)-2,8-diazaspiro[4.5]dec-3-yl]-1H-imidazol-4-yl}-4-biphenylyl)-1H-imidazol-2-yl]-1-pyrrolidinyl}carbonyl)-2-methylpropyl]carbamate

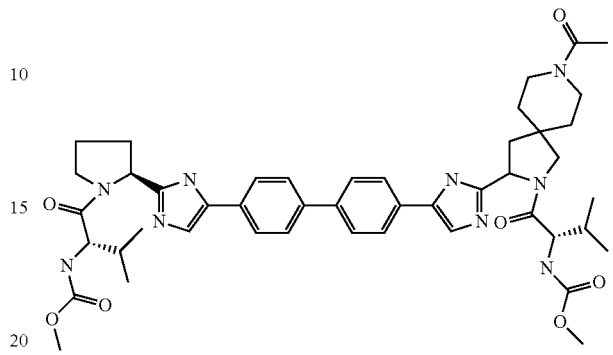

To a solution of methyl [(1S)-2-methyl-1-({(2S)-2-[4-(4'-{2-[2-((2S)-3-methyl-2-{[(methyloxy)carbonyl]amino}butanoyl)-2,8-diazaspiro[4.5]dec-3-yl]-1H-imidazol-4-yl}-4-biphenylyl)-1H-imidazol-2-yl]-1-pyrrolidinyl}carbonyl)propyl]carbamate (Example 20) (19 mg, 0.02 mmol) in anhydrous CH$_2$Cl$_2$ (0.5 mL) was added triethylamine (0.016 mL, 0.12 mmol) followed by acetyl chloride (0.01 mL, 0.14 mmol) and the reaction stirred at room temperature for 1 h. The reaction is concentrated in vacuo and dissolved in methanol (0.7 mL) to which was added potassium carbonate (30 mg, 0.22 mmol) and the reaction was stirred at room temperature for 2 h. The reaction was concentrated in vacuo and partitioned between CH$_2$Cl$_2$ and water (3 mL each) and the aqueous layer extracted with CH$_2$Cl$_2$ (3 mL) and the organic layers combined and dried (MgSO$_4$) and concentrated in vacuo to afford the title compound as a yellow solid (18 mg, 90% yield). $^1$H NMR (400 MHz, METHANOL-d$_4$) δ ppm 7.54-7.88 (m, 10H) 7.32 (br. s., 2H) 5.05-5.23 (m, 2H) 4.03-4.34 (m, 2H) 3.71-4.03 (m, 3H) 3.56-3.71 (m, 8H) 3.34-3.56 (m, 2H) 2.14-2.46 (m, 4H) 1.89-2.14 (m, 6H) 1.46-1.83 (m, 4H) 1.19-1.32 (m, 2H) 0.78-1.07 (m, 14H). HRMS for C$_{46}$H$_{60}$N$_9$O$_7$ (M+H)$^+$ calc: 850.4616. found: 850.4617. Purity (LC-MS): 94%.

Example 22 methyl 2-{N-[(methyloxy)carbonyl]-L-valyl}-3-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,8-diazaspiro[4.5]decane-8-carboxylate

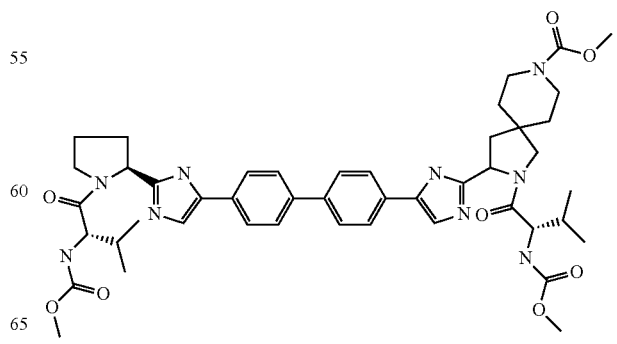

To a solution of methyl [(1S)-2-methyl-1-({(2S)-2-[4-(4'-{2-[2-((2S)-3-methyl-2-{[(methyloxy)carbonyl]amino}butanoyl)-2,8-diazaspiro[4.5]dec-3-yl]-1H-imidazol-4-yl}-4-biphenylyl)-1H-imidazol-2-yl]-1-pyrrolidinyl}carbonyl)propyl]carbamate (Example 20) (19 mg, 0.02 mmol) in anhydrous CH$_2$Cl$_2$ (0.5 mL) was added triethylamine (0.016 mL, 0.12 mmol) followed by acetyl chloride (0.011 mL, 0.14 mmol) and the reaction stirred at room temperature for 1 h. The reaction is concentrated in vacuo and dissolved in methanol (0.7 mL) to which was added potassium carbonate (30 mg, 0.22 mmol) and the reaction was stirred at room temperature for 2 h. The reaction was concentrated in vacuo and partitioned between CH$_2$Cl$_2$ and water (3 mL each) and the aqueous layer extracted with CH$_2$Cl$_2$ (3 mL) and the organic layers combined and dried (MgSO$_4$) and concentrated in vacuo to afford the title compound as a yellow solid (15 mg, 74% yield). $^1$H NMR (400 MHz, METHANOL-d$_4$) δ ppm 7.51-7.92 (m, 10H) 7.32 (br. s., 2H) 5.02-5.25 (m, 1H) 4.03-4.31 (m, 2H) 3.75-4.05 (m, 2H) 3.61-3.72 (m, 7H) 3.34-3.60 (m, 4H) 1.82-2.50 (m, 7H) 1.70 (br. s., 2H) 1.44-1.63 (m, 4H) 1.27 (br. s., 4H) 0.77-1.10 (m, 14H). HRMS for C$_{46}$H$_{60}$N$_9$O$_8$+H)$^+$ calc: 866.4565. found: 850.4564. Purity (LC-MS): 96%.

Example 23

1,1-dimethylethyl 6-{N-[(methyloxy)carbonyl]-L-valyl}-7-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,6-diazaspiro[3.4]octane-2-carboxylate

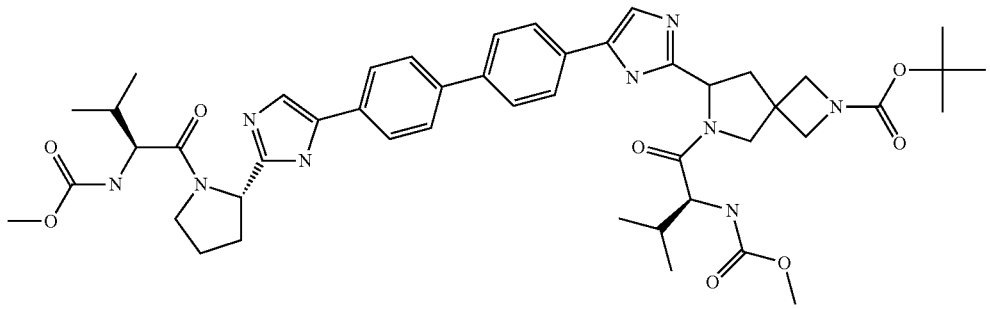 [SMILES: COC(=O)N[C@H](C(=O)N1CC2(CC1c1ncc(-c3ccc(-c4ccc(-c5cnc([C@@H]6CCCN6C(=O)[C@@H](NC(=O)OC)C(C)C)[nH]5)cc4)cc3)[nH]1)CN(C(=O)OC(C)(C)C)C2)C(C)C]

To a solution of 1,1-dimethylethyl 6-((2S)-3-methyl-2-{[(methyloxy)carbonyl]amino}butanoyl)-7-({[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]amino}carbonyl)-2,6-diazaspiro[3.4]octane-2-carboxylate (148) (400 mg, 0.45 mmol) and ammonium acetate (343 mg, 4.5 mmol) in anhydrous dioxane (5 mL) was degassed with nitrogen and heated in a sealed tube to 110° C. for 18 h. The reaction was diluted with EtOAc and filtered and concentrated in vacuo. The residue was purified by C$_{18}$ reverse phase chromatography eluting with 10-100% acetonitrile/water/0.2% NH$_4$OH to afford the title compound as a pale yellow solid (315 mg, 80% yield). $^1$H NMR (400 MHz, DMSO-d$_6$) δ ppm 11.63-12.35 (m, 1H) 7.47-7.92 (m, 9H) 7.19-7.42 (m, 1H) 5.08 (br. s., 2H) 3.94-4.23 (m, 4H) 3.62-3.93 (m, 7H) 3.56 (s, 6H) 2.24-2.45 (m, 2H) 2.14 (br. s., 2H) 1.77-2.07 (m, 6H) 1.37 (d, J=5.5 Hz, 9H) 0.76-1.02 (m, 12H). HRMS for C$_{47}$H$_{62}$N$_9$O$_8$ (M+H)$^+$ calc: 880.4721. found: 880.4725. Purity (LC-MS): 95%.

Preparation of Intermediate 148

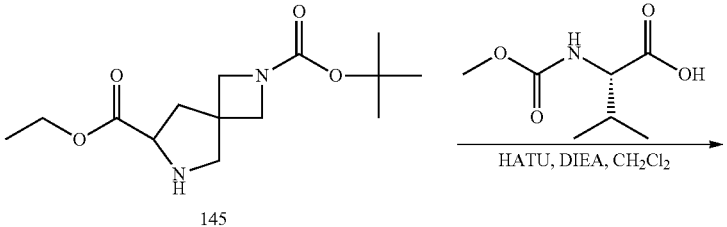

145

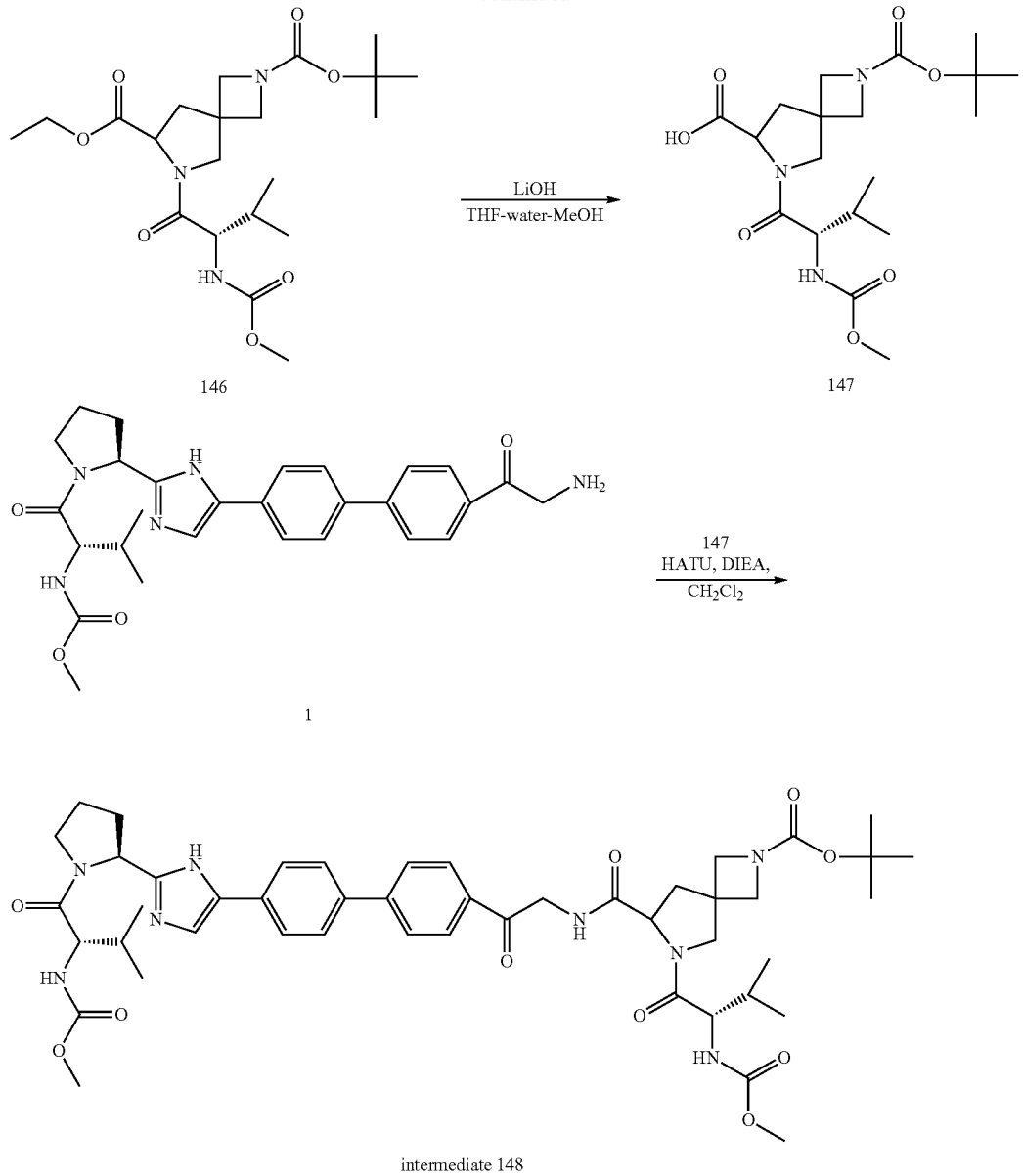
Intermediate 145: 2-(1,1-dimethylethyl) 7-ethyl 2,6-diazaspiro[3.4]octane-2,7-dicarboxylate
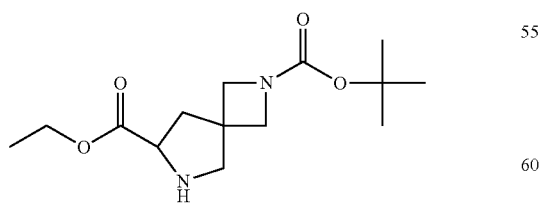
This compound was prepared from 1,1-dimethylethyl 3-formyl-1-azetidinecarboxylate (650 mg, 3.5 mmol) in 93% yield in an analogous fashion to Intermediate 131 in Example 19.

Intermediate 146: 2-(1,1-dimethylethyl) 7-ethyl 6-{N-[(methyloxy)carbonyl]-L-valyl}-2,6-diazaspiro[3.4]octane-2,7-dicarboxylate

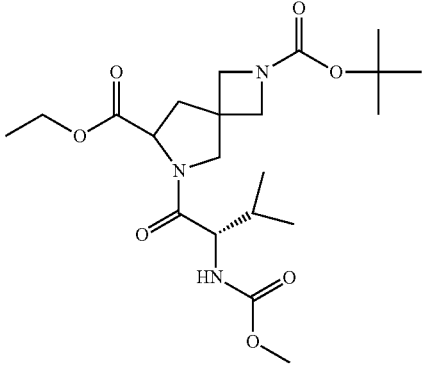 [SMILES: CCOC(=O)C1CC2(CN(C(=O)OC(C)(C)C)C2)CN1C(=O)[C@@H](NC(=O)OC)C(C)C]

To a solution of 2-(1,1-dimethylethyl) 7-ethyl 2,6-diazaspiro[3.4]octane-2,7-dicarboxylate (145) (500 mg, 1.76 mmol), HATU (735 mg, 1.93 mmol) and N-[(methyloxy)carbonyl]-L-valine (339 mg, 1.93 mmol) in anhydrous CH$_2$Cl$_2$ (10 mL) was added Hunig's base (0.68 mL, 3.87 mmol) and the reaction stirred at room temperature under nitrogen for 2 h. The reaction was concentrated in vacuo and purified by C$_{18}$ reverse-phase chromatography eluting with 10-90% ACN/water/0.2% NH$_4$OH to afford the title compound as an off-white solid (398 mg, 51% yield).

Intermediate 147: 2-{[(1,1-dimethylethyl)oxy]carbonyl}-6-{N-[(methyloxy)carbonyl]-L-valyl}-2,6-diazaspiro[3.4]octane-7-carboxylic acid

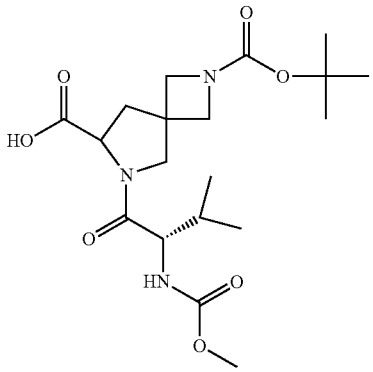 [SMILES: COC(=O)N[C@H](C(=O)N1CC2(CC1C(=O)O)CN(C(=O)OC(C)(C)C)C2)C(C)C]

To a solution of 2-(1,1-dimethylethyl) 7-ethyl 6-{N-[(methyloxy)carbonyl]-L-valyl}-2,6-diazaspiro[3.4]octane-2,7-dicarboxylate (146) (344 mg, 0.78 mmol) in THF/water/methanol (3 mL/1.5 mL/1.5 mL) was added lithium hydroxide monohydrate (65 mg, 1.56 mmol) and the reaction stirred at room temperature for 1.5 h whereupon it was treated with 1N HCl (1.5 mL). The reaction was partitioned between EtOAc and water (30 mL each), the aqueous layer was extracted with EtOAc (30 mL), the organic layers were combined and dried (MgSO$_4$) and concentrated in vacuo to afford the title compound as a white solid (245 mg, 76% yield). $^1$H NMR (400 MHz, DMSO-d$_6$) δ ppm 12.46 (br. s., 1H) 7.06-7.66 (m, 1H) 4.13-4.32 (m, 1H) 3.88-4.12 (m, 2H) 3.56-3.89 (m, 5H) 3.39-3.57 (m, 3H) 2.24-2.45 (m, 1H) 1.99-2.19 (m, 1H) 1.80-1.95 (m, 1H) 1.26-1.44 (m, 9H) 0.56-1.00 (m, 6H). LC-MS ESI (M−H)$^-$=412.41.

Intermediate 148: 1,1-dimethylethyl 6-((2S)-3-methyl-2-{[(methyloxy)carbonyl]amino}butanoyl)-7-({[2-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-2-oxoethyl]amino}carbonyl)-2,6-diazaspiro[3.4]octane-2-carboxylate

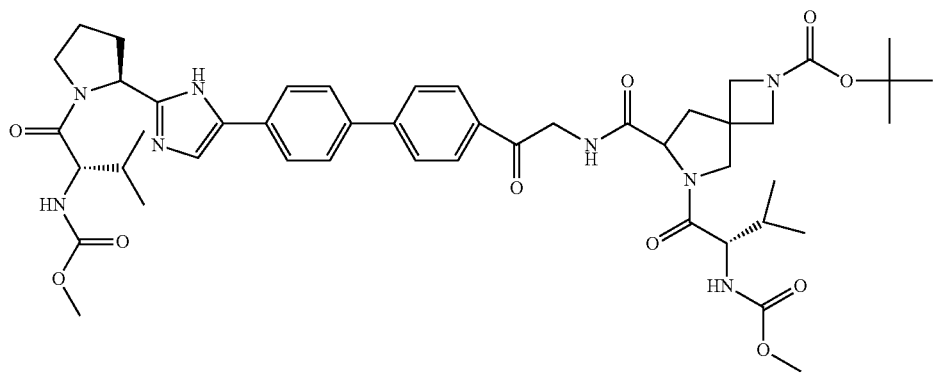 [SMILES: COC(=O)N[C@H](C(=O)N1CC2(CC1C(=O)NCC(=O)c1ccc(-c3ccc(-c4cnc([C@@H]5CCCN5C(=O)[C@@H](NC(=O)OC)C(C)C)[nH]4)cc3)cc1)CN(C(=O)OC(C)(C)C)C2)C(C)C]

To a solution of 2-{[(1,1-dimethylethyl)oxy]carbonyl}-6-{N-[(methyloxy)carbonyl]-L-valyl}-2,6-diazaspiro[3.4]octane-7-carboxylic acid (147) (245 mg, 0.59 mmol), HATU (225 mg, 0.59 mmol) and methyl {(1S)-1-[((2S)-2-{4-[4'-(aminoacetyl)-4-biphenylyl]-1H-imidazol-2-yl}-1-pyrrolidinyl)carbonyl]-2-methylpropyl}carbamate dihydrochloride(1) (342 mg, 0.59 mmol) in anhydrous CH$_2$Cl$_2$ (6 mL) was added Hunig's base (0.41 mL, 2.37 mmol) and the reaction stirred at room temperature under nitrogen for 1 h. The reaction was concentrated in vacuo and purified by C$_{18}$ reverse phase chromatography eluting with 10-100% acetonitrile/water/0.2% NH$_4$OH to afford the title compound as an off-white solid (400 mg, 75% yield).

Example 24 methyl [(1S)-2-methyl-1-({(2S)-2-[4-(4'-{2-[6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate

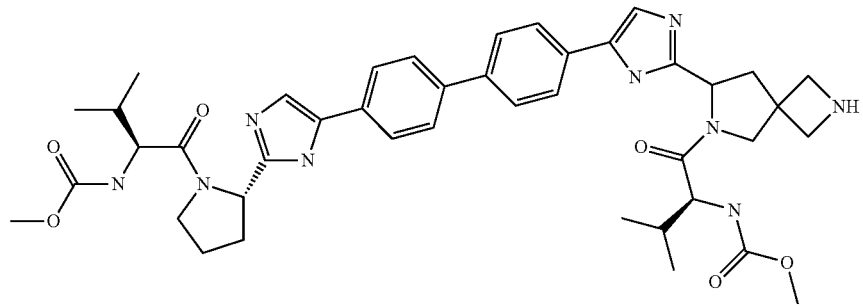 [SMILES: COC(=O)N[C@H](C(=O)N1CC2(CNC2)CC1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]

This compound was prepared in an analogous fashion to Example 20 from 1,1-dimethylethyl 6-{N-[(methyloxy)carbonyl]-L-valyl}-7-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,6-diazaspiro[3.4]octane-2-carboxylate (298 mg, 0.34 mmol) to afford the title compound as a yellow solid (203 mg, 77% yield). $^1$H NMR (400 MHz, METHANOL-d$_4$) δ ppm 7.43-7.86 (m, 8H) 7.04-7.42 (m, 2H) 5.20-5.41 (m, 1H) 5.01-5.19 (m, 2H) 4.30-4.43 (m, 1H) 4.12-4.27 (m, 3H) 3.78-4.03 (m, 5H) 3.65-3.78 (m, 4H) 3.61-3.64 (m, 6H) 3.39-3.52 (m, 1H) 2.54-2.77 (m, 1H) 2.38-2.54 (m, 1H) 2.09-2.39 (m, 2H) 1.89-2.13 (m, 4H) 0.81-1.13 (m, 12H). HRMS for C$_{42}$H$_{54}$N$_9$O$_6$ (M+H)$^+$ calc: 780.4197. found: 780.4200. Purity (LC-MS): 96%.

Example 25 methyl [(1S)-1-({(2S)-2-[4-(4'-{2-[2-acetyl-6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)-2-methylpropyl]carbamate

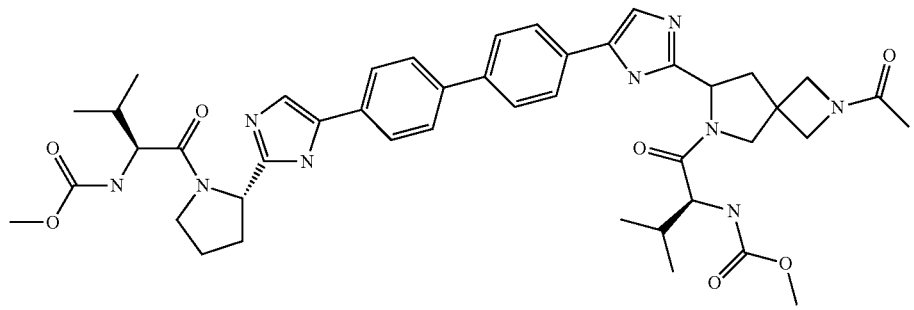 [SMILES: COC(=O)N[C@H](C(=O)N1CC2(CC1c1ncc(-c3ccc(-c4ccc(-c5cnc([C@@H]6CCCN6C(=O)[C@@H](NC(=O)OC)C(C)C)[nH]5)cc4)cc3)[nH]1)CN(C(C)=O)C2)C(C)C]

This compound was prepared in an analogous fashion to Example 21 from methyl [(1S)-2-methyl-1-({(2S)-2-[4-(4'-{2-[6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate Example 24 (40 mg, 0.05 mmol) to afford the title compound as a yellow solid (35 mg, 83% yield). $^1$H NMR (400 MHz, DMSO-$d_6$) δ ppm 11.67-12.33 (m, 1H) 7.19-7.99 (m, 12H) 5.07 (br. s., 1H) 3.92-4.25 (m, 4H) 3.67-3.94 (m, 4H) 3.45-3.66 (m, 8H) 2.20-2.46 (m, 3H) 2.17 (br. s., 2H) 1.80-2.06 (m, 5H) 1.60-1.82 (m, 3H) 0.78-1.02 (m, 12H). HRMS for $C_{44}H_{66}N_9O_7$ $(M+H)^+$ calc: 822.4303. found: 822.4300. Purity (LC-MS): 91%.

Example 26 methyl 6-{N-[(methyloxy)carbonyl]-L-valyl}-7-(4-{4'-[2-((2S)-{N-[(methyloxy)carbonyl]-L-valyl}-2-pyrrolidinyl)-1H-imidazol-4-yl]-4-biphenylyl}-1H-imidazol-2-yl)-2,6-diazaspiro[3.4]octane-2-carboxylate

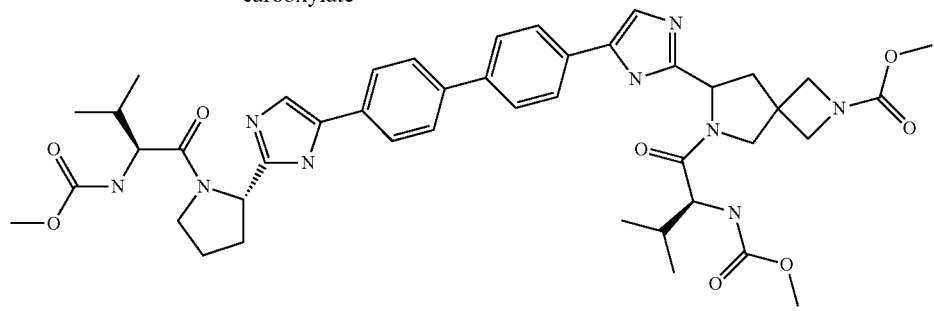

This compound was prepared in an analogous fashion to Example 22 from methyl [(1S)-2-methyl-1-({(2S)-2-[4-(4'-{2-[6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate (Example 24) (40 mg, 0.05 mmol) to afford the title compound as a yellow solid (37 mg, 87% yield). $^1$H NMR (400 MHz, DMSO-$d_6$) δ ppm 11.38-12.37 (m, 1H) 7.58-7.93 (m, 8H) 7.19-7.59 (m, 3H) 4.93-5.17 (m, 1H) 3.63-4.22 (m, 7H) 3.45-3.64 (m, 6H) 2.24-2.48 (m, 4H) 2.08 (br. s., 4H) 1.79-2.07 (m, 6H) 0.99-1.18 (m, 1H) 0.75-0.97 (m, 14H). HRMS for $C_{44}H_{66}N_9O_8$ $(M+H)^+$ calc: 838.4252. found: 838.4252. Purity (LC-MS): 87%.

Example 27 methyl [(1S)-2-methyl-1-({(2S)-2-[4-(4'-{2-[2-[(methylamino)carbonyl]-6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate

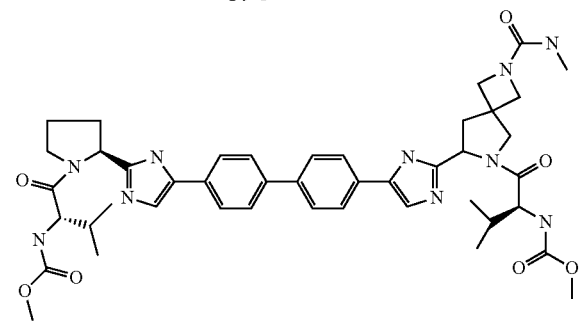

To a solution of methyl [(1S)-2-methyl-1-({(2S)-2-[4-(4'-{2-[6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate (Example 24) (45 mg, 0.06 mmol) in anhydrous $CH_2Cl_2$ (0.6 mL) was added methyl isocyanate (0.01 mL, 0.17 mmol) and the reaction stirred at room temperature for 2 h. The solvent was removed in vacuo and the residue dissolved in methanol (1 mL) and potassium carbonate (40 mg, 0.29 mmol) was added and the reaction stirred at room temperature for 18 h. The reaction was partitioned between $CH_2Cl_2$ (10 mL) and water (5 mL), the aqueous layer was extracted with $CH_2Cl_2$ (5 mL), the organic layers were combined and dried ($MgSO_4$) and concentrated in vacuo to afford the title compound as a yellow solid (34 mg, 70% yield). $^1$H NMR (400 MHz, METHANOL-$d_4$) δ ppm 7.64 (br. s., 10H) 7.33 (br. s., 2H) 5.06-5.22 (m, 1H) 4.03-4.46 (m, 3H) 3.73-4.04 (m, 8H) 3.54-3.73 (m, 6H) 3.46 (q, J=7.0 Hz, 2H) 2.52-2.76 (m, 5H) 2.10-2.53 (m, 4H) 2.02 (br. s., 3H) 0.70-1.09 (m, 12H). HRMS for $C_{44}H_{57}N_{10}O_7$ $(M+H)^+$ calc: 837.4412. found: 838.4416. Purity (LC-MS): 91%.

Example 28 methyl [(1S)-2-methyl-1-({(2S)-2-[4-(4'-{2-[6-((2S)-3-methyl-2-{[(methyloxy)carbonyl]amino}butanoyl)-2-(methylsulfonyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate

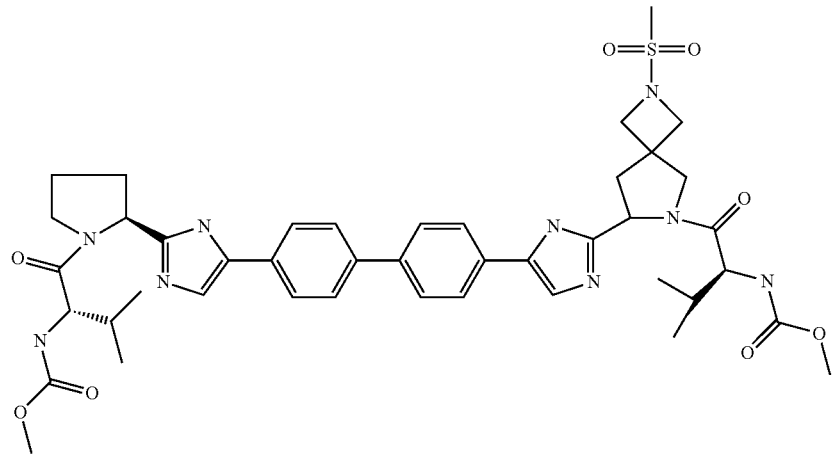 [SMILES: COC(=O)N[C@H](C(=O)N1CC2(CC1c1ncc(-c3ccc(-c4ccc(-c5cnc([C@@H]6CCCN6C(=O)[C@@H](NC(=O)OC)C(C)C)[nH]5)cc4)cc3)[nH]1)CN(S(C)(=O)=O)C2)C(C)C]

To a solution of methyl [(1S)-2-methyl-1-({(2S)-2-[4-(4'-{2-[6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate (Example 24) (60 mg, 0.08 mmol) in anhydrous CH$_2$Cl$_2$ (1 mL) was added triethylamine (0.054 mL, 0.39 mmol) and the reaction was cooled to 0° C. Methanesulfonyl chloride (0.018 mL, 0.23 mmol) was added and the reaction stirred at 0° C. for 15 minutes. The solvent was removed in vacuo and the residue dissolved in methanol (1 mL) and potassium carbonate (80 mg, 0.58 mmol) was added and the reaction stirred at room temperature for 1.5 h. The reaction was partitioned between CH$_2$Cl$_2$ (10 mL) and water (10 mL) the organic layer was dried (MgSO$_4$) and concentrated in vacuo to afford the title compound as a tan solid (57 mg, 86% yield). $^1$H NMR (400 MHz, METHANOL-d$_4$) δ ppm 7.50-7.86 (m, 10H) 7.33 (br. s., 2H) 5.06-5.21 (m, 1H) 4.04-4.26 (m, 2H) 3.75-4.05 (m, 6H) 3.56-3.72 (m, 6H) 3.38-3.55 (m, 2H) 2.84-3.04 (m, 3H) 2.70-2.86 (m, 1H) 2.40-2.64 (m, 1H) 2.10-2.40 (m, 3H) 1.83-2.09 (m, 2H) 1.20-1.37 (m, 2H) 1.07-1.20 (m, 2H) 0.81-1.07 (m, 12H). HRMS for C$_{43}$H$_{66}$N$_9$O$_8$S (M+H)$^+$ calc: 858.3973. found: 858.3975. Purity (LC-MS): 86%.

Example 29 methyl [(1S)-1-({(2S)-2-[4-(4'-{2-[(7S)-2,2-difluoro-6-((2S)-3-methyl-2-{[(methyloxy)carbonyl]amino}butanoyl)-6-azaspiro[3.4]oct-7-yl]-1H-imidazol-4-yl}-4-biphenylyl)-1H-imidazol-2-yl]-1-pyrrolidinyl}carbonyl)-2-methylpropyl]carbamate

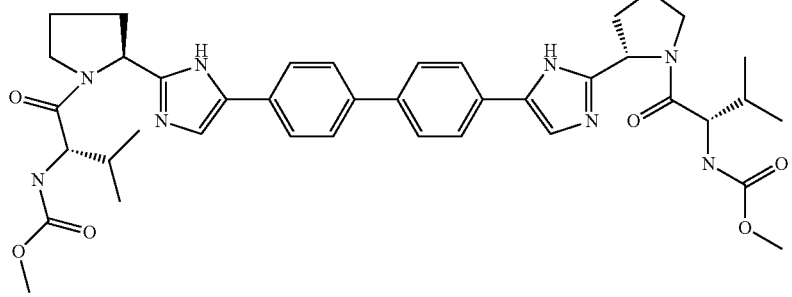

To a solution of 2-{4'-[({[(2S)-1-((2S)-3-methyl-2-{[(methyloxy)carbonyl]amino}butanoyl)-2-pyrrolidinyl]carbonyl}oxy)acetyl]-4-biphenylyl}-2-oxoethyl (7S)-2,2- difluoro-6-((2S)-3-methyl-2-{[(methyloxy)carbonyl]amino}butanoyl)-6-azaspiro[3.4]octane-7-carboxylate (157) (102 mg, 0.12 mmol) in anhydrous dioxane (1.2 mL) was added ammonium acetate (184 mg, 2.4 mmol) and the reaction heated to 110° C. for 4 h. The reaction was partitioned between EtOAc and saturated NaHCO$_3$, the organic layer was washed with brine and dried over MgSO$_4$ and concentrated in vacuo. The residue was purified by C$_{18}$ reverse phase chromatography eluting with 10-100% acetonitrile/water/0.2% NH$_4$OH to afford the title compound as a yellow solid (68 mg, 69% yield). $^1$H NMR (400 MHz, DMSO-d$_6$) δ ppm 11.42-12.37 (m, 2H) 7.56-7.90 (m, 8H) 7.51 (s, 2H) 7.19-7.46 (m, 2H) 4.73-5.39 (m, 2H) 3.91-4.23 (m, 3H) 3.82 (br. s., 2H) 3.54 (s, 6H) 2.55-2.86 (m, 4H) 2.20-2.45 (m, 2H) 2.14 (br. s., 2H) 1.73-2.09 (m, 5H) 0.57-0.99 (m, 12H). HRMS for C$_{43}$H$_{53}$N$_8$O$_6$F$_2$ (M+H)$^+$ calc: 815.4056. found: 815.4059. Purity (LC-MS): 97%.

Preparation of Intermediate 157

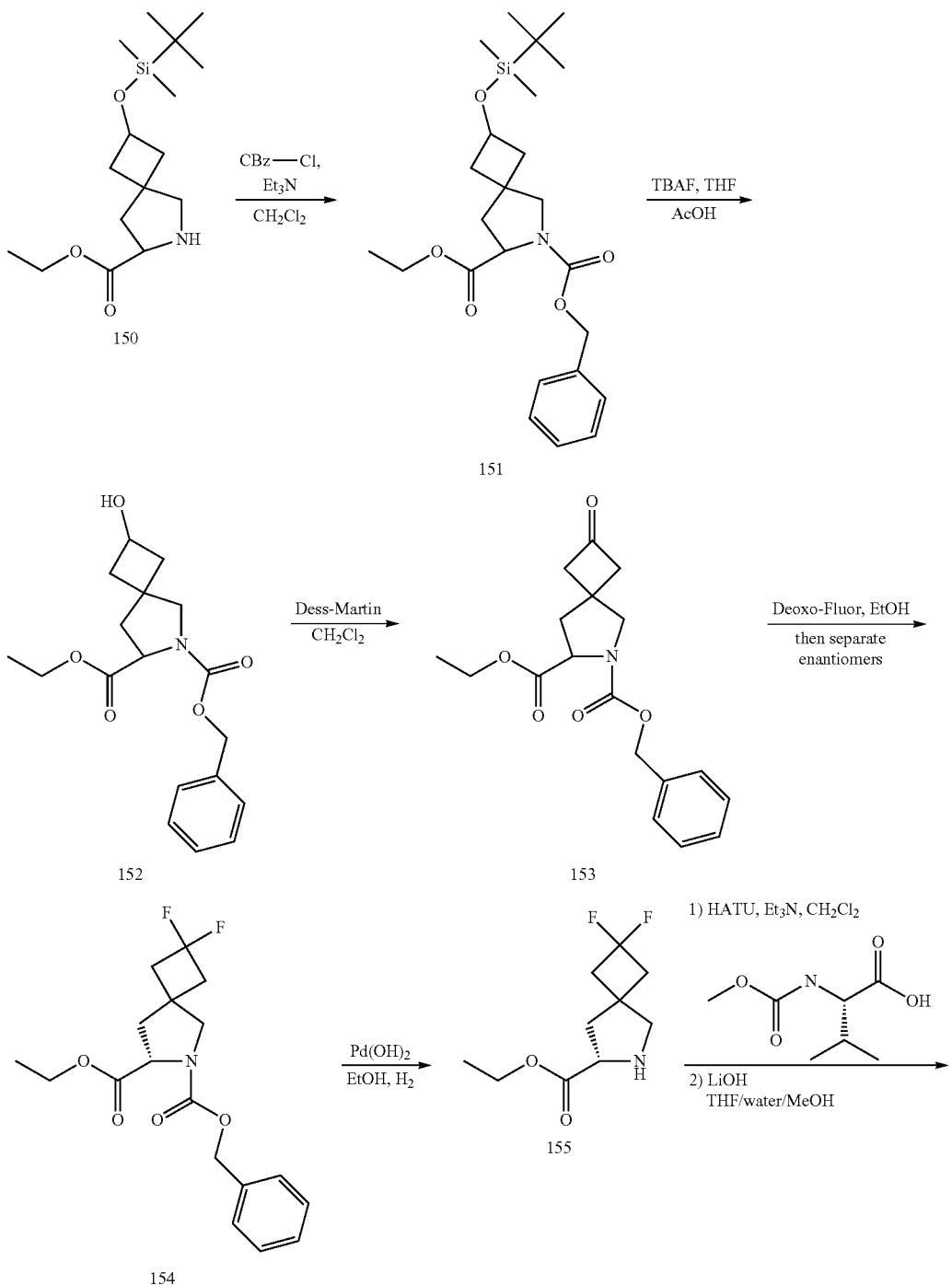

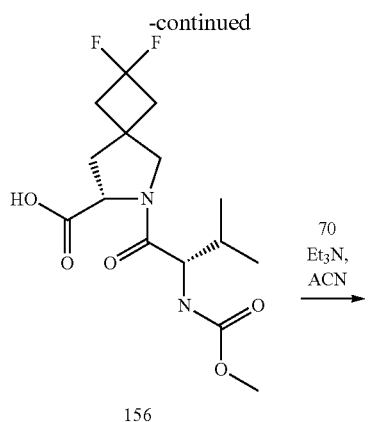

156

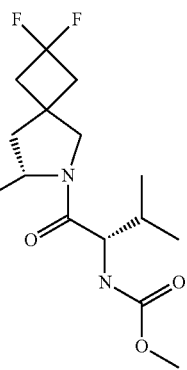

157

Intermediate 150: ethyl 2-{[(1,1-dimethylethyl)(dimethyl)silyl]oxy}-6-azaspiro[3.4]octane-7-carboxylate

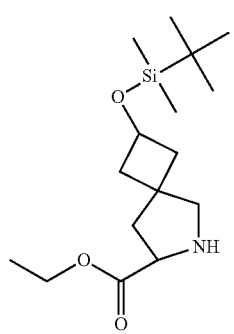 [SMILES: CCOC(=O)C1CC2(CN1)CC(O[Si](C)(C)C(C)(C)C)C2]

This compound was prepared in an analogous fashion to 110 (example 17) from 3-{[(1,1-dimethylethyl)(dimethyl)silyl]oxy}cyclobutanecarbaldehyde (2.23 g, 10.4 mmol) to afford the title compound (2.97 g, 92% yield) as a yellow oil.

Intermediate 151: 7-ethyl 6-(phenylmethyl) 2-{[(1,1-dimethylethyl)(dimethyl)silyl]oxy}-6-azaspiro[3.4]octane-6,7-dicarboxylate

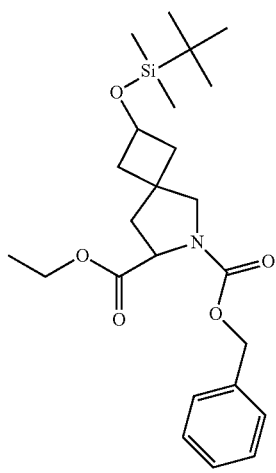 [SMILES: CCOC(=O)C1CC2(CC(O[Si](C)(C)C(C)(C)C)C2)CN1C(=O)OCc1ccccc1]

This compound was prepared in an analogous fashion to 111 (Example 17) from ethyl 2-{[(1,1-dimethylethyl)(dimethyl)silyl]oxy}-6-azaspiro[3.4]octane-7-carboxylate (150) (2.97 g, 9.5 mmol) to obtain the title compound as a yellow oil (1.87 g, 44% yield).

Intermediate 152: 7-ethyl 6-(phenylmethyl) 2-hydroxy-6-azaspiro[3.4]octane-6,7-dicarboxylate

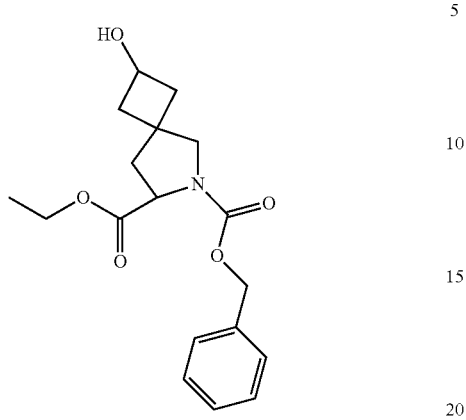

To a solution of 7-ethyl 6-(phenylmethyl) 2-{[(1,1-dimethylethyl)(dimethyl)silyl]oxy}-6-azaspiro[3.4]octane-6,7-dicarboxylate (151) (1.87 g, 4.2 mmol) in THF (20 mL) was added glacial acetic acid (0.48 mL), followed by TBAF (8.5 mL, 1M solution in THF) and the reaction heated to 45° C. for 18 h. The reaction was concentrated in vacuo and partitioned between EtOAc and water. The organic layer was washed with saturated NaHCO$_3$ followed by brine, and then dried over MgSO$_4$ and concentrated in vacuo to afford the title compound as a clear oil in quantitative yield. $^1$H NMR (400 MHz, DMSO-d$_6$) δ ppm 7.17-7.48 (m, 5H) 4.83-5.15 (m, 3H) 3.88-4.34 (m, 4H) 3.35-3.47 (m, 2H) 2.02-2.39 (m, 3H) 1.65-1.96 (m, 3H) 1.00-1.22 (m, 3H). LC-MS ESI (M+H)$^+$=334.17.

Intermediate 153: 7-ethyl 6-(phenylmethyl) 2-oxo-6-azaspiro[3.4]octane-6,7-dicarboxylate

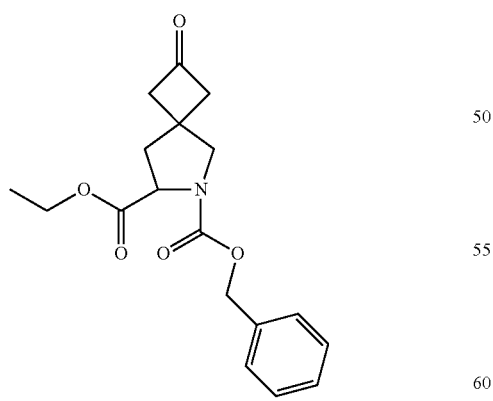

This compound was prepared in an analogous fashion to 113 (Example 17) from 7-ethyl 6-(phenylmethyl) 2-hydroxy-6-azaspiro[3.4]octane-6,7-dicarboxylate (152) (1.39 g, 4.2 mmol) to give the title compound (1.25 g, 90% yield) as a clear oil.

Intermediate 154: 7-ethyl 6-(phenylmethyl) (7S)-2,2-difluoro-6-azaspiro[3.4]octane-6,7-dicarboxylate

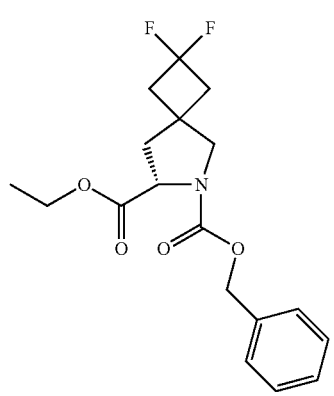 [SMILES: CCOC(=O)[C@@H]1CC2(CN1C(=O)OCc1ccccc1)CC(F)(F)C2]

To a solution of 7-ethyl 6-(phenylmethyl) 2-oxo-6-azaspiro[3.4]octane-6,7-dicarboxylate (153) (1.25 g, 3.8 mmol) in anhydrous dichloromethane (20 mL) was added Deoxo-Fluor (1.2 mL, 6.4 mmol) followed by ethanol (0.04 mL, 0.75 mmol) and the reaction stirred at room temperature under nitrogen for 18 h. The reaction is poured into saturated NaHCO$_3$ and stirred for 10 min. The mixture is extracted with dichloromethane (2×) and the organic layer was washed with 0.1 N HCl and dried over MgSO$_4$ and concentrated in vacuo. The residue was purified by silica gel chromatography eluting with 5-50% hexanes/EtOAc. The racemate was then separated by chiral HPLC on a 10 μm OD column eluting with 25% isopropanol in hexanes to afford the title compound as a clear oil (356 mg, 30% yield).

Intermediate 155: ethyl (7S)-2,2-difluoro-6-azaspiro[3.4]octane-7-carboxylate

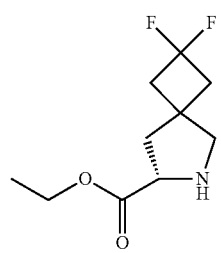

This compound was prepared in an analogous fashion to 115 (Example 17) from 7-ethyl 6-(phenylmethyl) (7S)-2,2-difluoro-6-azaspiro[3.4]octane-6,7-dicarboxylate (14) (356 mg, 1.0 mmol) to afford the title compound as a clear oil (209 mg, 95% yield).

Intermediate 156: (7S)-2,2-difluoro-6-{N-[(methyloxy)carbonyl]-L-valyl}-6-azaspiro[3.4]octane-7-carboxylic acid

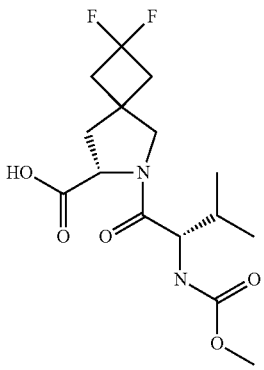 [SMILES: COC(=O)N[C@H](C(=O)N1CC2(C[C@H]1C(=O)O)CC(F)(F)C2)C(C)C]

This compound was prepared in an analogous fashion to 116 (Example 17) from ethyl (7S)-2,2-difluoro-6-azaspiro[3.4]octane-7-carboxylate (155) (207 mg, 0.94 mmol) to afford the title compound as a white solid (263 mg, 81% yield). $^1$H NMR (400 MHz, DMSO-$d_6$) δ ppm 12.53 (br. s., 1H) 7.46 (d, J=8.0 Hz, 1H) 4.24 (t, J=7.8 Hz, 1H) 4.02 (d, J=10.4 Hz, 1H) 3.92 (t, J=8.5 Hz, 1H) 3.62 (d, J=10.4 Hz, 1H) 3.51 (s, 3H) 2.54-2.78 (m, 4H) 2.28-2.44 (m, 1H) 1.81-2.05 (m, 2H) 0.91 (dd, J=11.2, 6.7 Hz, 6H).
LC-MS ESI (M+H)$^+$=349.13.

Intermediate 157: 2-{4'-[({[(2S)-1-((2S)-3-methyl-2-{[(methyloxy)carbonyl]amino}butanoyl)-2-pyrrolidinyl]carbonyl}oxy)acetyl]-4-biphenylyl}-2-oxoethyl (7S)-2,2-difluoro-6-((2S)-3-methyl-2-{[(methyloxy)carbonyl]amino}butanoyl)-6-azaspiro[3.4]octane-7-carboxylate

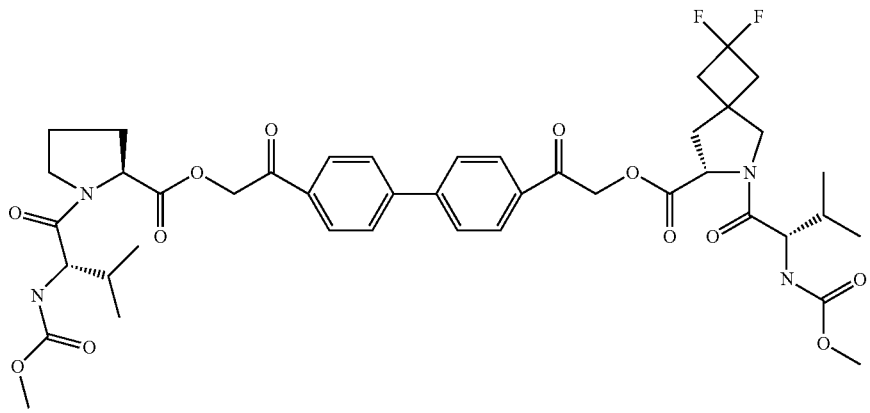 [SMILES: COC(=O)N[C@H](C(=O)N1CCC[C@H]1C(=O)OCC(=O)c1ccc(-c2ccc(C(=O)COC(=O)[C@@H]3CC4(CN3C(=O)[C@@H](NC(=O)OC)C(C)C)CC(F)(F)C4)cc2)cc1)C(C)C]

This compound was prepared in an analogous fashion to 117 (Example 17) from (7S)-2,2-difluoro-6-{N-[(methyloxy)carbonyl]-L-valyl}-6-azaspiro[3.4]octane-7-carboxylic acid (156) (59 mg, 0.17 mmol) and 2-[4'-(bromoacetyl)-4-biphenylyl]-2-oxoethyl N-[(methyloxy)carbonyl]-L-valyl-L-prolinate (70) (95 mg, 0.16 mmol) to afford the title compound as a white solid (104 mg, 75% yield).

Example 30 methyl [(1S)-2-methyl-1-({(2S)-2-[4-(4'-{2-[1-((2S)-3-methyl-2-{[(methyloxy)carbonyl]amino}butanoyl)-8-oxa-1-azaspiro[4.5]dec-2-yl]-1H-imidazol-4-yl}-4-biphenylyl)-1H-imidazol-2-yl]-1-pyrrolidinyl}carbonyl)propyl]carbamate

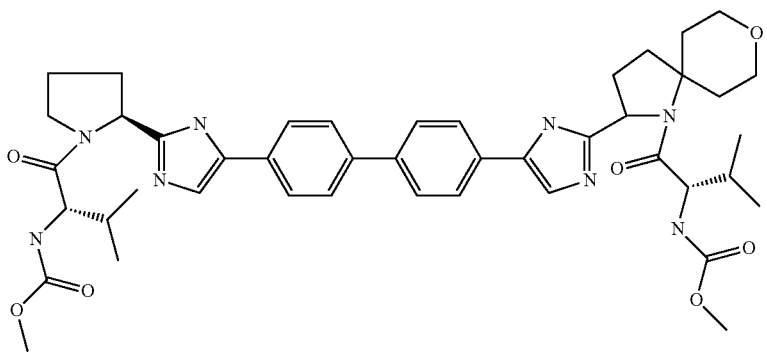 [SMILES: COC(=O)N[C@H](C(=O)N1CCC[C@H]1c1ncc(-c2ccc(-c3ccc(-c4cnc(C5CCC6(CCOCC6)N5C(=O)[C@@H](NC(=O)OC)C(C)C)[nH]4)cc3)cc2)[nH]1)C(C)C]

To a solution of methyl ((1S)-2-methyl-1-{[(2S)-2-(4-{4'-[({[1-((2S)-3-methyl-2-{[(methyloxy)carbonyl]amino}butanoyl)-8-oxa-1-azaspiro[4.5]dec-2-yl]carbonyl}amino)acetyl]-4-biphenylyl}-1H-imidazol-2-yl)-1-pyrrolidinyl]carbonyl}propyl)carbamate (169) (71 mg, 0.09 mmol) in anhydrous dioxane (1 mL) was added ammonium acetate (66 mg, 0.86 mmol) and the reaction was degassed with nitrogen and heated to 110° C. for 48 h in a sealed tube. The reaction was purified by HPLC eluting with 10-90% water/acetonitrile/0.2% NH$_4$OH to afford the title compound as an off-white solid (10 mg, 14% yield). $^1$H NMR (400 MHz, METHANOL-d$_4$) δ ppm 7.56-7.86 (m, 9H) 7.16-7.44 (m, 2H) 6.88-7.09 (m, 1H) 5.72 (br. s., 1H) 5.09-5.21 (m, 1H) 4.03-4.28 (m, 1H) 3.80-4.04 (m, 6H) 3.42-3.71 (m, 9H) 2.11-2.56 (m, 8H) 1.88-2.11 (m, 6H) 0.80-1.06 (m, 12H). HRMS for C$_{44}$H$_{57}$N$_5$O$_7$ (M+H)$^+$ calc: 809.4350. found: 809.4347. Purity (LC-MS): 93%.

Preparation of Intermediate 169

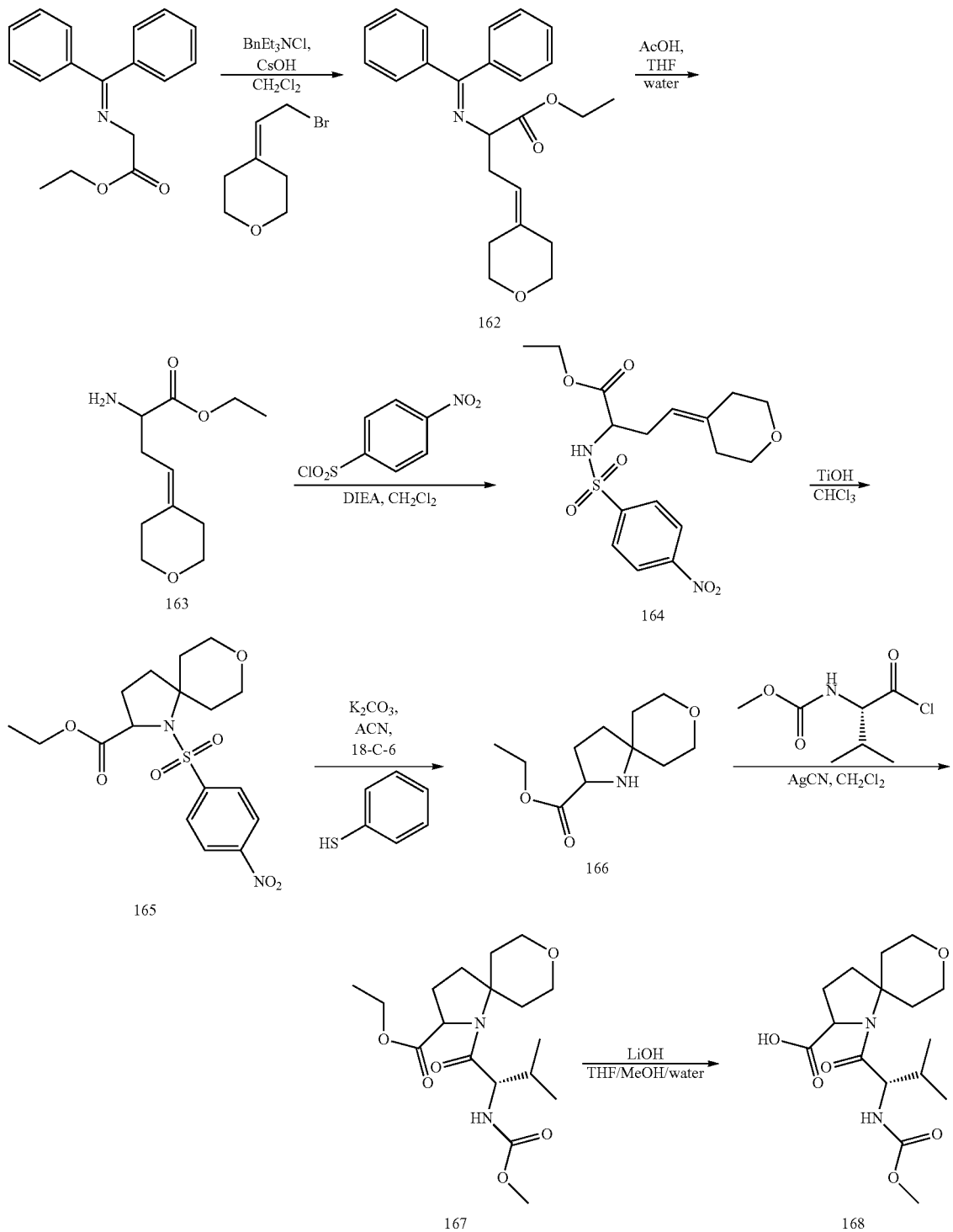

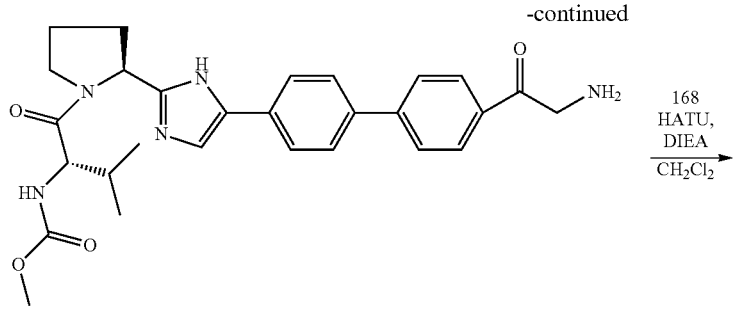

168

HATU, DIEA
―――――→
CH₂Cl₂

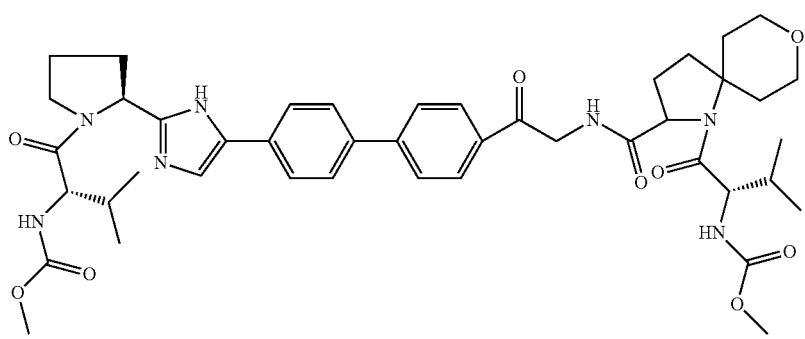

169

Intermediate 162: ethyl 2-[(diphenylmethylidene)amino]-4-(tetrahydro-4H-pyran-4-ylidene)butanoate

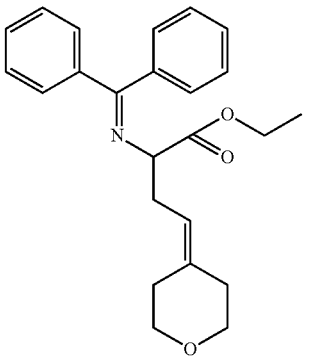 [SMILES: CCOC(=O)C(CC=C1CCOCC1)N=C(c1ccccc1)c1ccccc1]

To a solution of ethyl N-(diphenylmethylidene)glycinate (5.29 g, 19.8 mmol), benzyltriethylammonium chloride (0.41 g, 1.8 mmol) and cesium hydroxide monohydrate (4.54 g, 27.0 mmol) in anhydrous dichloromethane (50 mL) was added 4-(2-bromoethylidene)tetrahydro-2H-pyran (3.44 g, 18.0 mmol) as a solution in anhydrous dichloromethane (40 mL) and the reaction stirred at room temperature for 72 h under nitrogen. The reaction was partitioned between dichloromethane and water and the aqueous layer was extracted with dichloromethane. The organic layer was dried over sodium sulfate and concentrated in vacuo. The residue was purified by silica gel chromatography eluting with 5-40% hexanes/EtOAc to afford the title compound as a clear oil in quantitative yield.

Intermediate 163: ethyl 2-amino-4-(tetrahydro-4H-pyran-4-ylidene)butanoate

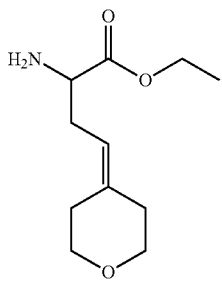

To a solution of ethyl 2-[(diphenylmethylidene)amino]-4-(tetrahydro-4H-pyran-4-ylidene)butanoate (162) (6.8 g, 18.0 mmol) in THF (30 mL) was added water (30 mL) and glacial acetic acid (20 mL) and the reaction stirred at room temperature for 2.5 h. The reaction was concentrated in vacuo and the residue dissolved in 0.1 N HCl. It was extracted twice with ethyl acetate and the organic layer was discarded. To the aqueous layer was added solid potassium carbonate until the solution gave blue pH paper. The aqueous layer was extracted with 15% isopropanol/dichloromethane (3×) and the organic layer dried over sodium sulfate and concentrated in vacuo to afford the title compound as a clear oil (3.05 g, 79% yield).

Intermediate 164: ethyl 2-{[(4-nitrophenyl)sulfonyl]amino}-4-(tetrahydro-4H-pyran-4-ylidene)butanoate

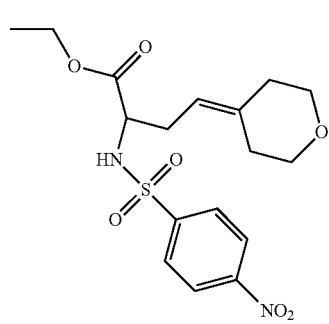 [SMILES: CCOC(=O)C(CC=C1CCOCC1)NS(=O)(=O)c1ccc([N+](=O)[O-])cc1]

To a solution of ethyl 2-amino-4-(tetrahydro-4H-pyran-4-ylidene)butanoate (163) (1.0 g, 4.7 mmol) in anhydrous dichloromethane (30 mL) was added Hunig's base (1.6 mL, 9.4 mmol) followed by 4-nitrobenzenesulfonyl chloride (1.14 g, 5.2 mmol) and the reaction stirred at room temperature under nitrogen for 2 h. The reaction was diluted with dichloromethane and washed with 0.1 N HCl, the organic layer was dried over MgSO$_4$ and concentrated in vacuo. The residue was purified by silica gel chromatography eluting with 10-70% hexanes/EtOAc to afford the title compound as an off-white solid in quantitative yield.

Intermediate 165: ethyl 1-[(4-nitrophenyl)sulfonyl]-8-oxa-1-azaspiro[4.5]decane-2-carboxylate

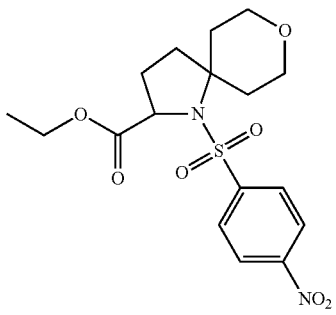 [SMILES: CCOC(=O)C1CCC2(CCOCC2)N1S(=O)(=O)c1ccc([N+](=O)[O-])cc1]

To a solution of ethyl 2-{[(4-nitrophenyl)sulfonyl]amino}-4-(tetrahydro-4H-pyran-4-ylidene)butanoate (164) (1.87 g, 4.7 mmol) in anhydrous chloroform (47 mL) was added trifluoromethanesulfonic acid (0.2 mL, 2.3 mmol) and the reaction stirred at room temperature under nitrogen for 4 h. The reaction was diluted with dichloromethane and washed with saturated NaHCO$_3$ and the organic layer dried over MgSO$_4$ and concentrated in vacuo. The residue was purified by silica gel chromatography eluting with 10-70% hexanes/EtOAc to afford the title compound as a white solid (1.47 g, 79% yield). $^1$H NMR (400 MHz, CHLOROFORM-d) δ ppm 8.19-8.36 (m, 2H) 8.08 (d, J=8.8 Hz, 2H) 4.52 (dd, J=8.5, 2.1 Hz, 1H) 3.99-4.14 (m, 2H) 3.87-3.99 (m, 2H) 3.21-3.49 (m, 2H) 2.58-2.78 (m, 2H) 2.10-2.30 (m, 2H) 1.89-2.06 (m, 2H) 1.77 (dd, J=13.0, 2.1 Hz, 1H) 1.35 (dd, J=12.9, 1.6 Hz, 1H) 1.22 (t, J=7.1 Hz, 3H). LC-MS ESI (M+H)$^+$=399.47.

Intermediate 166: ethyl 8-oxa-1-azaspiro[4.5]decane-2-carboxylate

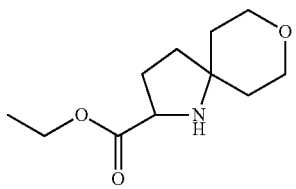

To a solution of ethyl 1-[(4-nitrophenyl)sulfonyl]-8-oxa-1-azaspiro[4.5]decane-2-carboxylate (165) (1.47 g, 3.7 mmol) in anhydrous acetonitrile (25 mL) was added potassium carbonate (0.76 g, 5.5 mmol), 18-crown-6 (0.2 g, 0.7 mmol) and thiophenol (0.6 mL. 5.5 mmol) and the reaction stirred at room temperature for 18 h. The reaction was concentrated in vacuo and the residue dissolved in 0.1 N HCl. The aqueous layer was extracted twice with EtOAc and the organic layer was discarded. The aqueous layer was treated with solid potassium carbonate until the solution gave blue pH paper. It was extracted with 15% isopropanol/dichloromethane (3x) and the organic layer dried over sodium sulfate and concentrated in vacuo to afford the title compound as a clear oil (0.71 g, 90% yield).

Intermediate 167: ethyl 1-{N-[(methyloxy)carbonyl]-L-valyl}-8-oxa-1-azaspiro[4.5]decane-2-carboxylate

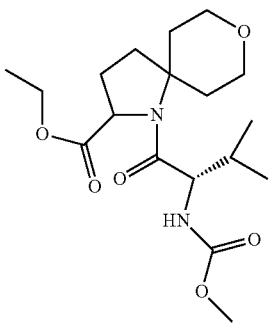 [SMILES: CCOC(=O)C1CCC2(CCOCC2)N1C(=O)[C@@H](NC(=O)OC)C(C)C]

To a solution of ethyl 8-oxa-1-azaspiro[4.5]decane-2-carboxylate (166) (125 mg, 0.59 mmol) in anhydrous dichloromethane (2 mL) was added silver cyanide (98 mg, 0.73 mmol) followed by N-[(methyloxy)carbonyl]-L-valyl chloride (142 mg, 0.73 mmol) as a solution in anhydrous dichloromethane (3.5 mL) and the solution stirred at room temperature for 18 h under nitrogen. The reaction is filtered and treated with methanol and stirred for 5 minutes. The reaction is concentrated in vacuo and the residue purified by silica gel chromatography eluting with 30-100% hexanes/EtOAc to afford the title compound as a white solid (43 mg, 20% yield).

Intermediate 168: 1-{N-[(methyloxy)carbonyl]-L-valyl}-8-oxa-1-azaspiro[4.5]decane-2-carboxylic acid

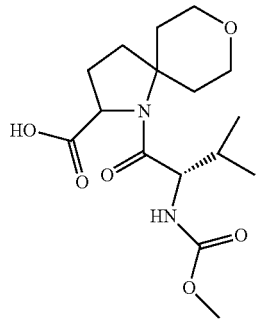 [SMILES: COC(=O)N[C@H](C(=O)N1C(C(=O)O)CCC12CCOCC2)C(C)C]

To a solution of ethyl 1-{N-[(methyloxy)carbonyl]-L-valyl}-8-oxa-1-azaspiro[4.5]decane-2-carboxylate (167) (80 mg, 0.2 mmol) in THF/water/methanol (1.0 mL/0.5 mL/0.5 mL) was added lithium hydroxide monohydrate (13 mg, 0.3 mmol) and the reaction stirred at room temperature for 72 h. The reaction was treated with 1N HCl (0.5 mL) and the reaction partitioned between EtOAc and 0.1 N HCl. The organic layer was separated and dried over MgSO₄ and concentrated in vacuo to afford the title compound as a white solid (53 mg, 72% yield). $^1$H NMR (400 MHz, DMSO-d$_6$) δ ppm 12.88 (br. s., 1H) 7.45-7.61 (m, 1H) 4.89-5.03 (m, 1H) 3.70-3.87 (m, 2H) 3.65 (t, J=9.2 Hz, 1H) 3.53 (s, 3H) 3.02 (td, J=12.9, 4.9 Hz, 1H) 2.71-2.90 (m, 1H) 2.22-2.38 (m, 1H) 1.87-2.19 (m, 3H) 1.53-1.73 (m, 1H) 1.32-1.42 (m, 1H) 1.06-1.15 (m, 1H) 0.61-0.98 (m, 8H). LC-MS ESI (M+H)$^+$=342.95.

Intermediate 169: methyl ((1S)-2-methyl-1-{[(2S)-2-(4-{4-[({[1-((2S)-3-methyl-2-{[(methyloxy)carbonyl]amino}butanoyl)-8-oxa-1-azaspiro[4.5]dec-2-yl]carbonyl}amino)acetyl]-4-biphenylyl}-1H-imidazol-2-yl)-1-pyrrolidinyl]carbonyl}propyl)carbamate To a solution of 1-{N-[(methyloxy)carbonyl]-L-valyl}-8-oxa-1-azaspiro[4.5]decane-2-carboxylic acid (168) (52 mg, 1.5 mmol) and methyl {(1S)-1-[((2S)-2-{4-[4'-(amino-acetyl)-4-biphenylyl]-1H-imidazol-2-yl}-1-pyrrolidinyl)carbonyl]-2-methylpropyl}carbamate dihydrochloride (1) (88 mg, 0.15 mmol) and HATU (58 mg, 0.15 mmol) in anhydrous dichloromethane (1.2 mL) was added Hunig's base (0.12 mL, 0.68 mmol) and the reaction stirred at room temperature for 1 h. The reaction was concentrated in vacuo and purified by HPLC eluting with 10-90% water/acetonitrile/0.2% NH₄OH to afford the title compound as an off-white solid (73 mg, 58% yield).

Example 31 methyl ((1S)-1-{[(2S)-2-(4-{4'-[2-(1-acetyl-8-oxa-1-azaspiro[4.5]dec-2-yl)-1H-imidazol-4-yl]-4-biphenylyl}-1H-imidazol-2-yl)-1-pyrrolidinyl}carbonyl]-2-methylpropyl)carbamate

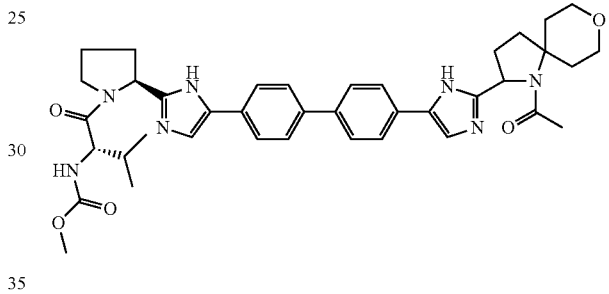

This compound was prepared in an analogous fashion to Example 30 from methyl {(1S)-1-[((2S)-2-{4-[4'-({[(1-acetyl-8-oxa-1-azaspiro[4.5]dec-2-yl)carbonyl]amino}acetyl)-4-biphenylyl]-1H-imidazol-2-yl}-1-pyrrolidinyl)carbonyl]-2-methylpropyl}carbamate (172) (116 mg, 0.16 mmol) to afford the title compound as a tan solid (19 mg, 17% yield). $^1$H NMR (400 MHz, METHANOL-d$_4$) δ ppm 7.51-7.90 (m, 8H) 7.17-7.52 (m, 2H) 5.08-5.26 (m, 2H) 3.81-4.03 (m, 4H) 3.64 (s, 3H) 3.41-3.61 (m, 3H) 2.21-2.51 (m, 5H) 2.01-2.21 (m, 4H) 1.97 (d, J=19.9 Hz, 5H) 1.77-1.91 (m, 1H) 1.64-1.75 (m, 1H) 1.31-1.42 (m, 1H) 0.79-1.04 (m, 8H). HRMS for C$_{39}$H$_{48}$N$_7$O$_5$ (M+H)$^+$ calc: 694.3717. found: 694.3718. Purity (LC-MS): 79%.

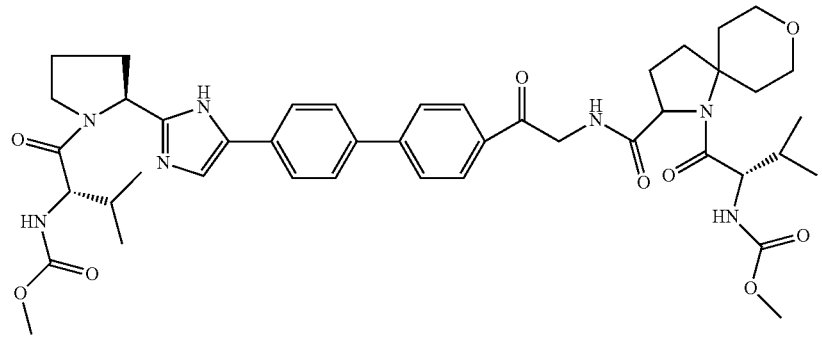 [SMILES: COC(=O)N[C@H](C(=O)N1CCC[C@H]1c1ncc(-c2ccc(-c3ccc(C(=O)CNC(=O)C4CCC5(CCOCC5)N4C(=O)[C@@H](NC(=O)OC)C(C)C)cc3)cc2)[nH]1)C(C)C]

Preparation of Intermediate 172

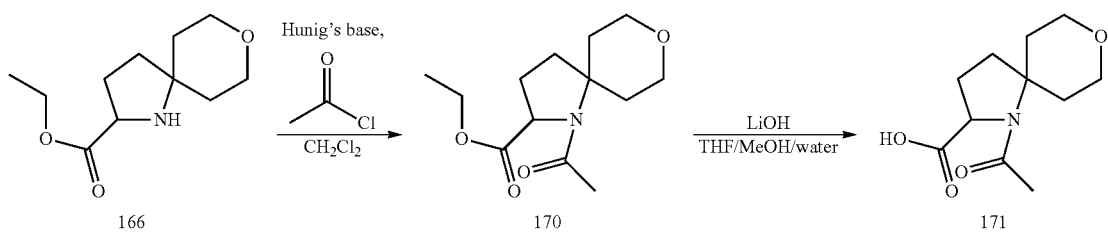

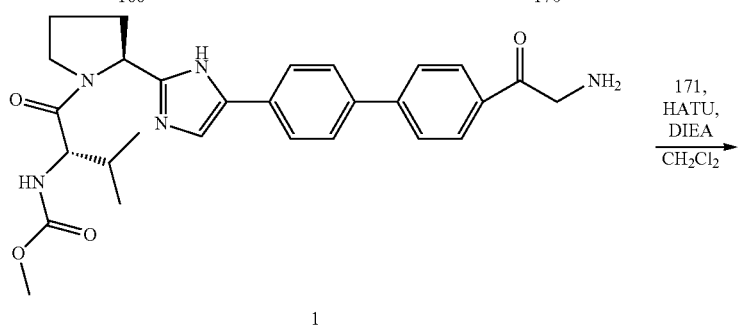

Intermediate 170: ethyl 1-acetyl-8-oxa-1-azaspiro[4.5]decane-2-carboxylate

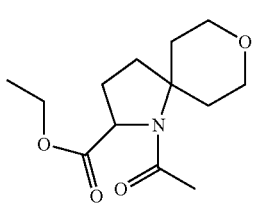 [SMILES: CCOC(=O)C1CCC2(CCOCC2)N1C(C)=O]

To a solution of ethyl 8-oxa-1-azaspiro[4.5]decane-2-carboxylate (166) (135 mg, 0.63 mmol) in anhydrous dichloromethane (2 mL) was added Hunig's base (0.22 mL, 1.3 mmol) followed by acetyl chloride (0.05 mL, 0.76 mmol) and the reaction stirred at room temperature under nitrogen for 1.5 h. The reaction was diluted with dichloromethane and washed with 0.1 N HCl and the organic layer dried over MgSO$_4$ and concentrated in vacuo. The residue was purified by silica gel chromatography eluting with 60-100% hexanes/EtOAc to afford the title compound as a yellow oil (94 mg, 58% yield).

Intermediate 171: 1-acetyl-8-oxa-1-azaspiro[4.5]decane-2-carboxylic acid

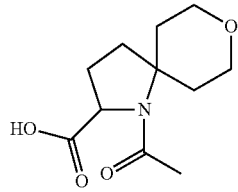 [SMILES: CC(=O)N1C(C(=O)O)CCC12CCOCC2]

To a solution of ethyl 1-acetyl-8-oxa-1-azaspiro[4.5]decane-2-carboxylate (170) (93 mg, 0.34 mmol) in THF/water/methanol (1.1 mL/0.6 mL/0.6 mL) was added lithium hydroxide monohydrate (29 mg, 0.69 mmol) and the reaction stirred at room temperature for 3 h. The reaction is treated with 1N HCl (0.7 mL) and partitioned between EtOAc and 0.1 N HCl, the aqueous layer was extracted twice with EtOAc, the combined organic layers were dried over MgSO$_4$ and concentrated in vacuo to afford the title compound as a white solid (79 mg, 95% yield).

Intermediate 172: methyl {(1S)-1-[((2S)-2-{4-[4'-({[(1-acetyl-8-oxa-1-azaspiro[4.5]dec-2-yl)carbonyl]amino}acetyl)-4-biphenylyl]-1H-imidazol-2-yl}-1-pyrrolidinyl)carbonyl]-2-methylpropyl}carbamate

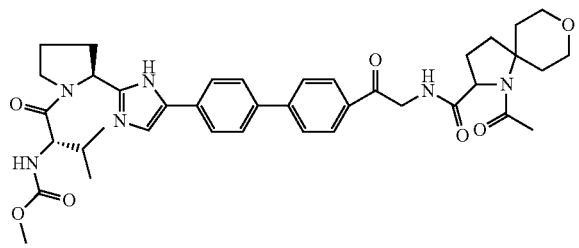 [SMILES: COC(=O)N[C@H](C(=O)N1CCC[C@H]1c1ncc(-c2ccc(-c3ccc(C(=O)CNC(=O)C4CCC5(CCOCC5)N4C(C)=O)cc3)cc2)[nH]1)C(C)C]

This compound was prepared in an analogous fashion to 169 from 1-acetyl-8-oxa-1-azaspiro[4.5]decane-2-carboxylic acid (171) (56 mg, 0.25 mmol) and methyl {(1S)-1-[((2S)-2-{4-[4'-(aminoacetyl)-4-biphenylyl]-1H-imidazol-2-yl}-1-pyrrolidinyl)carbonyl]-2-methylpropyl}carbamate dihydrochloride (1) (142 mg, 0.25 mmol) to afford the title compound as an off-white solid (118 mg, 67% yield). Examples 32 to 37 were prepared, using the synthetic sequence similar to Examples 30 and 31.

Example 32 methyl [(1S)-1-({(2S)-2-[4-(4'-{2-[8,8-difluoro-1-((2S)-3-methyl-2-{[(methyloxy)carbonyl]amino}butanoyl)-1-azaspiro[4.5]dec-2-yl]-1H-imidazol-4-yl}-4-biphenylyl)-1H-imidazol-2-yl]-1-pyrrolidinyl}carbonyl)-2-methylpropyl]carbamate

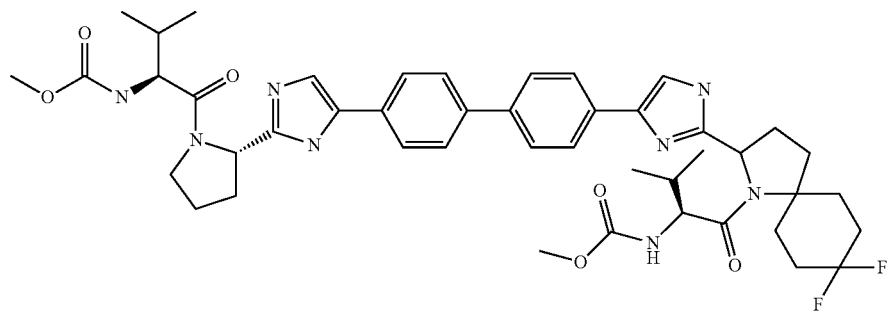 [SMILES: COC(=O)N[C@H](C(=O)N1CCC[C@H]1c1ncc(-c2ccc(-c3ccc(-c4c[nH]c(C5CCC6(CCC(F)(F)CC6)N5C(=O)[C@@H](NC(=O)OC)C(C)C)n4)cc3)cc2)[nH]1)C(C)C]

$^1$H NMR (400 MHz, METHANOL-$d_4$) δ 7.92-7.51 (m, 8H), 7.29 (br. s., 2H), 5.71 (br. s., 1H), 5.32 (br. s., 1H), 4.21 (d, J=7.4 Hz, 1H), 4.15-3.80 (m, 4H), 3.77-3.41 (m, 8H), 3.18 (br. s., 1H), 3.12-2.82 (m, 1H), 2.63-1.40 (m, 16H), 1.05-0.84 (m, 10H), 0.78-0.64 (m, 1H), 0.44-0.28 (m, 1H). HRMS for C45H57F2N8O6 (M+H)$^+$ calc: 843.4369. found: 843.4368.

Example 33 methyl [(1S)-1-({8,8-difluoro-2-[4-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-1H-imidazol-2-yl]-1-azaspiro[4.5]dec-1-yl}carbonyl)propyl]carbamate

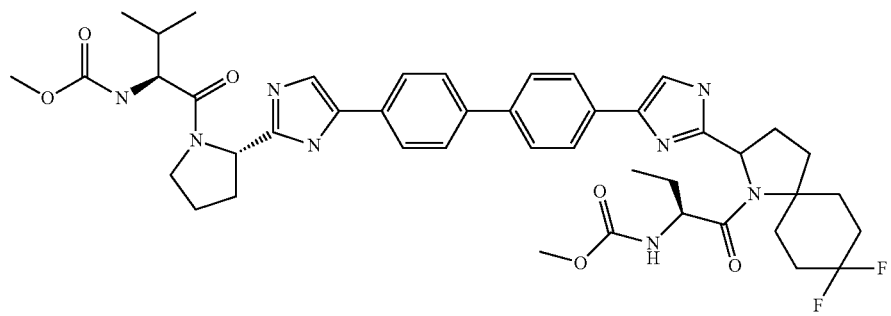 [SMILES: CC[C@H](NC(=O)OC)C(=O)N1C(c2nc(-c3ccc(-c4ccc(-c5cnc([C@@H]6CCCN6C(=O)[C@@H](NC(=O)OC)C(C)C)[nH]5)cc4)cc3)c[nH]2)CCC12CCC(F)(F)CC2]

¹H NMR (400 MHz, CHLOROFORM-d) δ 7.84 (d, J=7.8 Hz, 3H), 7.72-7.41 (m, 6H), 7.31-7.09 (m, 3H), 5.73-5.17 (m, 4H), 5.12 (br. s., 1H), 4.41-4.06 (m, 3H), 3.97-3.56 (m, 11H), 3.37-2.76 (m, 4H), 2.60-1.55 (m, 9H), 1.46-1.20 (m, 2H), 1.06 (d, J=6.0 Hz, 2H), 1.00-0.79 (m, 5H), 0.56 (d, J=7.3 Hz, 1H). HRMS for C44H55F2N8O6 (M+H)⁺ calc: 829.4213. found: 829.4211.

Example 34 methyl ((1S)-2-{8,8-difluoro-2-[4-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-1H-imidazol-2-yl]-1-azaspiro[4.5]dec-1-yl}-1-methyl-2-oxoethyl)carbamate

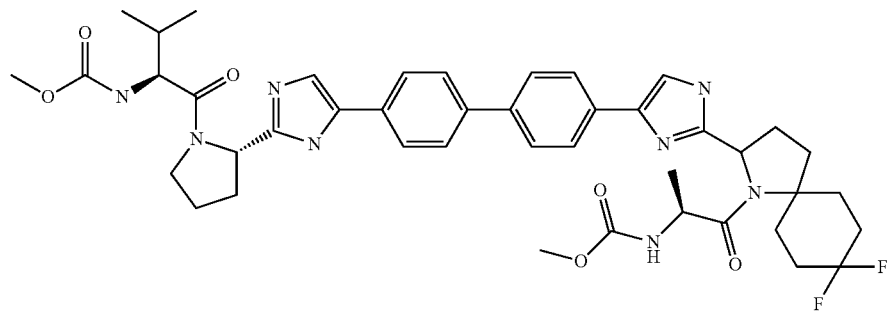 [SMILES: COC(=O)N[C@@H](C)C(=O)N1C(c2nc(-c3ccc(-c4ccc(-c5cnc([C@@H]6CCCN6C(=O)[C@@H](NC(=O)OC)C(C)C)[nH]5)cc4)cc3)c[nH]2)CCC12CCC(F)(F)CC2]

¹H NMR (400 MHz, CHLOROFORM-d) δ 10.97-10.14 (m, 2H), 7.91-7.40 (m, 8H), 7.34-7.16 (m, 2H), 5.68-5.15 (m, 3H), 5.08 (d, J=6.0 Hz, 1H), 4.34 (d, J=8.0 Hz, 2H), 3.95-3.54 (m, 8H), 3.37-2.69 (m, 4H), 2.60-1.57 (m, 13H), 1.56-1.18 (m, 3H), 1.06 (d, J=6.8 Hz, 1H), 0.89 (d, J=6.5 Hz, 6H). HRMS for C43H53F2N8O6 (M+H)⁺ calc: 815.4056. found: 815.4061.

Example 35 methyl [(1S)-1-({8,8-difluoro-2-[4-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-1H-imidazol-2-yl]-1-azaspiro[4.5]dec-1-yl}carbonyl)-3-methylbutyl]carbamate

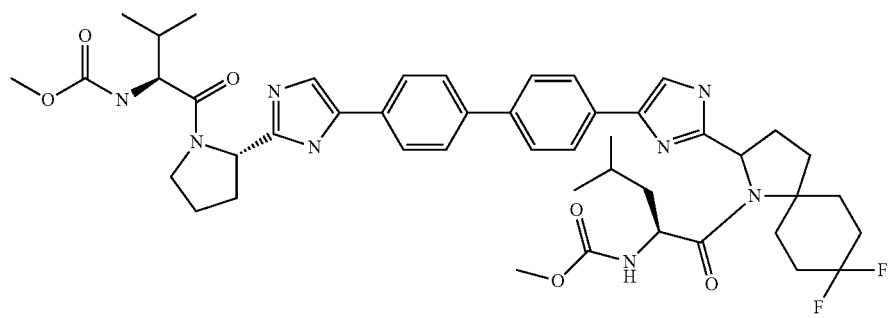 [SMILES: COC(=O)N[C@@H](CC(C)C)C(=O)N1C(c2nc(-c3ccc(-c4ccc(-c5cnc([C@@H]6CCCN6C(=O)[C@@H](NC(=O)OC)C(C)C)[nH]5)cc4)cc3)c[nH]2)CCC12CCC(F)(F)CC2]

¹H NMR (400 MHz, CHLOROFORM-d) δ 11.07-9.94 (m, 2H), 8.17-7.42 (m, 10H), 7.33-7.08 (m, 2H), 5.72-5.19 (m, 3H), 5.14-4.99 (m, 1H), 4.86 (br. s., 1H), 4.50-4.09 (m, 2H), 4.02-3.50 (m, 8H), 3.45 (s, 1H), 3.33-2.71 (m, 4H), 2.59-1.47 (m, 11H), 1.40 (br. s., 3H), 1.19-0.67 (m, 11H), 0.63-0.40 (m, 1H).). HRMS for C46H59F2N8O6 (M+H)⁺ calc: 857.4526. found: 857.4531.

Example 36 methyl ((1S)-1-{[(2S)-2-(4-{4'-[2-(1-acetyl-8,8-difluoro-1-azaspiro[4.5]dec-2-yl)-1H-imidazol-4-yl]-4-biphenylyl}-1H-imidazol-2-yl)-1-pyrrolidinyl]carbonyl}-2-methylpropyl)carbamate

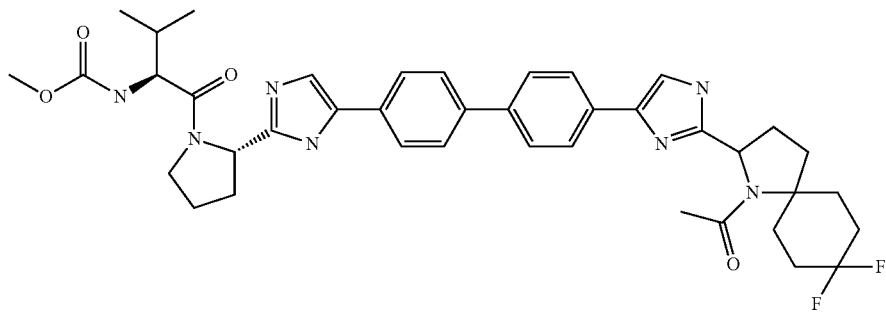 [SMILES: COC(=O)N[C@H](C(=O)N1CCC[C@H]1c1ncc(-c2ccc(-c3ccc(-c4c[nH]c(C5CCC6(CCC(F)(F)CC6)N5C(C)=O)n4)cc3)cc2)[nH]1)C(C)C]

$^1$H NMR (400 MHz, CHLOROFORM-d) δ 11.17-10.07 (m, 2H), 8.16-7.40 (m, 10H), 7.35-7.03 (m, 2H), 5.85-4.98 (m, 2H), 4.59-4.12 (m, 1H), 3.72 (s, 5H), 3.46 (br. s., 1H), 3.33-2.72 (m, 2H), 2.76-1.39 (m, 17H), 1.27-0.74 (m, 5H). HRMS for $C_{40}H_{48}F_2N_7O_4$ $(M+H)^+$ calc: 728.3736. found: 728.3736.

Example 37 methyl [(1S)-2-methyl-1-({(2S)-2-[4-(4'-{2-[1-((2S)-3-methyl-2-{[(methyloxy)carbonyl]amino}butanoyl)-8,8-dioxido-8-thia-1-azaspiro[4.5]dec-2-yl]-1H-imidazol-4-yl}-4-biphenylyl)-1H-imidazol-2-yl]-1-pyrrolidinyl}carbonyl)propyl] carbamate

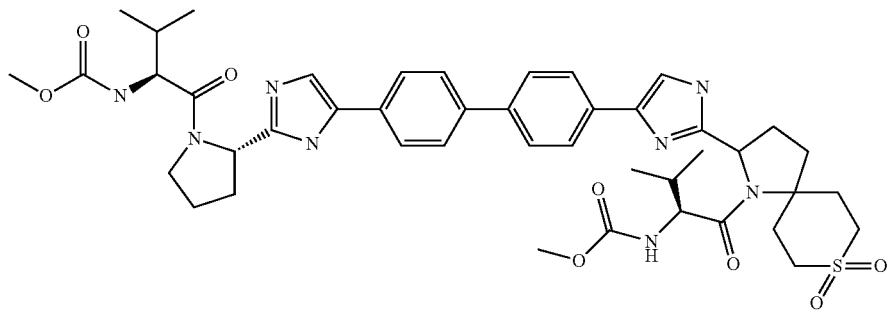 [SMILES: COC(=O)N[C@H](C(=O)N1CCC[C@H]1c1ncc(-c2ccc(-c3ccc(-c4c[nH]c(C5CCC6(CCS(=O)(=O)CC6)N5C(=O)[C@@H](NC(=O)OC)C(C)C)n4)cc3)cc2)[nH]1)C(C)C]

$^1$H NMR (400 MHz, CHLOROFORM-d) δ 7.92-7.52 (m, 9H), 5.39 (br. s., 4H), 4.36 (br. s., 1H), 3.98-3.82 (m, 1H), 3.82-3.60 (m, 10H), 3.19 (br. s., 4H), 2.88-2.70 (m, 1H), 2.33 (br. s., 4H), 2.02 (s, 4H), 1.81 (br. s., 5H), 1.06 (s, 1H), 0.89 (d, J=7.0 Hz, 6H), 0.74 (d, J=6.5 Hz, 3H), 0.44-0.34 (m, 3H). HRMS for $C_{44}H_{57}N_8O_8S$ $(M+H)^+$ calc: 857.4020. found: 857.4018.

Protocol for Testing and Data Analysis of Compounds in the HCV Replicon Assay

Compounds were assayed for activity against HCV using the genotype 1a and 1b subgenomic replicon model systems. Stable cell lines bearing the genotype 1a and 1b replicons were used for screening of compounds. Both replicons are bicistronic and contain the firefly luciferase gene. The ET cell line is stably transfected with RNA transcripts harboring a $I_{389}$luc-ubi-neo/NS3-3'/ET replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The genotype 1a replicon is a stable cell line licensed from Apath LLC, modified to contain the firefly luciferase gene. The cells were grown in DMEM, supplemented with 10% fetal calf serum, 2 mM Glutamine, Penicillin (100 IU/mL)/Streptomycin (100 μg/mL), 1× nonessential amino acids, and 250-500 μg/mL G418 ("Geneticin"). They were all available through Life Technologies (Bethesda, Md.). The cells were plated at 5×10$^3$ cells/well in 384 well plates containing compounds. The final concentration of compounds ranged between 0.03 pM to 50 μm and the final DMSO concentration of 0.5-1%.

Luciferase activity was measured 48 hours later by adding a Steady glo reagent (Promega, Madison, Wis.). Percent inhibition of replication data was plotted relative to no compound control. Under the same condition, cytotoxicity of the compounds was determined using cell titer glo (Promega, Madison, Ws). EC50s were determined from an 11 point dose response curve using 3-4-fold serial dilution for each compound, which spans a concentration range >1000 fold. The level of inhibition for each compound was determined with Activity Base or with BioAssay plus the Excel XC50 module. Percent inhibition was determined with the following equation where the cross-talk corrected value is the value from the test well, the compound positive control mean is the average value of the wells with no compound present, and the DMSO negative control mean is the average value of the wells with DMSO but no cells present.

$$100 * (1 - \frac{(\text{Cross-talk corrected value} - \text{Compound Positive Control Mean})}{\text{DMSO Negative Control Mean} - \text{Compound Positive Control Mean}})$$

These normalized values are exported to $EC_{50}$ where they are plotted against the molar compound concentrations using the standard four parameter logistic equation:

$$y = A + \frac{B - A}{1 + \left[\frac{10^x}{10^c}\right]^D}$$

Where:

$A = \text{minimum } y$ $B = \text{maximum } y$ $C = \log_{10} EC_{50}$ $D = \text{slope factor}$ $x = \log_{10} \text{ compound concentration } [M]$ $pEC_{50} = -C$ As shown below, all tested compounds, except for Example 20, were found to inhibit the activity of the replicon with $pEC_{50} > 5$.

| | Replicon 1A $pEC_{50}$ | Replicon 1B $pEC_{50}$ |
|---|---|---|
| Example 1 | 8.8 | 11.0 |
| Example 2 | 10.4 | 11.1 |
| Example 3 | 7.6 | 10.8 |
| Example 4 | 10.4 | 11.0 |
| Example 5 | 10.1 | 10.7 |
| Example 6 | 10.6 | 11.1 |
| Example 7 | 9.1 | 11.6 |
| Example 8 | 10.5 | 11.1 |
| Example 9 | 10.5 | 11.2 |
| Example 10 | 8.7 | 11.0 |
| Example 11 | 8.9 | 11.0 |
| Example 12 | 10.1 | 11.4 |
| Example 13 | 10.2 | 11.4 |
| Example 14 | 9.2 | 11.3 |
| Example 15 | 10.2 | 10.8 |
| Example 16 | 9.4 | 10.4 |
| Example 17 | 10.4 | 11.6 |
| Example 18 | 10.7 | 10.9 |
| Example 19 | 8.0 | 10.4 |
| Example 20 | <7.5 | 8.8 |
| Example 21 | 8.0 | 9.7 |
| Example 22 | 9.1 | 10.8 |
| Example 23 | 8.9 | 11.0 |
| Example 24 | 8.5 | 9.9 |
| Example 25 | 8.9 | 9.8 |
| Example 26 | 8.7 | 10.3 |
| Example 27 | 8.2 | 9.6 |
| Example 28 | 8.8 | 10.3 |
| Example 29 | 10.0 | 11.5 |
| Example 30 | 8.8 | 10.2 |
| Example 31 | 9.5 | 10.9 |
| Example 32 | 8.8 | 10.8 |
| Example 33 | 9.0 | 10.8 |
| Example 34 | 9.2 | 11.0 |
| Example 35 | 8.7 | 10.9 |
| Example 36 | 7.6 | 10.0 |
| Example 37 | 7.9 | 9.5 |

Preparation of crystalline salts of the compound of Example 2: methyl [(1S)-2-methyl-1-({(2S)-2-[4-(4'-{2-[(8S)-7-((2S)-3-methyl-2-{[(methyloxy)carbonyl]amino}butanoyl)-1,4-dioxa-7-azaspiro[4.4]non-8-yl]-1H-imidazol-4-yl}-4-biphenylyl)-1H-imidazol-2-yl]-1-pyrrolidinyl}carbonyl)propyl]carbamate.

Crystalline Di-HCl Salt of the Compound of Example 2:

WO 2009/020828 discloses the crystalline di-HCl salt of a compound said to be useful for treating HCV infection. The title compound of WO 2009/020828 was prepared as described in that patent.

The compound of Example 2 was isolated and purified as the amorphous free-base. This amorphous free-base was dissolved in acetone (3.6 mL; 30 vol) at room temperature with stirring. Hydrochloric acid (316 uL of 1.0M in dioxane; 2.1 equivalents) was added and resulted in an amorphous precipitate. Methanol (480 uL; 4 vol) was added in aliquots until solids just dissolved. Crystalline seeds of the WO 2009/020828 di-HCl compound were added, and the mixture stirred over the weekend. The product was filtered with no wash, and the yield was 62.6% (84.0 mg; 0.0946 mmol) of crystalline di-HCl salt of the compound of Example 2.

Crystalline Di-HCl Salt of the Compound of Example 2:

The compound of Example 2 was isolated and purified as the amorphous free-base. This amorphous free-base (555 mg; 0.696 mmol) was dissolved in acetone (8.3 mL; 15 vol) and methanol (2.2 mL; 4 vol) at 50° C. with stirring. Hydrochloric acid (1.46 mL of 1.0M in dioxane; 2.1 equivalents) was added slowly followed by seed crystals of the di-HCl salt of the compound of Example 2. The slurry was maintained at 50° C. for one hour, cooled to room temperature, and stirred over the weekend. The product was quickly filtered with no wash and dried at 50° C. in a vacuum oven with nitrogen bleed. The yield was 54.0% (327 mg; 0.376 mmol) of crystalline di-HCl salt of the compound of Example 2.

Crystalline Sulfate Salt of the Compound of Example 2:

The amorphous sulfate salt of the compound of Example 2 was prepared by adding 1.0 eq of sulfuric acid to a solution of free-base and concentrating to dryness. The amorphous sulfate salt (~50 mg; 0.056 mmol) was taken up in acetone (750 ul; 15 volumes), and the mixture was heated to 50° C. Methanol (210 ul; 4.2 vol) was added 10 uL at a time until the solids almost all dissolved, resulting in a cloudy solution. This cloudy solution was mixed at 50° C. for 16 hours, then cooled to 23° C. The product was filtered, analyzed, and determined to be consistent with crystalline sulfate salt of the compound of Example 2.

Crystalline Sulfate Salt of the Compound of Example 2:

The amorphous free-base of the compound of Example 2 (250 mg; 0.314 mmol) was mixed with methanol (1.25 mL; 5 vol) and heated to 50° C. with stirring to accelerate dissolution. Sulfuric acid (0.105 mL of 3.0M in water; 1.0 equivalent) was added slowly followed by seed crystals of the sulfate salt of the compound of Example 2. The slurry was maintained at 50° C. for three hours to form a moderately thick, yellow slurry. The temperature was decreased to 15° C. to increase the yield. The product was filtered with no wash and dried at 50° C. in a vacuum oven with nitrogen bleed. The yield was 73.6% (211 mg; 0.231 mmol) of crystalline sulfate salt of GSK2336805.

Analysis of Crystalline Salts:

The crystalline di-HCl and sulfate salts of the compound of Example 2 were analyzed by ion chromatography, powder X-ray diffraction (PXRD), Raman, DSC, and TGA. All analyses were consistent with crystalline salts.

The powder X-ray diffraction was performed with a PANalytical X'Pert-Pro MPD with Johansson Kα1 monochromator, using X'Celerator detector. The key operating parameters were: Radiation: Cu (Kα1), 1.54060 angstroms (monochromatic); Detector: X'Celerator; Tension: 45 kV; Current: 40 mA; Start angle: 2.0°□2θ; End angle: 50.0°□2θ; Step size: 0.02°; Time/step: 40.0 sec; Scan speed: 0.05°/sec; Incident beam: 2° fixed anti-scatter slit, and programmable divergence slit; Diffracted beam: 0.02 rad soller slit, and programmable anti-scatter slit. Samples were prepared on silicon zero background sample holder.

The di-HCl salt of the compound of Example 2 had significant peaks in powder X-ray diffraction pattern at values of two theta in degrees and d-spacing in Angstrom in parenthesis of 5.3(16.55), 9.9 (8.94), 10.4 (8.54), 13.3(6.65), 18.9(4.70), 20.3(4.37), 21.2(4.18), 22.5(3.95), 23.2(3.84), 23.7(3.75), 24.4(3.65), 26.3(3.39), 27.6(3.23). The TGA trace of the di-HCl salt of the compound of Example 2 was consistent with an anhydrous form. The DSC trace of the di-HCl salt of the compound of Example 2 showed an onset of melting and/or decomposition at approximately 262° C.

The sulfate salt of the compound of Example 2 had significant peaks in powder X-ray diffraction pattern at values of two theta in degrees and d-spacing in Angstrom of 5.6(15.87), 7.1(12.39), 8.0(11.10), 10.5(8.41), 11.9(7.41), 12.6(7.02), 13.4(6.61), 14.3(6.18), 16.6(5.33), 17.5(5.07), 18.4(4.81), 20.0(4.43), 21.2(4.19), 23.8(3.73). The TGA trace of the sulfate salt of the compound of Example 2 was consistent with a variable hydrate form. The DSC trace of the sulfate salt of the compound of Example 2 showed an onset of melting and/or decomposition at approximately 241° C.

What is claimed is:

1. A pharmaceutical composition comprising a compound of Formula II

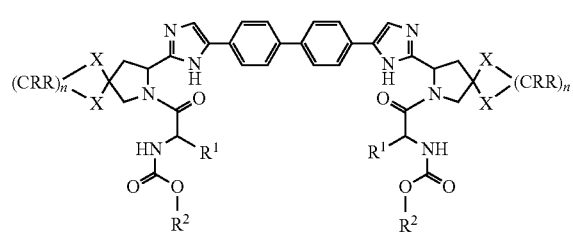

II wherein each $R^1$ is independently H or $C_{1-3}$alkyl;
each $R^2$ is independently $C_{1-3}$alkyl;
each X is independently CRR, O, or S;
each n is independently 2 or 3; and
each R is independently methyl, hydrogen, or deuterium; and
one or more therapeutic agents.

2. A pharmaceutical composition as claimed in claim 1 wherein said one or more therapeutic agents is interferon.

3. A pharmaceutical composition as claimed in claim 1 wherein said one or more therapeutic agents is ribavirin.

4. A pharmaceutical composition as claimed in claim 1 wherein said therapeutic agents are interferon and ribavirin.

5. A pharmaceutical composition comprising a compound selected from the group consisting of:
methyl [(1S)-1-({(2S)-2-[4-(4'-{2-[(3S,7S,9S)-7,9-dimethyl-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate;
methyl [(1S)-2-methyl-1-({(2S)-2-[4-(4'-{2-[(8S)-7-((2S)-3-methyl-2-{[(methyloxy)carbonyl]amino}butanoyl)-1,4-dioxa-7-azaspiro[4.4]non-8-yl]-1H-imidazol-4-yl}-4-biphenylyl)-1H-imidazol-2-yl]-1-pyrrolidinyl}carbonyl)propyl]carbamate;
dimethyl (4,4'-biphenyldiylbis{1H-imidazole-4,2-diyl[(3S,7S,9S)-7,9-dimethyl-6,10-dioxa-2-azaspiro[4.5]decane-3,2-diyl][(2S)-3-methyl-1-oxo-1,2-butanediyl]})biscarbamate;
dimethyl (4,4'-biphenyldiylbis{1H-imidazole-4,2-diyl(8S)-1,4-dioxa-7-azaspiro[4.4]nonane-8,7-diyl[(2S)-3-methyl-1-oxo-1,2-butanediyl]})biscarbamate;
methyl ((1S)-1-methyl-2-{(3S)-3-[4-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-1H-imidazol-2-yl]-6,10-dioxa-2-azaspiro[4.5]dec-2-yl}-2-oxoethyl)carbamate;
methyl [(1S)-2-methyl-1-({(2S)-2-[4-(4'-{2-[(3 S)-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)propyl]carbamate;
methyl [(1S)-1-({(2S)-2-[4-(4'-{2-[(3S)-8,8-dimethyl-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate;
methyl [(1S)-2-methyl-1-({(2S)-2-[4-(4'-{2-[(3S)-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)propyl]carbamate-$d_6$,
methyl [(1S)-2-methyl-1-({(2S)-2-[4-(4'-{2-[(8S)-7-((2S)-3-methyl-2-{[(methyloxy)carbonyl]amino}butanoyl)-1,4-dioxa-7-azaspiro[4.4]non-8-yl]-1H-imidazol-4-yl}-4-biphenylyl)-1H-imidazol-2-yl]-1-pyrrolidinyl}carbonyl)propyl]carbamate-$d_4$;
methyl [(1S)-1-({(2S)-2-[4-(4'-{2-[(2R,3R,8S)-2,3-dimethyl-7-((2S)-3-methyl-2-{[(methyloxy)carbonyl]amino}butanoyl)-1,4-dioxa-7-azaspiro[4.4]non-8-yl]-1H-imidazol-5-yl}-4-biphenylyl)-1H-imidazol-2-yl]-1-pyrrolidinyl}carbonyl)-2-methylpropyl]carbamate;
methyl [(1S)-1-({(2S)-2-[4-(4'-{2-[(2S,3S,8S)-2,3-dimethyl-7-((2S)-3-methyl-2-{[(methyloxy)carbonyl]amino}butanoyl)-1,4-dioxa-7-azaspiro[4.4]non-8-yl]-1H-imidazol-5-yl}-4-biphenylyl)-1H-imidazol-2-yl]-1-pyrrolidinyl}carbonyl)-2-methylpropyl]carbamate;
methyl [(1S)-2-methyl-1-({(2S)-2-[4-(4'-{2-[(8S)-7-((2S)-3-methyl-2-{[(methyloxy)carbonyl]amino}butanoyl)-1,4-dithia-7-azaspiro[4.4]non-8-yl]-1H-imidazol-4-yl}-4-biphenylyl)-1H-imidazol-2-yl]-1-pyrrolidinyl}carbonyl)propyl]carbamate;

methyl [(1S)-2-methyl-1-({(2S)-2-[4-(4'-{2-[(8S)-7-((2S)-2-{[(methyloxy) carbonyl]amino}butanoyl)-1,4-dithia-7-azaspiro[4.4]non-8-yl]-1H-imidazol-4-yl}-4-biphenylyl)-1H-imidazol-2-yl]-1-pyrrolidinyl}carbonyl)propyl]carbamate;

methyl [(1S)-2-methyl-1-({(2S)-2-[4-(4'-{2-[(8S)-7-({[(methyloxy)carbonyl] amino}acetyl)-1,4-dithia-7-azaspiro[4.4]non-8-yl]-1H-imidazol-4-yl}-4-biphenylyl)-1H-imidazol-2-yl]-1-pyrrolidinyl}carbonyl)propyl]carbamate;

methyl [(1S)-2-methyl-1-({(2S)-2-[4-(4'-{2-[2-((2S)-3-methyl-2-{[(methyloxy)carbonyl]amino}butanoyl)-8-oxa-2-azaspiro[4.5]dec-3-yl]-1H-imidazol-4-yl-4-biphenylyl)-1H-imidazol-2-yl]-1-pyrrolidinyl}carbonyl)propyl]carbamate;

methyl [(1S)-2-methyl-1-({(2S)-2-[4-(4'-(2-[2-((2S)-3-methyl-2-{[(methyloxy)carbonyl]amino}butanoyl)-8,8-dioxido-8-thia-2-azaspiro[4.5]dec-3-yl]-1H-imidazol-4-yl}-4-biphenylyl)-1H-imidazol-2-yl]-1-pyrrolidinyl}carbonyl)propyl]carbamate;

methyl [(1S)-1-({(2S)-2-[4-(4'-{2-[8,8-difluoro-2-((2S)-3-methyl-2-{[(methyloxy)carbonyl]amino}butanoyl)-2-azaspiro[4.5]dec-3-yl]-1H-imidazol-4-yl}-4-biphenylyl)-1H-imidazol-2-yl]-1-pyrrolidinyl}) carbonyl)-2-methylpropyl]carbamate;

1,1-dimethylethyl 2-{N-[(methyloxy)carbonyl]-L-valyl}-3-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,8-diazaspiro[4.5]decane-8-carboxylate;

methyl [(1S)-2-methyl-1-({(2S)-2-[4-(4'-{2-[2-((2S)-3-methyl-2-{[(methyloxy)carbonyl]amino}butanoyl)-2,8-diazaspiro[4.5]dec-3-yl]-1H-imidazol-4-yl}-4-biphenylyl)-1H-imidazol-2-yl]-1-pyrrolidinyl}carbonyl)propyl]carbamate;

methyl [(1S)-1-({(2S)-2-[4-(4'-{2-[8-acetyl-2-((2S)-3-methyl-2-{[(methyloxy)carbonyl]amino}butanoyl)-2,8-diazaspiro[4.5]dec-3-yl]-1H-imidazol-4-yl}-4-biphenylyl)-1H-imidazol-2-yl]-1-pyrrolidinyl}) carbonyl)-2-methylpropyl]carbamate;

methyl 2-{N-[(methyloxy)carbonyl]-L-valyl}-3-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,8-diazaspiro[4.5]decane-8-carboxylate;

1,1-dimethylethyl 6-{N-[(methyloxy)carbonyl]-L-valyl}-7-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,6-diazaspiro[3.4]octane-2-carboxylate;

methyl [(1S)-2-methyl-1-({(2S)-2-[4-(4'-{2-[6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate;

methyl [(1S)-1-({(2S)-2-[4-(4'-{2-[2-acetyl-6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}) carbonyl)-2-methylpropyl]carbamate;

methyl 6-{N-[(methyloxy)carbonyl]-L-valyl}-7-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,6-diazaspiro[3.4]octane-2-carboxylate;

methyl [(1S)-2-methyl-1-({(2S)-2-[4-(4'-{2-[2-[(methylamino)carbonyl]-6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate;

methyl [(1S)-2-methyl-1-({(2S)-2-[4-(4'-{2-[6-((2S)-3-methyl-2-{[(methyloxy)carbonyl]amino}butanoyl)-2-(methylsulfonyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate;

methyl [(1S)-1-({(2S)-2-[4-(4'-{2-[(7S)-2,2-difluoro-6-((2S)-3-methyl-2-{[(methyloxy)carbonyl]amino}butanoyl)-6-azaspiro[3.4]oct-7-yl]-1H-imidazol-4-yl}-4-biphenylyl)-1H-imidazol-2-yl]-1-pyrrolidinyl}) carbonyl)-2-methylpropyl]carbamate;

methyl [(1S)-2-methyl-1-({(2S)-2-[4-(4'-{2-[1-((2S)-3-methyl-2-{[(methyloxy)carbonyl]amino}butanoyl)-8-oxa-1-azaspiro[4.5]dec-2-yl]-1H-imidazol-4-yl}-4-biphenylyl)-1H-imidazol-2-yl]-1-pyrrolidinyl}carbonyl)propyl]carbamate;

methyl ((1S)-1-{[(2S)-2-(4-{4'-[2-(1-acetyl-8-oxa-1-azaspiro[4.5]dec-2-yl)-1H-imidazol-4-yl]-4-biphenylyl}-1H-imidazol-2-yl)-1-pyrrolidinyl]carbonyl}-2-methylpropyl)carbamate;

methyl [(1S)-1-({(2S)-2-[4-(4'-{2-[8,8-difluoro-1-((2S)-3-methyl-2-{[(methyloxy) carbonyl]amino}butanoyl)-1-azaspiro[4.5]dec-2-yl]-1H-imidazol-4-yl}-4-biphenylyl)-1H-imidazol-2-yl]-1-pyrrolidinyl}carbonyl)-2-methylpropyl]carbamate;

methyl [(1S)-1-({8,8-difluoro-2-[4-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-1H-imidazol-2-yl]-1-azaspiro[4.5]dec-1-yl}carbonyl)propyl]carbamate;

methyl ((1S)-2-{8,8-difluoro-2-[4-(4'-{2-[(2S)-1-((2S)-3-methyl-2-{[(methyloxy) carbonyl]amino}butanoyl)-2-pyrrolidinyl]-1H-imidazol-4-yl}-4-biphenylyl)-1H-imidazol-2-yl]-1-azaspiro[4.5]dec-1-yl}-1-methyl-2-oxoethyl)carbamate;

methyl [(1S)-1-({8,8-difluoro-2-[4-(4'-{2-[(2S)-1-((2S)-3-methyl-2-{[(methyloxy) carbonyl]amino}butanoyl)-2-pyrrolidinyl]-1H-imidazol-4-yl}-4-biphenylyl)-1H-imidazol-2-yl]-1-azaspiro[4.5]dec-1-yl}carbonyl)-3-methylbutyl]carbamate;

methyl ((1S)-1-{[(2S)-2-(4-{4'-[2-(1-acetyl-8,8-difluoro-1-azaspiro[4.5]dec-2-yl)-1H-imidazol-4-yl]-4-biphenylyl}-H-imidazol-2-yl)-1-pyrrolidinyl]carbonyl}-2-methylpropyl)carbamate; and methyl [(1S)-2-methyl-1-({(2S)-2-[4-(4'-{2-[1-((2S)-3-methyl-2-{[(methyloxy) carbonyl]amino}butanoyl)-8,8-dioxido-8-thia-1-azaspiro[4.5]dec-2-yl]-H-imidazol-4-yl}-4-biphenylyl)-1H-imidazol-2-yl]-1-pyrrolidinyl}carbonyl)propyl]carbamate; and pharmaceutically acceptable salts thereof, and one or more therapeutic agents.

6. A pharmaceutical composition as claimed in claim 5 wherein said one or more therapeutic agents is interferon.

7. A pharmaceutical composition as claimed in claim 5 wherein said one or more therapeutic agents is ribavirin.

8. A pharmaceutical composition as claimed in claim 5 wherein said therapeutic agents are interferon and ribavirin.

9. A method of treating an HCV viral infection in a patient in need comprising the steps of:

(a) administering to the patient in need a therapeutically effective amount of a compound of Formula II

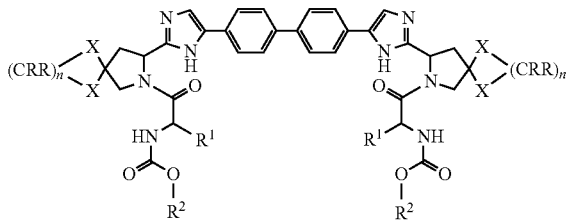

II wherein each $R^1$ is independently H or $C_{1-3}$alkyl;
each $R^2$ is independently $C_{1-3}$alkyl;
each X is independently CRR, O, or S;
each n is independently 2 or 3; and
each R is independently methyl, hydrogen, or deuterium; and (b) administering to the patient in need one or more therapeutic agents.

10. A method as claimed in claim 9 wherein said one or more therapeutic agents is interferon.

11. A method as claimed in claim 9 wherein said one or more therapeutic agents is ribavirin.

12. A method as claimed in claim 9 wherein said therapeutic agents are interferon and ribavirin.

13. A method of treating an HCV viral infection to a patient in need comprising the steps of:
(a) administering to the patient in need a therapeutically effective amount of a compound selected from the group consisting of:
methyl [(1S)-1-({(2S)-2-[4-(4'-{2-[(3S,7S,9S)-7,9-dimethyl-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}) carbonyl)-2-methylpropyl]carbamate;
methyl [(1S)-2-methyl-1-({(2S)-2-[4-(4'-{2-[(8S)-7-((2S)-3-methyl-2-{[(methyloxy)carbonyl]amino}butanoyl)-1,4-dioxa-7-azaspiro[4.4]non-8-yl]-1H-imidazol-4-yl})-4-biphenylyl)-1H-imidazol-2-yl]-1-pyrrolidinyl}) carbonyl)propyl]carbamate;
dimethyl (4,4'-biphenyldiylbis{1H-imidazole-4,2-diyl [(3S,7S,9S)-7,9-dimethyl-6,10-dioxa-2-azaspiro[4.5]decane-3,2-diyl][(2S)-3-methyl-1-oxo-1,2-butanediyl]})biscarbamate;
dimethyl (4,4'-biphenyldiylbis{1H-imidazole-4,2-diyl (8S)-1,4-dioxa-7-azaspiro[4.4]nonane-8,7-diyl[(2S)-3-methyl-1-oxo-1,2-butanediyl]})biscarbamate;
methyl ((1S)-1-methyl-2-{(3S)-3-[4-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-1H-imidazol-2-yl]-6,10-dioxa-2-azaspiro[4.5]dec-2-yl})-2-oxoethyl)carbamate;
methyl [(1S)-2-methyl-1-({(2S)-2-[4-(4'-{2-[(3 S)-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)propyl]carbamate;
methyl [(1S)-1-({(2S)-2-[4-(4'-{2-[(3S)-8,8-dimethyl-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)-2-methylpropyl]carbamate;
methyl [(1S)-2-methyl-1-({(2S)-2-[4-(4'-{2-[(3S)-2-((2S)-3-methyl-2-{[(methyloxy)carbonyl]amino}butanoyl)-6,10-dioxa-2-azaspiro[4.5]dec-3-yl]-1H-imidazol-4-yl}-4-biphenylyl)-1H-imidazol-2-yl]-1-pyrrolidinyl}carbonyl)propyl]carbamate-$d_6$;
methyl [(1S)-2-methyl-1-({(2S)-2-[4-(4'-{2-[(8S)-7-((2S)-3-methyl-2-{[(methyloxy)carbonyl]amino}butanoyl)-1,4-dioxa-7-azaspiro[4.4]non-8-yl]-1H-imidazol-4-yl})-4-biphenylyl)-1H-imidazol-2-yl]-1-pyrrolidinyl}carbonyl)propyl]carbamate-$d_4$;
methyl [(1S)-1-({(2S)-2-[4-(4'-{2-[(2R,3R,8S)-2,3-dimethyl-7-((2S)-3-methyl-2-{[(methyloxy)carbonyl]amino}butanoyl)-1,4-dioxa-7-azaspiro[4.4]non-8-yl]-1H-imidazol-5-yl})-4-biphenylyl)-1H-imidazol-2-yl]-1-pyrrolidinyl}carbonyl)-2-methylpropyl]carbamate;
methyl [(1S)-1-({(2S)-2-[4-(4'-{2-[(2S,3S,8S)-2,3-dimethyl-7-((2S)-3-methyl-2-{[(methyloxy)carbonyl]amino}butanoyl)-1,4-dioxa-7-azaspiro[4.4]non-8-yl]-1H-imidazol-5-yl})-4-biphenylyl)-1H-imidazol-2-yl]-1-pyrrolidinyl}carbonyl)-2-methylpropyl]carbamate;
methyl [(1S)-2-methyl-1-({(2S)-2-[4-(4'-{2-[(8S)-7-((2S)-3-methyl-2-{[(methyloxy)carbonyl]amino}butanoyl)-1,4-dithia-7-azaspiro[4.4]non-8-yl]-1H-imidazol-4-yl})-4-biphenylyl)-1H-imidazol-2-yl]-1-pyrrolidinyl}carbonyl)propyl]carbamate;
methyl [(1 S)-2-methyl-1-({(2S)-2-[4-(4'-{2-[(8 S)-7-((2S)-2-{[(methyloxy) carbonyl]amino}butanoyl)-1,4-dithia-7-azaspiro[4.4]non-8-yl]-1H-imidazol-4-yl}-4-biphenylyl)-1 H-imidazol-2-yl]-1-pyrrolidinyl}) carbonyl)propyl]carbamate;
methyl [(1S)-2-methyl-1-({(2S)-2-[4-(4'-{2-[(8S)-7-({[(methyloxy)carbonyl]amino}acetyl)-1,4-dithia-7-azaspiro[4.4]non-8-yl]-1H-imidazol-4-yl}-4-biphenylyl)-1H-imidazol-2-yl]-1-pyrrolidinyl}carbonyl)propyl]carbamate;
methyl [(1S)-2-methyl-1-({(2S)-2-[4-(4'-{2-[2-((2S)-3-methyl-2-{[(methyloxy)carbonyl]amino}butanoyl)-8-oxa-2-azaspiro[4.5]dec-3-yl]-1H-imidazol-4-yl}-4-biphenylyl)-1H-imidazol-2-yl]-1-pyrrolidinyl}carbonyl)propyl]carbamate;
methyl [(1S)-2-methyl-1-({(2S)-2-[4-(4'-{2-[2-((2S)-3-methyl-2-{[(methyloxy)carbonyl]amino}butanoyl)-8,8-dioxido-8-thia-2-azaspiro[4.5]dec-3-yl]-1H-imidazol-4-yl}-4-biphenylyl)-1H-imidazol-2-yl]-1-pyrrolidinyl}carbonyl)propyl]carbamate;
methyl [(1S)-1-({(2S)-2-[4-(4'-{2-[8,8-difluoro-2-((2S)-3-methyl-2-{[(methyloxy)carbonyl]amino}butanoyl)-2-azaspiro[4.5]dec-3-yl]-1H-imidazol-4-yl}-4-biphenylyl)-1H-imidazol-2-yl]-1-pyrrolidinyl}) carbonyl)-2-methylpropyl]carbamate;
1,1-dimethylethyl 2-{N-[(methyloxy)carbonyl]-L-valyl}-3-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,8-diazaspiro[4.5]decane-8-carboxylate;
methyl [(1S)-2-methyl-1-({(2S)-2-[4-(4'-{2-[2-((2S)-3-methyl-2-{[(methyloxy)carbonyl]amino}butanoyl)-2,8-diazaspiro[4.5]dec-3-yl]-1H-imidazol-4-yl}-4-biphenylyl)-1H-imidazol-2-yl]-1-pyrrolidinyl}carbonyl)propyl]carbamate;
methyl [(1S)-1-({(2S)-2-[4-(4'-{2-[8-acetyl-2-((2S)-3-methyl-2-{[(methyloxy)carbonyl]amino}butanoyl)-2,8-diazaspiro[4.5]dec-3-yl]-1H-imidazol-4-yl}-4-biphenylyl)-1H-imidazol-2-yl]-1-pyrrolidinyl}) carbonyl)-2-methylpropyl]carbamate;
methyl 2-{N-[(methyloxy)carbonyl]-L-valyl}-3-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,8-diazaspiro[4.5]decane-8-carboxylate;

1,1-dimethylethyl 6-{N-[(methyloxy)carbonyl]-L-valyl}-7-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,6-diazaspiro[3.4]octane-2-carboxylate;

methyl [(1S)-2-methyl-1-({(2S)-2-[4-(4'-{2-[6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate;

methyl [(1S)-1-({(2S)-2-[4-(4'-{2-[2-acetyl-6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}) carbonyl)-2-methylpropyl]carbamate;

methyl 6-{N-[(methyloxy)carbonyl]-L-valyl}-7-(4-{4'-[2-((2S)-1-{N-[(methyloxy)carbonyl]-L-valyl}-2-pyrrolidinyl)-1H-imidazol-4-yl]-4-biphenylyl}-1H-imidazol-2-yl)-2,6-diazaspiro[3.4]octane-2-carboxylate;

methyl [(1S)-2-methyl-1-({(2S)-2-[4-(4'-{2-[2-[(methylamino)carbonyl]-6-((2S)-3-methyl-2-{[(methyloxy)carbonyl]amino}butanoyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate;

methyl [(1S)-2-methyl-1-({(2S)-2-[4-(4'-{2-[6-((2S)-3-methyl-2-{[(methyloxy)carbonyl]amino}butanoyl)-2-(methylsulfonyl)-2,6-diazaspiro[3.4]oct-7-yl]-1H-imidazol-4-yl}-4-biphenylyl)-1H-imidazol-2-yl]-1-pyrrolidinyl}carbonyl)propyl]carbamate;

methyl [(1S)-1-({(2S)-2-[4-(4'-{2-[(7S)-2,2-difluoro-6-((2S)-3-methyl-2-{[(methyloxy)carbonyl]amino}butanoyl)-6-azaspiro[3.4]oct-7-yl]-1H-imidazol-4-yl}-4-biphenylyl)-1H-imidazol-2-yl]-1-pyrrolidinyl}) carbonyl)-2-methylpropyl]carbamate;

methyl [(1S)-2-methyl-1-({(2S)-2-[4-(4'-{2-[1-((2S)-3-methyl-2-{[(methyloxy)carbonyl]amino}butanoyl)-8-oxa-1-azaspiro[4.5]dec-2-yl]-1H-imidazol-4-yl}-4-biphenylyl)-1H-imidazol-2-yl]-1-pyrrolidinyl}carbonyl)propyl]carbamate;

methyl ((1S)-1-{[(2S)-2-(4-{4'-[2-(1-acetyl-8-oxa-1-azaspiro[4.5]dec-2-yl)-1H-imidazol-4-yl]-4-biphenylyl}-1H-imidazol-2-yl)-1-pyrrolidinyl]carbonyl}-2-methylpropyl)carbamate;

methyl [(1S)-1-({(2S)-2-[4-(4'-{2-[8,8-difluoro-1-((2S)-3-methyl-2-{[(methyloxy) carbonyl]amino}butanoyl)-1-azaspiro[4.5]dec-2-yl]-1H-imidazol-4-yl}-4-biphenylyl)-1H-imidazol-2-yl]-1-pyrrolidinyl}carbonyl)-2-methylpropyl]carbamate;

methyl [(1S)-1-({8,8-difluoro-2-[4-(4'-{2-[(2S)-1-((2S)-3-methyl-2-{[(methyloxy)carbonyl]amino}butanoyl)-2-pyrrolidinyl]-1H-imidazol-4-yl}-4-biphenylyl)-1H-imidazol-2-yl]-1-azaspiro[4.5]dec-1-yl}carbonyl)propyl]carbamate;

methyl ((1S)-2-{8,8-difluoro-2-[4-(4'-{2-[(2S)-1-((2S)-3-methyl-2-{[(methyloxy) carbonyl]amino}butanoyl)-2-pyrrolidinyl]-1H-imidazol-4-yl}-4-biphenylyl)-1H-imidazol-2-yl]-1-azaspiro[4.5]dec-1-yl}-1-methyl-2-oxoethyl)carbamate;

methyl [(1S)-1-({8,8-difluoro-2-[4-(4'-{2-[(2S)-1-((2S)-3-methyl-2-{[(methyloxy) carbonyl]amino}butanoyl)-2-pyrrolidinyl]-1H-imidazol-4-yl}-4-biphenylyl)-1H-imidazol-2-yl]-1-azaspiro[4.5]dec-1-yl}carbonyl)-3-methylbutyl]carbamate;

methyl ((1S)-1-{[(2S)-2-(4-{4'-[2-(1-acetyl-8,8-difluoro-1-azaspiro[4.5]dec-2-yl)-1H-imidazol-4-yl]-4-biphenylyl}-1H-imidazol-2-yl)-1-pyrrolidinyl]carbonyl}-2-methylpropyl)carbamate; and methyl [(1S)-2-methyl-1-({(2S)-2-[4-(4'-{2-[1-((2S)-3-methyl-2-{[(methyloxy) carbonyl]amino}butanoyl)-8,8-dioxido-8-thia-1-azaspiro[4.5]dec-2-yl]-H-imidazol-4-yl}-4-biphenylyl)-1H-imidazol-2-yl]-1-pyrrolidinyl}carbonyl)propyl]carbamate; and pharmaceutically acceptable salts thereof; and (b) administering to the patient in need one or more therapeutic agents.

14. A method as claimed in claim 13 wherein said one or more therapeutic agents is interferon.

15. A method as claimed in claim 13 wherein said one or more therapeutic agents is ribavirin.

16. A method as claimed in claim 13 wherein said therapeutic agents are interferon and ribavirin.

\* \* \* \* \*